(12) United States Patent
Heintz et al.

(10) Patent No.: US 8,013,118 B2
(45) Date of Patent: Sep. 6, 2011

(54) LYNX POLYPEPTIDES

(75) Inventors: Nathaniel Heintz, Pelham Manor, NY (US); Julie M. Miwa, New York, NY (US); Ines Ibanez-Tallon, New York, NY (US)

(73) Assignee: The Rockefeller University, New York, NY (US)

( * ) Notice: Subject to any disclaimer, the term of this patent is extended or adjusted under 35 U.S.C. 154(b) by 1233 days.

(21) Appl. No.: 10/322,359

(22) Filed: Dec. 18, 2002

(65) Prior Publication Data
US 2010/0004162 A1    Jan. 7, 2010

Related U.S. Application Data

(63) Continuation of application No. 09/320,864, filed on May 27, 1999, now abandoned, which is a continuation-in-part of application No. 09/156,926, filed on Sep. 18, 1998, now abandoned.

(51) Int. Cl.
*C07K 1/00* (2006.01)
*C07K 14/00* (2006.01)
*C07K 17/00* (2006.01)

(52) U.S. Cl. .................................................... 530/350

(58) Field of Classification Search .................. None
See application file for complete search history.

(56) References Cited

U.S. PATENT DOCUMENTS

| | | | |
|---|---|---|---|
| 3,654,090 A | 4/1972 | Schuurs et al. | |
| 3,850,752 A | 11/1974 | Schuurs et al. | |
| 4,016,043 A | 4/1977 | Schuurs et al. | |
| 4,342,566 A | 8/1982 | Theofilopoulos et al. | |
| 4,631,211 A | 12/1986 | Houghton | |
| 4,816,397 A | 3/1989 | Boss et al. | |
| 4,816,567 A | 3/1989 | Cabilly et al. | |
| 4,981,784 A | 1/1991 | Evans et al. | |
| 5,010,175 A | 4/1991 | Rutter et al. | |
| 5,770,580 A | 6/1998 | Ledley et al. | |
| 6,130,061 A * | 10/2000 | Ni et al. ........ | 435/69.1 |
| 6,342,581 B1 | 1/2002 | Rosen et al. | |
| 6,514,947 B2 | 2/2003 | Rolland et al. | |
| 2004/0044191 A1* | 3/2004 | Fischer et al. ........... | 536/23.1 |

FOREIGN PATENT DOCUMENTS

| | | |
|---|---|---|
| WO | WO 88/03168 | 5/1988 |
| WO | WO 90/13678 | 11/1990 |
| WO | WO 92/00252 | 1/1992 |
| WO | WO 94/28028 | 12/1994 |
| WO | WO 96/35808 | 11/1996 |
| WO | WO 99/02546 | 1/1999 |

OTHER PUBLICATIONS

Altschul, Stephen, F. et al., "Basic Local Alignment Search Tool," Journal of Molecular Biology, vol. 215, pp. 403-410 (1990).
Brandon, Eugene, P. et al., "Defective Motor Behavior and Neural Gene Expression in RII beta-Protein Kinase a Mutant Mice," The Journal of Neuroscience, vol. 18, No. 10, pp. 3639-3649 (May 15, 1998).
Cells, Julio, E. et al. "Human 2-D Page databases for proteome analysis in health and disease: http://biobase.dk/cgi-bin/cells," FEBS Letters, vol. 398, pp. 129-134 (1996).
Clarke, Paul, B.S. et al., "Nicotinic Binding in Rat Brain: Autoradiographic Comparison of [3H]Acetylcholine, [3H]Nicotine, and [125I]-alpha-Bungarotoxin," The Journal of Neuroscience, vol. 5, No. 5, pp. 1307-1315 (May 1985).
Cote, Richard J. et al., "Generation of human monoclonal antibodies reactive with cellular antigens," Proceedings of the National Academy of Sciences, vol. 80, pp. 2026-2060 (Apr. 1983).
Croxen, R. et al., "Mutations in different functional domains of the human muscle acetylcholine receptor alpha subunit in patients with the slow-channel congenital myasthenic syndrome," Human Molecular Genetics, vol. 6, No. 5, pp. 767-774 (1997).
Cwirla, Steven, E. et al., "Peptides on phage: A vast library of peptides for identifying ligands," Proceedings of the National Academy of Sciences, vol. 87, pp. 6378-6382 (Aug. 1990).
Grunstein, Michael et al., "Colony hybridization: A method for the isolation of clofied DNAs that contain a specific gene," Proceedings of the National Academy of Sciences, vol. 72, No. 10, pp. 3691-3965 (Oct. 1975).
Hanninen, Arno et al., "Ly-6C regulates endothelial adhesion and homing of CD8+ T Cells by activating integrin-dependent adhesion pathways," Proceedings of the National Academy of Sciences, vol. 94, pp. 6898-6903 (Jun. 1997).
Inoue, Seiji et al., "Amino Acid Sequences of Nerve Growth Factors Derived from Cobras Venoms," FEBS Letters, vol. 279, No. 1, pp. 38-40 (Feb. 1991).
Jay, Ernest et al., "Chemical Synthesis of a Biologically ActiveG ene for Human Immune Interferon-gamma," The Journal of Biological Chemistry, vol. 259, No. 10, pp. 6311-6317 (1984).
Joikkonen, Mikael et al., "A toxin from the green mamba Dendroaspis angusticeps: amino acid sequence and selectivity for muscarinic m4 receptors," FEBS Letters, vol. 352, pp. 91-94 (1994).
Kuhar, Siobhan, G et al., "Changing patterns of gene expression define four stages of cerebellar granule neuron differentiation," Development, vol. 117, pp. 97-104 (1993).
Malek, Thomas, R. et al., "Role of Ly-6 in Lymphocyte Activation," Journal of Experimental Medicine, vol. 164, pp. 709-722 (Sep. 1996).

(Continued)

*Primary Examiner* — Robert Landsman
(74) *Attorney, Agent, or Firm* — Lowenstein Sandler PC

(57) ABSTRACT

The present invention provides a novel family of polypeptides which are ligand-gated channel receptor accessory molecules or ligands, denoted Lynx. This invention provides an isolated polypeptide comprising an amino acid sequence of a Lynx polypeptide in which the amino acid sequence is set forth in SEQ ID NO:2, SEQ ID NO:4, or SEQ ID NO:15, including fragments, mutants, variants, analogs, homologs, or derivatives of the amino acid sequences set forth in SEQ ID NO:2, SEQ ID NO:4, or SEQ ID NO:15. This invention further provides an isolated immunogenic polypeptide; an isolated nucleic acid; pharmaceutical compositions and diagnostic and therapeutic methods of use of the isolated polypeptides and nucleic acids of the present invention; assays for compounds which mimic, alter or inactivate the polypeptides of the present invention for use in therapy; and methods of isolating Lynx polypeptides and the nucleic acids encoding such polypeptides.

5 Claims, 17 Drawing Sheets

OTHER PUBLICATIONS

Needels, Michael, C. et al., "Generation and screening of an oligonucleotide-encoded synthetic peptide library," Proceedings of the National Academy of Sciences, vol. 90, pp. 10700-10704 (Nov. 1993).

Ohlmeyer, Michael, H.J. et al., "Complex synthetic chemical libraries indexed with molecular tags," Proceedings of the National Academy of Sciences, vol. 90, pp. 10922-10926 (Dec. 1993).

Rock, Kenneth, L. et al., "Tap, A Novel T Cell-Activating Protein Involved in the Stimulation of MHC-Restricted T Lymphocytes," Journal of Experimental Medicine, vol. 163, pp. 315-333 (Feb. 1986).

Role, Lorna W. et al,. "Nicotinic Receptors in the Development and Modulation of CNS Synapses," Neuron, vol. 16., pp. 1077-1085 (Jun. 1996).

Schyler, Bruce, D. et al., "alpha-Bungarotoxin binding to two acetylcholine receptor alpha-peptides and their methylmercury-modified analogs: intrinsic phosphorescence and optically detected magnetic resonance studies," FEBS Letters, vol. 297, No. 1, 2, pp. 87-90 (1992).

Miwa, Julie, M. et al., "lynx1, an Endogenous Toxin-like Modulator of Nicotinic Acetylcholine Receptors in the Mammalian CNS," Neuron, vol. 23, No. 1, pp. 105-114 (May 1999).

Chen, DaNong et al., "The alpha-Bungarotoxin-binding Nicotinic Acetylcholine Receptor from Rat Brian Contains Only the alpha7 Subunit," The Journal of Biological Chemistry, vol. 272, No. 38, pp. 24024-24029 (Sep. 19, 1997).

Ibanez-Tallon, Ines et al., "Novel Modulation of Neuronal Nicotinic Acetylcholine Receptors by Associationi with the Endogenous Prototoxin lynx1," Neuron, vol. 33, pp. 893-903 (Mar. 14, 2002).

Cousin, Xavier et al., "Identification of a Novel Type of Alternatively Spliced Exon from the Acetylcholinesterase Gene of *Bungarus fasciatus*," The Journal of Biological Chemistry, vol. 273, pp. 9812-9820 (Apr. 17, 1998).

International Search Report for WO 00/17356, mailed May 10, 2000.

Final Office Action dated May 3, 2010 issued in connection with related U.S. Appl. No. 11/899,406.

Amendment (with pending claims) dated Mar. 2, 2010 submitted in connection with related U.S. Appl. No. 11/899,406.

Abuchowski et al., "Immunosuppressive Properties and Circulating Life of Achromobacter Glutamainase-Asparaginase Covalently Attached to Polyethylene Glycol in Man," Cancer Treat Rep 65:1077-1081, 1981.

Ausubel, R.M. "Current Protocols in Molecular Biology," Chpt. 12.3-16.4 (1994).

Basus et al., "NMR Solution Structure of an alpha-Bungarotoxin/Nicotinic Receptor Peptide Complex," Biochemistry, vol. 32, 12290-12298 (1993).

Benton and Davis, "Screening lamba gt Recombinant Clones by Hybridization to Single Plaques in situ," Science, New Series, vol. 196, No. 4286 (Apr. 8, 1977), pp. 180-812.

Brakeman et al., "Homer: a protein that selectively binds metabotropic glutamate receptors," Nature, vol. 386, pp. 284288 (Mar. 20, 1997).

Brooks et al., CHARMM: A Program for Macromolecular Energy, Minimization, and Dynamics Calculations, Journal of Computational Chemistry, vol. 4, No. 2, 187-217 (1983).

Brown et al., "Chemical Transmission in the Rat Interpeduncular Nucleus in vitro," J. Physiol. (1983), vol. 341, pp. 655-670.

Buchwald et al., "Long-term, continuous intravenous heparin administration by an implantable infusion pump in ambulatory patients with recurrent venous thrombosis," Surgery vol. 88, pp. 507-516, 1980.

During et al., "Controlled Release of Dopamine from a Polymeric Brain Implant: In Vivo Characterization," Ann. Neurol 1989; 25:351-356.

Rodriquez and Carrasco, "Nonradioactive Northwestern Analysis Using Biotinylated Riboprobes," BioTechniques, vol. 17., No. 4 pp. 702-707 (1994).

Cech, "Ribozymes and Their Medical Implications" JAMA 1988; 260:3030-3034.

Celis (Ed.), "Cell Biology: A Laboratory Handbook," Academic Press, Inc., 1994.

Changeux et al., "Brain nicotinic receptors: structure and regulation, role in learning and reinforcement," Brain Research Reviews 26 (1998) 198-216.

Chen and Patrick, "The alpha-Bungarotoxin-binding Nicotinic Acetylcholine Receptor from Rat Brain Contains Only the alpha-7 Subunit," Journal of biological Chemistry vol. 272, No. 38, Sep. 19, 1997, pp. 24024-24029.

Cheng et al., "Complementary Gradients in Expression and Binding of ELF-1 and Mek4 in Development of the Topographic Retinotectal Projection Map," Cell. vol. 82, 371-381, Aug. 11, 1995.

Cheng and Flanagan, "Identification and Cloning of ELF-1, a Developmentally Expressed Ligand for the Mek4 and Sek Receptor Tyrosine Kinases," Cell, vol. 79, 157-168, Oct. 7, 1994.

Cole et al., "The EBV-Hybridoma Technique and its Application to Human Lung Cancer," Monoclonal Antibodies and Cancer Therapy, pp. 77-96, 1985.

Duggen et al., "Alpha-bungarotoxin, cobra neurotoxin and excitation of Renshaw cells by acetylcholine," Brain Research, 107 (1976) 166-170.

Contant et al., "Ultrastructural Characterization of the Acetylcholine Innervation in Adult Rat Neostriatum," Neuroscience vol. 71, No. 4, pp. 937-947, 1996.

Coull, "Neural Correlates of Attention and Arousal: Insights from Electrophysiology, Functional Neuroimaging and Psychopharmacology," Progress in Neurobiology, vol. 55, pp. 343-361, 1998.

Cowan, "The Emergence of Modern Neuraanatomy and Developmental Neurobiology," Neuron, vol. 20, 413-426, Mar. 1998.

Davidson and Dennis, "Evolutionary Relationships and Implications for the Regulation of Phospholipase A2 from Snake Venom to Human Secreted Forms," J. Mol. Evol. (1990) 31:228-238.

Del Toro et al., "Immunocytochemical Localization of the alpha-7 Subunit of the Nicotinic Acetylcholine Receptor in the Rat Central Nervous System," Journal of Comparative Neurology, 349:325-342 (1994).

Descarries, "Diffuse Transmission by Acetylcholine in the CNS," Progress in Neurobiology, vol. 53, pp. 603-625, 1997.

Devlin et al., "Random peptide libraries: A source of specific protein binding molecules," Science, New Series, vol. 249, No. 4967 (Jul. 27, 1990), pp. 404-406.

DeZeeuw et al., "Expression of a Protein Kinase C Inhibitor in Purkinje Cells Blocks Cerebellar LTD and Adaptation of the Vestibulo-Ocular Reflex," Neuron, vol. 20, 495-508, Mar. 1998.

Dong et al., "GRIP: a synaptic PDZ domain-containing protein that interacts with AMPA receptors," Nature vol. 386, pp. 279-284 (Mar. 20, 1997).

Dresher et al., "In Vitro Guidance of Retinal Ganglion Cell Axons by RAGS, a 25 kDa Tectal Protein Related to Ligand for Eph Receptor Tyrosine Kinases," Cell, vol. 82, 359-370, Aug. 11, 1995.

Edge et al., "Total synthesis of a human leukocyte interferon gene," Nature vol. 292, Aug. 20, 1981.

Everitt and Robbins, "Central Cholinergic Systems and Cognition," Annu. Rev. Psychol. 1997, 48:649-684.

Fields and Song, "A novel genetic system to detect protein-protein interactions," Nature, vol. 340, pp. 245-246, Jul. 20, 1989.

Fleming et al., "Characterization of two novel Ly-6 genes. Protein sequence and potential structural similarity to alpha-bungarotoxin and other neurotoxins," J. Immunol. 1993; 150; 5379-5390.

Fletcher et al., "Structure of a soluble, glycosylated form of the human complement regulatory protein CD59," Structure, Mar. 1994, 2:185-199.

Fodor et al., "Light-Directed Spatially Addressable Parallel Chemical Synthesis," Science, New Series, vol. 251, No. 4995 (Feb. 15, 1991), pp. 767-773.

Freshney (ed.), "Animal Cell Culture," IRL Press (1986).

Furka et al., "General method for rapid synthesis of multicomponent peptide mixtures," Im. J. Peptide Protein Res. 37, 1991, 487-493.

Gallagher and Rapp, "The Use of Animal Models to Study the Effects of Aging on Cognition," Annu. Rev. Psychol. 1997, 48:339-70.

Garside and Mazurek, "Role of Glutamate Receptor Subtypes in the Differential Release of Somatostatin, Neuropeptide Y, and Substance P in Primary Serum-Free Cultures of Striatal Neurons," Synapse 27:161-167, 1997.

Geula, "Abnormalities of neural circuitry in Alzheimer's disease," Neurology, 1998; 51(Suppl 1):S18-S29.

Geysen et al., "Strategies for epitope analysis using peptide synthesis," Journal of Immunological Methods, 102 (1987) 259-274.

Geysen et al., "A priori delineation of a peptide which mimics a discontinuous antigenic determinant," Molecular Immunology, vol. 23, No. 7, pp. 709-715, 1986.

Glover (ed.), "DNA Cloning: A Practical Approach," IRL Press (1985).

Goodson, "Chapter 6: Dental Applications," in Medial Applications of Controlled Release, pp. 115-138 (1985).

Gray et al., "Hippocampal synaptic transmission enhanced by low concentrations of nicotine," Nature, vol. 383, Oct. 24, 1996.

Gumley et al., "Tissue expression, structure and function of the murine Ly-6 family of molecules," Immunology and Cell Biology (1995) 73, 277-296.

Gumley et al., "Sequence and structure of the mouse ThB gene," Immunogenetics (1995) 42:221-224.

Kamiura et al., "Long-range physical map of the Ly-6 complex: mapping the Ly-6 multigene family by field-inversion and two-dimensional gel electrophoresis," Genomics 12, 89-105 (1992).

Hambor et al., "Functional consequences of anti-sense RNA-mediated inhibition of CD8 surface expression in a human T cell clone," J. Exp. Med. vol. 168, 1237-1245 (Oct. 1988).

Hames and Higgins (eds.), "Nucleic Acid Hybridization," IRL Press, 1985.

Hames and Higgins (eds.), "Transcription and translation," IRL Press, 1984.

Hanninen et al., "Ly-6C regulates endothelial adhersion and homing of CD8+ T cells by activating integrin-dependent adhesion pathways," Proc. Natl. Acad. Sci. USA, vol. 94, pp. 6898-6903, Jun. 1997.

Harfstrand et al., "Distribution of nicotinic cholinergic receptors in the rat tel- and diencephalon: a quantitative receptor autoradiographical study using [3H]- acetylcholine, [alpha-125]bungarotoxin and [3H]nicotine," Acta Physiol Scand, 1988, 132, 1-14.

Harlow and Lane, "Antibodies: A laboratory manual," Cold Spring Harbor Laboratory, 1988.

Harrison and Sternberg, "The Disulphide beta-cross: From Cystine Geometry and clustering to Classification of Small Disulphide-rich Protein Folds," J. Mol. Biol. (1996) 264, 603-623.

Hart et al., "Genetic Linkage Analysis of the Murine Developmental Mutant Velvet Coat (Ve) and the Distal Chromosome 15 Developmental Genes Hox-3.1, Rar-g, Wnt-1, and Krt-2," Journal of Experimental Zoology, 263:83-95 (1992).

Hashimoto et al., "A Neural Cell-Type-Specific Expression System Using Recombinant Adenovirus Vectors," Human Gene Therapy 7:149-158 (Jan. 20, 1996).

Hasseloff and Gerlach, "Simple RNA enzymes with new and highly specific endoribonuclease activities," Nature, vol. 334, Aug. 18, 1988.

Hayashi et al., "Neosurugatoxin, a Specific Antagonist of Nicotinic Acetylcholine Receptors," Journal of Neurochemistry, 42, 1491-1494 (1984).

Hillier et al., "Homosapiens cDNA Clone 172689.5," Database EMEST27, E.B.I., Accession No. H19572, XP002136324 (Jul. 7, 1995).

Howard et al., "Intracerebral drug delivery in rats with lesion-induced memory deficits," J. Neurosurg 71:105-112, 1989.

Hunt and Schmidt, "The relationship of alpha-bungarotoxin binding activity and cholinergic termination within the rat hippocampus," Neuroscience vol. 4, pp. 585-592 (1979).

Huse et al. et al., "Generation of a large combinatorial library of the immunoglobulin repertoire in phage lambda," Science, New Series, vol. 246, No. 4935, Dec. 8, 1989, pp. 1275-1281.

John et al., "Genomic sequences encoding the acidic and basic subunits of Mojave toxin: unusually high sequence identity of non-coding regions," Gene, 139 (1994) 229-234.

Lei et al., Characterization of the Erwinia carotovora pelB Gene and Its Product Pectate Lyase, J. Bacteriol. 169, 4379 (1987).

Kim et al., Expression and Characterization of Recombinant Single-Chain Fv and Fv Fragments Derived From a Set of Catalytic Antibodies, Mol. Immunol. 34, 891 (1997).

Chan et al., Fluorescence Resonance Energy Transfer Analysis of Cell Surface Receptor Interactions and Signaling Using Spectral Variants of the Green Fluorescent Protein, Cytometry 44, 361-68 (2001).

Hu et al., A protein chip approach for high-throughput antigen identification and characterization, Proteomics 7, 2151-61 (2007).

Lin et al., KChIP3: A binding protein for Taiwan banded krait beta-bungarotoxin, Toxicon 47, 265-70 (2005).

Sekine-Aizawa and Huganir, Imaging of receptor trafficking by using alpha-bungarotoxin-binding-site-tagged receptors, Proc. Nat'l Acad. Sci. 101, 17114-119 (2004).

Goodson, Chapter 6 in Medical Applications of Controlled Release vol. 2, Chapter 6, "Dental Applications," (1984).

Chung et al., Two-Dimensional Standing Wave Total Internal Reflection Fluorescence Microscopy: Superresolution Imaging of Single Molecular and Biological Specimens, Biophys. J. 93, 1747-57 (2007).

Salminen et al., The subunit composition and pharmacology of alpha-Conotoxin MII-binding nicotinic acetylcholine receptors studied by a novel membrane-binding assay, Neuropharmacol. 48, 696-705 (2005).

Berg and Conroy, Nicotinic alpha-7 Receptors: Synaptic Options and Downstream Signaling in Neurons, J. Neurobiol. 53, 512-23 (2002).

Hamill et al., Improved Patch-Clamp Techniques for High-Resolution Current Recording from Cells and Cell-Free Membrane Patches, Pflugers Arch. 391, 85-100 (1981).

Li et al., Microfluidic System for Planar Patch Clamp Electrode Arrays, Nano Lett. 6, 815-19 (2006).

Dajas-Bailador et al., The alpha-7 nicotinic acetylcholine receptor subtype mediates nicotine protection against NMDA excitotoxicity in primary hippocampal cultures through a Ca2+ dependent mechanism, Neurpharmacol. 39, 2799-807 (2000).

Windhorst and Johansson (eds.), Modern Techniques in Neuroscience Research, Spring Lab Manuals, Chapter 5, "Electrical Activity of Individual Neurons in Situ: Extra- and Intracellular Recording," by Lalley et al., and Chapter 9, "In Vitro Preparations," by Ballanyi (1999).

Langer and Peppas, Chemical and Physical Structure of Polymers as Carriers for Controlled Release of Bioactive Agents: A Review, Macromol. Sci. Rev. Macromol. Chem. 23, 61 (1983).

Clarke and Kumar, The effects of nicotine on locomotor activity in non-tolerant and tolerant rats, Br. J. Pharmacol. 78, 329-37 (1983).

Steidl et al., The adult rat hippocampal slice revisited with multi-electrode arrays, Brain Res. 1096, 70-84 (2006).

Ding et al., Alterations of striatal neurotransmitter release in aquaporin-4 deficient mice: An in vivo microdialysis study, Neurosci. Lett. 422, 175-80 (2007).

Nashmi et al., Assembly of alpha-4 beta-2 Nicotinic Acetylcholine Receptors Assessed with Functional Fluorescently Labeled Subunits: Effects of Localization, Trafficking, and Nicotine-Induced Upregulation in Clonal Mammalian Cells and in Cultured Midbrain Neurons, J. Neurosci. 23, 11554-67 (2003).

Gill et al., A Cell-Based Rb+ Flux Assay of the Kv1.3 Potassium Channel, Assay Drug Dev. Technol. 5, 373-80 (2007).

Vijayaraghavan et al., Nicotinic Receptors That Bind alpha-bungarotoxin on Neurons Raise Intracellular Free Ca2+, Neuron 8, 353-62 (1992).

Sakmann and Neher (eds.), Single Channel Recording, Chapter 9, The Principles of Stochastic Interpretation of Ion-Channel Mechanisms, by Colquhoun and Hawkes (1983).

Wang et al., Peri-infarct temporal changes in intrinsic optical signal during spreading depression in focal ischemic rat cortex, Neurosci. Lett. 2, 133-38 (2007).

Crawley, What's Wrong With My Mouse? Behavioral Phenotyping of Transgenic and Knockout Mice, Chapter 6, "Learning and Memory," (2nd ed. 2007).

Rees et al., "Crystal structure of a snake venom cardiotoxin," Proc. Natl. Acad. Sci. USA, vol. 84, pp. 3132-3136, May 1987.

Speth et al., "Nicotinic Cholinergic receptors in rat brain identified by [125 I] Naja naja siamensis alpha-toxin binding," Brain Research, 131 (1977) 350-355.

Robbins, "Cognitivie enhancers in theory and practice: studies of the cholinergic hypothesis of cognitive deficits in Alzheimer's disease," Behavioural Brain Research 83 (1997) 15-23.
Robbins, "Arousal systems and attentional processes," Biological Psychology 45 (1997) 57-71.
Romano and Goldstein, "Stereospecific Nicotine Receptors on Rat Brain Membranes," Science, New Series, vol. 210, No. 4470 (Nov. 7, 1980), pp. 647-650.
Sali and Bludell, "Comparative Protein Modelling by Satisfaction of Spatial Restraints," J. Mol. Biol. (1993) 234, 779-815.
Croxen et al., "Mutations in different functional domains of the human muscle acetylcholine receptor alpha subunit in patients with the slow-channel congenital myasthenic syndrome," Human Molecular Genetics, 1997, vol. 6, No. 5, 767-774.
Sanchez and Sali, "Evaluation of Comparative Protein Structure Modeling by MODELLER-3," Proteins: Structure, Function and Genetics, Suppl. 1:50-58 (1997).
Sippl, "Recognition of Errors in Three-Dimensional Structures of Proteins," Proteins: Structure, Function, and Genetics, 17:355-362 (1993).
Sanes, "Mechanistic Relationships Between Development and Learning, Chapter 10: Synapse Formation," John Wiley & Sons Ltd., 1988.
Saudek et al., "A Preliminary Trial of the Programmable Implantable Medication System for Insulin Delivery," New England Journal of Medicine, vol. 321, No. 9, 574-579, Aug. 31, 1989.
Schoepfer, "Brain alpha-Bungarotoxin Binding Protein cDNAs and MAbs Reveal Subtypes of This Branch of the Ligand-Gated Ion Channel Gene Superfamily," Neuron, vol. 5, 35-48, 1990.
Schwartz, "Nicotinic Cholinergic Receptors Labeled by [3H]Acetylcholine in Rat Brain," Molecular Pharmacology, 22:56-62, 1982.
Scott and Smith, "Searching for Peptide Ligands with an Epitope Library," Science, New Series, vol. 249, No. 4967 (Jul. 27, 1990), pp. 386-390.
Sefton, "Implantable Pumps," CRC Critical Reviews in Biomedical Engineering, vol. 14, Issue 3, 201-240 (1987).
Serafini et al., "The Netrins Define a Famiy of Axon Outgrowth-Promoting Proteins Homologous to C. elegans UNC-6," Cell, vol. 78, 409-424, Aug. 12, 1994.
Sine, "Mutation of the Acetylcholine Receptor alpha Subunit Causes a Slow-Channel Myasthenic Syndrome by Enhancing Agonist Binding Affinity," Neuron, vol. 15, 229-239, Jul. 1995.
Sippl, "Boltzmann's principle, knowledge-based mean fields and protein folding. An approach to the computational determination of protein structures," Journal of Computer-Aided Molecular Design, 7(1993) 473-501.
Smolen and Ball, "Controlled Drug Bioavailability," John Wily & Sons, 1985.
Stiles, "Acetylcholine receptor binding characteristics of snake and cone snail venom postsynaptic neurotoxins: further studies with a non-radioactive assay," Toxincon, vol. 31, No. 7, pp. 825-834, 1993.
Jay et al., "Chemical synthesis of a biologically active gene for human immune interferon-lambda," Journal of Biological Chemistry, vol. 259, No. 10, pp. 6311-6317, May 25, 1984.
E. Karlsson, "Handbook of Experimental Pharmacology, vol. 52, Chapter 5: Chemistry of Protein Toxins in Snake Venoms," Springer Varlag, 1978.
Takeda et al., "Construction of chimaeric processed immunoglobulin genes containing mouse variable and human constant region sequences," Nature, vol. 314, pp. 452-454 (Apr. 4, 1985).
Tessier-Lavigne and Goodman, "The Molecular Biology of Axon Guidance," Science, New Series, vol. 274, No. 5290 (Nov. 15, 1996), pp. 1123-1133.
IUPAC-IUB Commission on Biochemical Nomenclature, "A One-Letter Notation for Amino Acid Sequences Tentative Rules," Journal of Biological Chemistry, vol. 243, No. 13, Jul. 10, 1968, pp. 3557-3559.
Malek et al., "Role of Ly-6 in Lymphocyte Activation," Journal of Experimental Medicine, vol. 164, pp. 709-722, Sep. 1986.
Udenfriend and Kodukula, "How glycosyl-phophatidylinositol-anchored membrane proteins are made," Annu. Rev. Biochem. 1995, 64:563-91 (1995).

Weintraub, "Antisense RNA and DNA," Scientific American, pp. 40-46, Jan. 1990.
Woodward (ed.), Immobilised cells and enzymes, IRL Press, 1985.
Role and Berg, "Nicotinic Receptors in the Development and Modulation of CNS Synapses," Neuon, vol. 16, 1077-1085, Jun. 1996.
Schyler et al., "alpha-Bungarotoxin binding to two acetylcholine receptor alpha-peptides and their methylmercury-modified analogs: intrinsic phosphorescence and optically detected magnetic resonance studies," FEBS 10657, vol. 297, No. 1, 2, pp. 87-90 (Feb. 1992).
Katre et al., "Chemical modification of recombinant interleukin 2 by polyethylene glycol increases its potency in the murine Meth A sarcoma model," Proc. Natl. Acad. Sci. USA, vol. 84, pp. 1487-1491, Mar. 1987.
Katz and Shatz, "Synaptic Activity and theConstruction of Cortical Circuits," Science, New Series, vol. 274, No. 5290 (Nov. 15, 1996), pp. 1133-1138.
Katz-Levy et al., "Single amino acid analogs of a myasthenogenic peptide modulate specific T cell responses and prevent the induction of experimental autoimmune myasthenia gravis," Journal of Neuroimmunology 85 (1998) 78-86.
Kini and Chan, "Accelerated Evolution and Molecular Surface of Venom Phospholipase A2 Enzymes," J. Mol. Evol. (1999) 48:125-132.
Kochva et al., "Sarafotoxins and endothelins: evolution, structure and function," Toxicon, vol. 31, No. 5, pp. 541-568, 1993.
Kohler and Milstein, "Coninuous cultures of fused cells secreting antibody of predefined specificity," Nature, vol. 256, Aug. 7, 1975.
Kolodkin et al., "The semaphorin Genes Encode a Family of Transmembrane and Secreted Growth Cone Guidance Molecules," Cell, vol. 75 1369-1399, Dec. 31, 1993.
Kozbor and Roder, "The production of monoclonal antibodies from human lymphocytes," Immunology Today, vol. 4, No. 3, 1983.
Langer and Wise, "Medical Applications of Controlled Release," CRC Press, Inc., 1984.
Langer, "New Methods of Drug Delivery," Science, New Series, vol. 249, No. 4976 (Sep. 28, 1990), pp. 1527-1533.
Larramendi and Victor, "Synapses on the pukinje cell spines in the mouse: an electronmicroscopic study," Brain Research, 5 (1967) 15-30.
Le Goas, "alpha-cobratoxin: Proton NMR Assignments and Solution Structure," Biochemistry 1992, 31, 4867-4875.
Levy et al., "Inhibition of Calcification of bioprosthetic Heart Valves by Local Controlled-Release Diphosphonate," Science, New Series, vol. 228, No. 4696 (Apr. 12, 1985), pp. 190-192.
Lopez-Berestein, "Treatment of Systemic Fungal Infections with Liposomal-Amphotericin B," Liposomes in the Therapy of Infectious Diseases and Cancer, pp. 317-327, 1989.
Love and Stroud, "The crystal structure of alpha-bungarotoxin at 2.5 A resolution: relation to solution structure and binding to aceytlcholine receptor," Protein Engineering, vol. 1, No. 1, pp. 37-46, 1986.
Luo et al., "Collapsin: A Protein in Brain That Induces the Collapse and Paralysis of Neuronal Growth Cones," Cell. vol. 75, 217-227, Oct. 22, 1993.
Gait (ed.), "Oligonucleotide synthesis: a practical approach," IRL Press (1984).
Maley et al., "Immunohistochemical Localization of Substance P and Enkephalin in the Nucleus Tractus Solitarii of the Rhesus Monkey, Macaca mulatta," Journal of Comparative Neurology, 260:483-490 (1987).
Perbal, "A Practical Guide to Molecular Cloning," John Wiley & Sons, 1984.
Marcus-Sekura, "Techniques for Using Antisense Oligodeoxyribonucleotides to Study Gene Expression," Analytical Biochemistry 172, 289-295 (1988).
Marks and Collins, "Characterization of Nicotine Binding in Mouse Brain and Comparison with the Binding of alpha-bungarotoxin and Quinulindinyl Benzilate," Molecular Pharmacology, 22:554-564, 1982.
Marra, "Barstead Mouse Mysotubes MPLRB5 Mus Musculus cDNA Clone 10657 5," Database EMEST1, E.B.I., Accession No. AA619349, XP002135337 (Oct. 16, 1997).

McGehee et al., "Nicotine Enhancement of Fast Excitatory Synaptic Transmission in CNS by Presynaptic Receptors," Science, New Series, vol. 269, No. 5231 (Sep. 22, 1995), pp. 1692-1696.

Miwa, "Identification and Characterization of a Neuronal Cell Surface Protein: a novel member of the alpha-bungarotoxin/Ly-6 Superfamily of Genes," Diss. Abs. Int, vol. 58, No. 3, XP000892500 (Sep. 3, 1997).

Morrison et al., "Isolation of Transformation-Deficient *Streptococcus pneumoniae* mutants defective in control of competence, using insertion-duplication mutagenesis with the erythromycin resistance determinant of pAMbeta1," Journal of Bacteriology, Sep. 1984, pp. 870-876.

Nambair et al., "Total synthesis and cloning of a gene coding for the ribonuclease S protein," Science, New Series, vol. 223, No. 4642 (Mar. 23, 1984), pp. 1299-1301.

Neuberger et al., "Recombinant antibodies possessing novel effector functions," Nature vol. 312, Dec. 13, 1984.

Newmark et al., "Amygdalin (Laetrile) and prunasin beta-glucosidases: distribution in germ-free rat and in human tumor tissue," Proc. Natl. Acad. Sci. USA, vol. 78, No. 10, pp. 6513-6516, Oct. 1981.

Ninkovic and Hunt, "alpha-bungarotoxin binding sites on sensory neurones and their axonal transport in sensory afferents," Brain Research, 272 (1983) 57-69.

Nordberg and Larsson, "Studies of muscarinic and nicotinic binding sites in brain," Acta Physiol Scand, Suppl. 479: 19-23, 1980.

Noren et al., "A General Method for Site-Specific Incorporation of Unnatural Amino Acids into Proteins," Science, New Series, vol. 244, No. 4901 (Apr. 14, 1989), pp. 182-188.

Ohno et al., "Molecular evolution of snake toxins: Is the functional diversity of snake toxins associated with a mechanism of accelerated evolution?" Progress in Nucleic Acid Research and Molecular Biology, vol. 59, 1998.

Langer and Peppas, "Chemical and Physical Structure of Polymers as Carriers for Controlled Release of Bioactive Agents: A review," JMS-Rev. Macromol. Chem. Phys., C23(1), 61-126 (1983).

Picciotto et al., "Abnormal avoidance learning in mice lacking functional high-affinity nicotine receptor in the brain," Nature vol. 374, Mar. 2, 1995.

Rezvani and Levin, Cognitive Effects of Nicotine, Biol. Psych. 49, 258-67 (2001).

Picciotto et al., Nicotinic Receptors in the Brain: Links Between Molecular Biology and Behavior, Neuropsychophamacol. 22, 451-65 (2000).

Mason et al., The Hypogonadal Mouse: Reproductive Functions Restored by Gene Therapy, Science 234, 1372-78 (1996).

Lindstrom, Nicotinic Acetylcholine Receptors in Health and Disease, Mal. Neurobiol. 15, 193-222 (1997).

Damaj et al., Pharmacological Characterization of Nicotine-Induced Seizures in Mice, J. Pharmacol. Exp. Ther. 291, 1284-91 (1999).

Abrous et al., Nicotine Self-Administration Impairs Hippocampal Plasticity, J. Neurosci. 22, 3656-62 (2002).

Fonck et al., Increased Sensitivity to Agonist-Induced Seizures, Straub Tail, and Hippocampal Theta Rhythm in Knock-in Mice Carrying Hypersensitive alpha-4 Nicotinic Receptors, J. Neurosci. 23, 2582-90 (2003).

Fonck et al., Novel Seizure Phenotype and Sleep Disruptions in Knock-In Mice with Hypersensitive alpha-4 Nicotinic Receptors, J. Neurosci. 25, 11396-411 (2005).

Broide et al., Increased Sensitivity to Nicotine-Induced Seizures in Mice Expressing the L250T alpha-7 Nicotinic Acetylcholine Receptor Mutation, Mol. Pharmacol. 61, 695-705 (2002).

Orr-Urtreger et al., Mice Homozygous for the L250T Mutation in the alpha-7 Nicotinic Acetylcholine Receptor Show Increased Neuronal Apoptosis and Die Within 1 Day of Birth, J. Neurochem. 74, 2154-66 (2000).

Dani et al., Variations in desensitization of nicotinic acetylcholine receptors from hippocampus and midbrain dopamine areas, Eur. J. Pharmacol. 393, 31-38 (2000).

Wooltorton et al., Differential Desensitization and Distribution of Nicotinic Acetylcholine Receptor Subtypes in Midbrain Dopamine Areas, J. Neurosci. 23, 3176-85 (2003).

Kuryatov et al., Mutation Causing Autosomal Dominant Nocturnal Frontal Lobe Epilepsy Alters Ca2+ Permeability, Conductance, and Gating of Human alpha-4 beta-2 Nicotinic Acetylcholine Receptors, J. Neurosci. 17, 9035-47 (1997).

Miwa et al., lynx1, an Endogenous Toxin-like Modulator of Nicotinic Acetylcholine Receptors in the Mammalian CNS, Neuron 23, 105-14 (1999).

Ibanez-Tallon et al., Novel Modulation of Neuronal Nicotinic Acetylcholine Receptors by Association with the Endogenous Prototoxin lynx1, Neuron 33, 893-903 (2002).

Ibanez-Tallon et al., Tethering Naturally Occurring Peptide Toxins for Cell-Autonomous Modulation of Ion Channels and Receptors in Vivo, Neuron 43, 305-11 (2004).

Dessaud et al., Identification of lynx2, a novel member of the ly-6/neurotoxin superfamily, expressed in neuronal subpopulations during mouse development, Mol. Cell. Neurosci. 31, 232-42 (2006).

Readhead et al., Expression of a Myelin Basic Protein Gene in Transgenic Shiverer Mice: Correction of the Dysmyelinating Phenotype, Cell 48, 703-12 (1987).

Magram et al., Developmental regulation of a cloned adult beta-globin gene in transgenic mice, Nature 315, 338-40 (1985).

Ploug and Ellis, Structure-function relationships in the receptor for urokinase-type plasminogen activator and comparison to other members of the Ly-6 family and snake venom alpha neurotoxins, FEBS Left. 349, 163-68 (1994).

Adermann et al., Structural and phylogenetic characterization of human SLURP-1, the first secreted mammalian member of the Ly-6/uPAR protein superfamily, Protein Sci. 8, 810-19 (1999).

Arredondo et al., SLURP-2: A Novel Cholinergic Signaling Peptide in Human Mucocutaneous Epithelium, J. Cell Physiol. 208, 238-45 (2006).

Kawashima et al., Expression and function of genes encoding cholinergic components in murine immune cells, Life Sci. 80, 2314-19 (2007).

Kelsey et al., Species- and tissue-specific expression of human alpha-1 antitrypsin in transgenic mice, Genes Dev. 1, 161-71 (1987).

Krumlauf et al., Developmental Regulation of alpha-Fetoprotein Genes in Transgenic Mice, Mol Cell. Biol. 5, 1639-48 (1985).

Pinkert et al., An albumin enhancer located 10 kb upstream functions along with its promoter to direct efficient, liver-specific expression in transgenic mice, Genes Dev. 1, 268-76 (1987).

Miwa et al., The Prototoxin lynx1 Acts on Nicotinic Acetylcholine Receptors to Balance Neuronal Activity and Survival in Vivo, Neuron 51, 587-600 (2006).

Sandberg et al., New Chemical Descriptors Relevant for the Design of Biologically Active Peptides. A Multivariate Characterization of 87 Amino Acids, J. Med. Chem. 41, 2481-91 (1998).

Shani, Tissue-specific expression of rat myosin light-chain 2 gene in transgenic mice, Nature 314, 283-86 (1985).

Weis et al., Detection of rare mRNAs via quantitative RT-PCT, Trends Genet 8, 263-64 (1992).

Frohman, on Beyond Classic Race (Rapid Amplification of cDNA Ends), PCR Methods Appl. 4, S40-58 (1994).

Cale et al., Optimization of a Reverse Transcription-Polymerase Chain Reaction (RT-PCR) Mass Assay for Low-Abundance mRNA, Methods Mol. Biol. 105, 351-71 (1998).

Leder et al., Consequences of Widespread Deregulation of the c-myc Gene in Transgenic Mice: Multiple Neoplasms and Normal Development, Cell 45, 485-95 (1986).

Clemmons, IGF Binding Proteins and Their Functions, Mol. Reprod. Dev. 35, 368-74 (1993).

Loddick et al., Displacement of insulin-like growth factors from their binding proteins as a potential treatment for stroke, Proc. Nat'l Acad. Sci., U.S.A. 95, 1894-98 (1998).

Smith and Johnson, Single-step purification of polypeptides expressed in *Escherichia coli* as fusions with glutathione S-transferase, Gene 67, 31-40 (1988).

Hopp and Woods, Prediction of protein antigenic determinants from amino acid sequences, Proc. Nat'l Acad. Sci., U.S.A. 78, 3824 (1981).

Chou and Fasman, Prediction of Protein Conformation, Biochem. 13, 222-45 (1974).

Swift et al., Tissue-Specific Expression of the Rat Pancreatic Elastase I Gene in Transgenic Mice, Cell 38, 639-46 (1984).

Hanahan, Heritable formation of pancreatic beta-cell tumours in transgenic mice expressing recombinant insulin/simian virus 40 oncogenes, Nature 315, 115-22 (1985).

Grosschedl et al., Introduction of a mu Immunoglobulin Gene into the Mouse Germ Line: Specific Expression in Lymphoid Cells and Synthesis of Functional Antibody, Cell 38, 647-58 (1984).

* cited by examiner

FIG. 1

SEQ ID NO: 1

```
  1  TACCAACACC GCACGAAGTG TGTACAGATT CCCAGTTAGA CAGCAGGAGG
 51  GACCTGGGAG CGGCCAGGGG GATGTTTTAT CTCTAAGAGA CCAAGAGCTC
101  AGGCAGGGCT TCTGTGCCCT GCTTCCTCCC TGGCTTGAGC TGGATCCTGG
151  ACCAGCTGCT GACCTCCTGT TCACTCTGGC ACTGCCCTCA CGTCTCCGTC
```

```
        M   T   H   L   L   T   V   F   L   V   A   L   M   G   L   P   V
                                                            SEQ ID NO: 2
201  ATGACCCATC TGCTCACAGT GTTCCTGGTG GCCCTGATGG GCCTGCCTGT

A   Q   A   L   E   C   H   V   C   A   Y   N   G   D   N   C
251  GGCCCAGGCT CTGGAGTGCC ACGTGTGTGC CTACAATGGA GACAACTGCT

F   K   P   M   R   C   P   A   M   A   T   Y   C   M   T   T   R
301  TCAAACCCAT GCGCTGCCCA GCCATGGCCA CCTACTGTAT GACCACACGA

T   Y   F   T   P   Y   R   M   K   V   R   K   S   C   V   P   S
351  ACTTACTTCA CCCCATACCG GATGAAGGTG AGGAAGTCCT GTGTCCCCAG

C   F   E   T   V   Y   D   G   Y   S   K   H   A   S   A   T
401  CTGCTTTGAA ACCGTGTACG ATGGCTATTC CAAGCATGCA TCTGCCACCT

S   C   C   Q   Y   Y   L   C   N   G   A   G   F   A   T   P   V
451  CCTGTTGCCA GTACTACCTC TGCAACGGTG CTGGCTTTGC TACCCCGGTG

T   L   A   L   V   P   A   L   L   A   T   F   W   S   L   L
501  ACCTTGGCCC TGGTCCCAGC ACTCCTAGCT ACCTTCTGGA GCTTGCTGTA
```

```
 551  AAGCTCGGTT CCCCAAGCCA GATCCACTCA AACGCAACAC TCTCAAAAAA
 601  CACAGTTTCC CTCTCTCTCC CAATTCACTC CACCCAACGC TCTTCCTTCT
 651  GACACTCCTC AACTACCACG AGGTCCCATG GCTACCTACG AAAGAACTGA
 701  TGGCATCCAG ATACCTCACT CCAAGGTCAT TTTCAGAAGG CTGACATGTG
 751  GACCTGTAAT GTGCCCACCC ATGGGTGGGG CAGGCTGGGC TTCTCCTCTA
 801  CCCAAGATCA GGGGCATCTG GAGAATGTT  TATGGAGGAG GGTCATCAC
 851  TCAAGTCAAG GAGCACTGAT TGATAGAAT  TAGTAGCCAA ACTCCACCTT
 901  CAGAACCCTG CCTCAGTCTA CCCAGTAGAG GATGGGTCTG CTAGAGGTGA
 951  GGGGAGGAGA GCGGCGGAGA ATAACGAGCT GGCTAGAAGC AGAGAAAGAC
1001  TCAGCAGGGC TGTCTCCGAA GATCAGCGCG GCTTGCCAGA GCAAATGTGA
1051  TGTGGAAGCA ACGAGCTGGC TAGAAGCAGA GAAAGACTCA GCAGGGCTGT
1101  CTCCGAAGAT CAGCGCGGCT TGCCAGAGCA AATGTGATGT GGAAGCCATG
1151  TGAGGAAGCC CTTTGTCATT TCCACTTATC TGAGGAACTC TGCCAGACCT
1201  GATGTTGGGA TAGCCATTGG CCAAGGGTTC CTAGCAACGG CGTCATTTCC
```

(continued)

FIG. 1 SEQ ID NO.: 1 (continued)

```
1251   ATAGGCCACT GAAATCCCTC CAGCCCCAGC TCAGCAGGCC CCTTGACCTC
1301   CACTACAGTC CTTCATTCAC ACACCAGCTG CTGGGCCTTG AAGTTGGCAG
1351   GGACTTGGGA GCAGGTGACC CATGCTATTT TTTGTCTGGC CTGTTATTCT
1401   GGGCATGGCA AGAAGGGATC AGACGCAGGT CAGAGCAGGG CAGTAGGGCG
1451   ACTGAGACAG GGAAACAGAC TTCAGCCAGT GGCTTCCAG GTCCCGTAGG
1501   CAGCTCCTAC ATCCTTCAGT CTCTTGTTAC ATTCCCGGGA GACAAATATA
1551   CAGGGAGCCA AGCCGAGTGC TAGGTGATGA CTGCCTGTGA AGTCTATTGT
1601   GGCCACAGAC TGCTGGGTAC CAAGTCTCAG GAGAACCCAG CCTAGATTTA
1651   GGAGACACAG ATCTGCCTTT CATGCAGTGT AGCTGTCCTT GGGAGCCTTA
1701   CCATGCTCTC TAACTAGTTC CTCAACTCAC ATGTCACTGA GGAACCCCCT
1751   AACACTGGCC CAGCCCAGGG GTCGGATGC TGGCCAATGT CCATGGAGTG
1801   GGACTACCCC TGGAGAGTCC TTGGGTCATC ACATCACAAA TGTTTTATTC
1851   CAACCTCCCA GTGGTGAGAG CTCGGACAC AAAGGTCCAT CCTGGGGACC
1901   TTCTTCCTGG TTCTAGGCAG ACCTGAACTC TGTCTGCTGC TAGAGCTGAT
1951   GTGGTTTTCC GCCTCAGTTT CCTCCTCCGG GGATAGGCCA CCGGAGGATT
2001   TGGGAGGGTG GGGAGGGCAT CCTGCTGATG GGCTCGCCGA GGTTCTCAGG
2051   AACAGGAACG GGCGGGGCTT TAGTACACAG GTGAGTTGGG TGGGAACTGG
2101   CCCGGAGCTG AGGAGACACT GACTGGGCAG AGGGAAGATG AGTCTCAAGG
2151   GAGGGCAGGA AAAGGGAGGG GGAGCGCGCA TGCACATGTG CACTCAGTGC
2201   AGGCTACAGA GCCCAAAAGG CAGCACTGGC TGTGGTGTCC CCTGAGGCCC
2251   AGGCAAGATG CTAGGAGGAA GCCAATGCTG CCCCCACCTG AGCTCACATG
2301   GAACATGCAC ACCACCAGCA GCAGCAGCAA GCATTGAGAC TGACCTGTGG
2351   ACGCCATAGG GCACTGGCAA GGAGGGTCAG AGGCGGGTCC CTGACTCAGT
2401   GGGTGAGGCC CGGGAAACAT TATCCTGTTA CCCTGCGTGT GCAAGATCAT
2451   TGTCCCCAGC TAGATGGCGT CCTCAACCAA AACTGAGAGG AGCCCCAGTT
2501   CAGGTCCTCC CTCCTACCAC AAGGGGGTGG TGTGGAGGAG GCTTGATTGC
2551   CCTTGGAGAA GCACCGGTAC TGCAGAGCTG GGGGCCAGCT TCTTTCATCT
2601   GTGTCTAGAC ACCGACCAGA TAGGCCCCAC AGTGGCAACA CTGCCACACA
2651   GTCCTACAAG AAGCCCTGTG CCTAGCTAGC ACAGAGCCCC AAAAGGTGCT
2701   CAATTAATAC AGGGCAAGC CTGCCAGTGG GGGGGATGCA GATTAGGGGA
2751   ACAGACCCAG ATGGCCTGTC CTGAACCCTG TCTGGGGTGG TGTGATGAGC
2801   ATCTGTCTAG CCCACTGCAG GTGGCTCTAC ACACTCCACA ACAGTTCTGC
2851   AAAAGTGTAT GAGGTGGTCA TTACTGCGCC CCTCTCACAG GTAAAGGCAC
2901   TGAGGCACGG AGGAGTGAGG CACTTCATTT TCCTGGGCCA TTCAACTTTC
2951   CAGGACCAAC ACATTCAACT ATGGGTACTA CTCCAATAGC TGGGGTTCTT
3001   TGAGGCTGGG CCCCCTGAAG ATGATAGTGG CTTCATCAAC CAGAGAATTT
3051   CAGAGTGCAG TGTTGTAGGA GCCTATGAAC CTGAAATGTC AGAACTGGAG
3101   GTTTGAGGGG CTGAGGGGTA GGCCAGGGGT GTCTGGCCCC TTGTGTGGAG
3151   ACAGAGAGAG AGGGAACATG GGATGGGTA GTAGAGAGAA GTGCAAAGGA
3201   GCGTCAGCCT TTCTCAGGGC TAATGCTGTC AGGGACGAGG GCTCAAGCCT
3251   GTGAGTGTTC TCACACTGTG ATAAACAGTG GCCCCTCAAC ACAGACGGTG
3301   TCCAGAGTGG CCGGCAGTGG TTATCTAGAG TTGCAATCTG GAAGCCTCTT
3351   GGTAGTCACT GGAGAGAGGC CGCTTGATGG GACAGCACCA AATGTGTGTG
3401   CTTCTGTGGG ATGTGAGGAA GCTGGGTCAG CGCATGAAGC CAAAGCGTCC
3451   TTCAGAGCAG AGGGGTGGCT GGTCTAGTCC ACCAGAGACA AGCTATCCAG
3501   TGAGAGTCAT ACTCTGTCAC CGTCTCTGTG ATTACCTTAC CCCAAAGCAG
```

(continued)

FIG. 1  SEQ ID NO.: 1 (continued)

```
3551  ACGGGGACGG GATGCAGAGC ACCCGTGTCT TCATCTTCTG CGGCAAGCAC
3601  GTGAGTTCAC ATTCTGAAAC TCTAGAAAGA TTTCCAGGAG TGGGGTGTGC
3651  CTTTGCTTTG GTGCATGGTT ACTTCCTGGC AAGCACCGTG GCATCCCGCA
3701  GCACTGAGTG ACCTGGGCTC CTCAAGCCAT CTCATTGGTG AAATGACAGT
3751  GCCAGTACCC TCTCAGCTGG CTCTTGGAGG CCTGTGCATG GGGTCTGCAC
3801  AGAGGAGGCC CCCAAACTAT GCATGGACGG ACACGTGATG CCTAGCACTT
3851  CCCTTGGTTG TGTCTCTGCC AACCCCAGGC TCTCACCCAG CAAGGAAATG
3901  AAATCCACTT TTATGACACA TCTCCTCCC CCAGCCAGCT CCATTCACCT
3951  ATATGCCAGG GTGGTCCCTT TCAATGTCTG TCCCCCATTG GATGAATAAA
4001  CAAGCGAAGG ACAAAAAAAA AAAAAAAAA A
```

FIG. 2A

MTHLLTVELVALMGLPVAQALECHVCAYNGDNCFKPMRCPAMATYCMTTRTYFTPYRM
KVRKSCVPSCFETVYDGYSKHASATSCCQYYLCNGAGFATPVTLALVPALLATFWSLLL    SEQ ID NO.: 2

FIG. 2B

```
            C                C       C                      C          C           CC       CN
(1) lynx1   LECHVCAYNGDN     CFKPMRCPAMATYCMTTRTYFTPYRM     KV RKSCVP  SCFETVYDG   YSKHASATSCCQYYLCN
(2) E48     LRCHVCTSSSN      CKHSVVCPASSRFCKTNTVEPLRGN      LVK KDCAE  SCTPSYTLQGQ VSSGTSSTQCCQEDLCN
(3) Ly-6A/E LECYQCYGVPFETSCPS ITCYPYDGVCVTQEAAVIVDSQTRKVKNNLCL          PICPPNIESMEILGTKVNVKTSCCQEDLCN
(4) CD59    LTCYHCFQPVVS     SCNMNSTCSPDQDSCLYAVAGMQVYQ     RCWKQSDCHGEII MDQLEETK LKFRCCQFNLCN
(5) αCbtx   LECHNQQSSQ       TPTTTGCSGGETNCYKKRWRDHRGYR     TERGC       GCPS        VANGIEINCCTTDRCN
(6) αBgtx   IVCHTTATSP       ISAVTCPPGENLCYRKMWCDAFCSSRGKVVELGCAA     TCPS        KKPYEEVTCCSTKDCN
(7) M3tx    LTCVTSKSIF       GITTENCPAGQNLCFKRRHYVIPRYT     EITRGCAA    TCPI        PENYDSIHCCKTDRCN
```

(1) SEQ ID NO.: 2
(2) SEQ ID NO.: 19
(3) SEQ ID NO.: 20
(4) SEQ ID NO.: 21
(5) SEQ ID NO.: 22
(6) SEQ ID NO.: 23
(7) SEQ ID NO.: 24

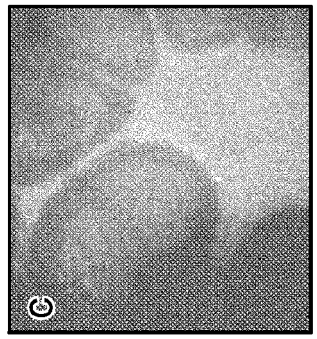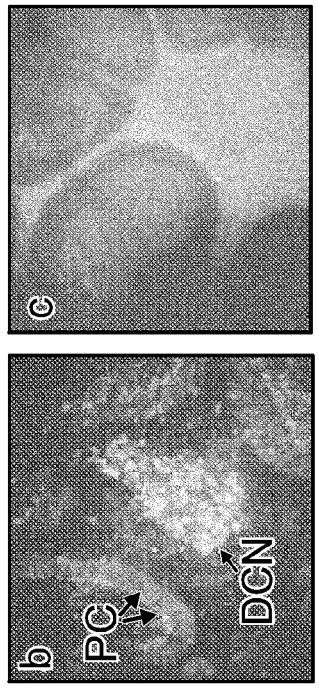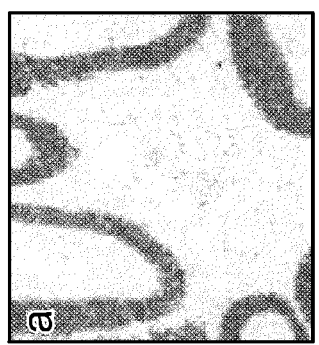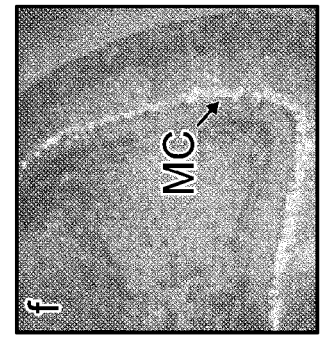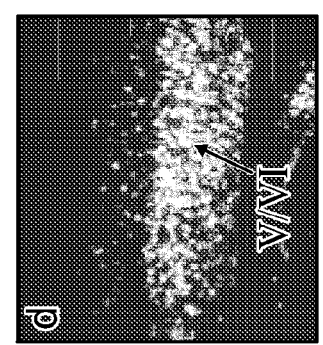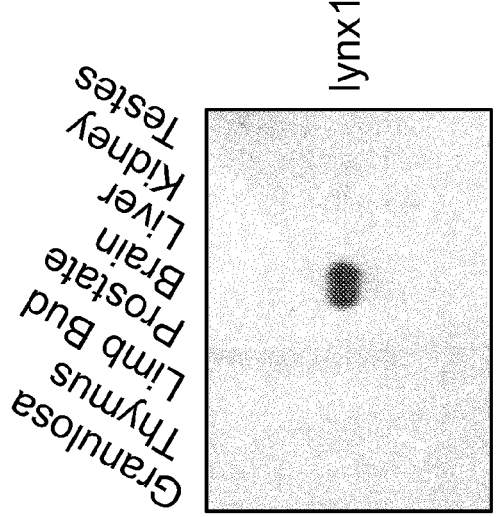

FIG. 6A

| Averages | Day 1 | Day 2 | Day 3 | Day 4 | Day 5 | |
|---|---|---|---|---|---|---|
| WT | 19 | 22.9 | 20.6 | 15.6 | 17.9 | sec | n=6 |
| Tg | 20.9 | 28.3 | 28.8 | 27.4 | 27.4 | sec | n=6 |
| % inc | 10 | 23.58079 | 39.80583 | 75.64103 | 53.07263 | |

| | | | | | p value |
|---|---|---|---|---|---|
| SEM | 2.5 | 1.9 | 2 | 2.1 | 1.7 |
| SEM | 1.8 | 2.1 | 3.4 | 3.2 | 2 | 10 E-08 |

FIG. 7

```
LOCUS AA139375      SEQ ID NO.: 5
  1 gtgagcccgg gaaacattat cctgttaccc tgcgtgtgca agatcattgt cccagctag
 61 atggcgtcct caaccaaaac tgagaggagc cccagttcag gtcctccctc ctaccacag
121 gggtgtgt ggaggagct tgattgccct tggagaagca ccggtactgc agagctgggg
181 gccagcttct ttcatctgtg tctagacacc gacccacagt gcccacaaa ggcaacactg
241 ccacacagcc ctacacagaag ccctgtgcct agctagcaca gagcccaaa aggtgctcaa
301 ttaatacagg gccaagcctg ccagtggggg ggatgcagat taggggaaca gacccagatg
361 gcctgtcctg aacctgtct ggggtggtgt gatgagcatc tgtctagccc actgcaggtg
421 gctctacaca ctccacaaca gttctgcaaa agtgtatgag gtggtcatta ctg LOCUS AA268004      SEQ ID NO.: 7
  1 gtgggatgtg aggaagctgg gtcagcgcat gaagccaaag cgtccttcag agcagagggg
 61 tggctggtct agtccaccag agacaagcta tccagtgaga gtcatactct gccaccgtct
121 ctgtgattac cttacccccaa agcagacggg gacgggatgc agacacccgt gtcttcatct
181 tctgcggcaa cacgtgagtt cacattctga aactctagaa agatttccag gagtgggtg
241 tgcctttgct ttggtgcatg gttacttcct ggcaagcacc gtgcatccc gcagcactga
301 gtgacctggg ctcctcaagc catctcattg gtgaaatgac agtgccagta ccctctcagc
361 tggctcttgg aggcctgtgc atgggtctg cacagaggag LOCUS AA619349      SEQ ID NO.: 9
  1 attcggatcc ttgtgcgatg cggtaccaac accgcacgaa gtgtgtacag attcccagtt
 61 agacagcagg agggacctgg gagcggccag ggggatgttt tatctctaag agaccaagag
121 ctcaggcagg gcttctgtgc cctgcttcct ccctggcttg agctggatcc tggaccagct
181 gctgacctcc tgttcactct tggcactgct cacgtctccg tcatgaccca tctgctcaca
241 gtgttcctgg tggccctgat ggctgcctgt ggccaggctc tggccgcca cgtgtgtgcc
301 tacaatggag acaactgctt caaacccatg cgctgccac cactgtatg ctactgtatg
361 accacacgaa cttacttcac cccataccgg atgaaggtga ggaagtcctg tgtccccagc
421 tgctttgaaa ccgtg
```

FIG. 7
(continued)

```
LOCUS AA711715      SEQ ID NO.: 8
  1 ttcggatcct tgctgcgccc tctcacaggt aaaggcactg aggcacggag gagtgaggca
 61 cttcattttc ctggccatt caactttcca ggaccaacac attcaactat gggtactact
121 ccaatagctg gggttctttg agctggggc cctgaagat LOCUS AA929210      SEQ ID NO.: 6
  1 tgaaatgtca gaactggagg tttgaggggc tgaggggtag gccagggggtg tctgcccctt
 61 gtgtggagac agagagagag gggaacatgg ggaaacatgg atggggtagt agagagaagt gcaaaggagc
121 gtcagctttc tcaggctaa tgctgtcagg gacgagggct caagctgtga gtgttctcac
181 actgtgataa acagtggccc ctcaaacacag acggtgtcca gagtggccgg cagtggttat
241 ctagagttgc aatctggaag cctcttggta gtcactggag agaggccgct tgatgggaca
301 gcaccaaatg tgtgtgcttc tgtgggatgt gaggaagctg ggtcagcgca tgaagccaaa
361 gcgtccttca gagcagaggg gtggctggtc tagtccacca gagacaagct atc LOCUS H19490        SEQ ID NO.: 11
  1 gatgggtttt tntaggtgga cgcgtgcttg gagtagccat catacacagt ctcgaagcag
 61 cggggcacgc aggantact gaccttcatc ctggtggggg tntagtaggt gcgcgtggtc
121 atgcagtagg caaccatagc cgggcagcgc atggggttga agcagttntc tccgttntag
181 gcacacacgt gggcagtcca aggcctgggg ccagaggtaa gcccatgagg accaccaggg
241 ntcagggtna gcaggggcnt catggctgca ggcaggaggg cagcntggg
```

FIG. 7 (continued)

```
LOCUS H19572     SEQ ID NO.: 12
  1 nattcggcac gaaggctgcc gcgggacggn anangatagc ctgcgagtgt ccgggcggaa
 61 cacggttgca gcattcccag tagaccagga gctccgggag gcagggccgn cccacgtcc
121 tctgcgcacc acctgagtt ggatcctctg tgcgccaccc ctgagttgga tccaggcta
181 gctgctgttg acctcccac tcccacgctg ccctcctgcc tgcagccatg acgcccctgc
241 tcaccctgat cctggtgtc ctcatggct ctacctctgc ccagggcttg gactgccacg
301 tgtgtgccta caacgagac aactgcttca accccatggc gctgcccggc tatggtttgc
361 tgattgcnat ggaccaaggn ggaantgatt a LOCUS H46195     SEQ ID NO.: 13
  1 atttcggcac gaaggctngc cgcggggcga anangnatag cctgcgnagt gtccgggcgg
 61 aacacggttg cagcactccc agtagaccag gagctccggg aggcaggcg ncccacgtc
121 ctctgcgcac caccctgagt tggatcctct gtgcgccacc cctgagttgg atccaggct
181 agctgctgtt gacctcccca ctcccacgct gccctcctgc ctgcagccat gacgccctg
241 ctcaccctga tcctggtgg tcctcatggg cttacctctg ggcccaggge ttggactgc
301 cacgtgtgtg cctaacaaac ggagacaant gcttcaaccc catggcgctg cccggctatg
361 gttgcnaat tgcatggacc aagggcacn tattacaacc cccaccaggg atgaaaggtn
421 agtaaagtt LOCUS H46196     SEQ ID NO.: 10
  1 gtgcttggag tagccatcat acacagtctc gaagcagcgg ggcacgcagg acttactgac
 61 cttcatcctg gngggggtgt agtaggtgcg cgtggtcatg cagtaggcaa ccatagccgg
121 gcagcgcatg gggttgaagc agttgtctcc gttgtaggca cacacgtggc agtccaaggc
181 ctgggcagag gtaagcccat gaggaccacc aggatcaggg tgcaggggg cgtcatggct
241 gcaggcagga gggcagcgtg ggagtgggga ggtcaacagc agctagccct gggatccaac
301 tcaggggtgg cgcacagagg atccaacttc agggtggttg cgcagaggac gtgggggccg
361 gccctgcctt cccggagctc c
```

FIG. 8

SEQ ID NO.: 14

```
NGAAAGGTTTCCNGAATGGGAAAGGGGGGCAGGGGGGCAAAGGAATTTAWTGGGTAADG    60
GCWGGTTTTTCCCARTTCAAGGAGTTGTAAAKGAGGGCCAGGGATTGTAATAGGARTTA   120
ATTRTGAGGGAGAAATTGGGTACGGGCCCCMCTTKRDGTYGGAYGGTATCSATWAGGCTC  180
TGATATSGAATTCCCCCTCCTABTCGTCGCGRCGTMGCGTMCGMGGGTTACTCCCAGGCG  240
CGGYGGTACCTCACGGTGGTGAAGGTCACAGGGTTGCAGCAYTCCCAGTAGACCAGGAGC  300
TCCGGGAAGGCAGGGCCGGCCCCACGTCCTCTGCCACCACCCTGAGTTGGATCCTCTGT   360
GCGCCACCCCTGAGTTGGATCCAGGGCTAGCCTGCTGTTGACCTCCCCACTCCCACGCTGC 420
CCTCCTGCCTGCAGCCATGACGCCCCCTGCTCACCCTGATCCTGGTGGTCCTCATGGGCTT 480
```

SEQ ID NO.: 15

```
            M  T  P  P  L  L  T  L  I  I  L  V  V  L  M  G  L

ACCTCTGGCCCAGGCCTTGGACTGCCACGTGTGTGCCTACAACGGAGACAACTGCTTCAA   540

```
                                                                                SEQ ID NO.: 14 (continued)
CCCCATGCGCTGCCCGGCTATGGTTGCCTACTGCATGACCACGCGCACCTAYTACACCCC   600
 P  M  R  C  P  A  M  V  A  Y  C  M  T  T  R  T  Y  Y  T  P
                                                                                SEQ ID NO.: 15 (continued)
CACCAGGATGAARGTCAGTAAGTCCTGCGTGCCCCGCTGCTTCGAGACTGTGTATGATGG   660
 T  R  M  K  V  S  K  S  C  V  P  R  C  F  E  T  V  Y  D  G CTACTCCAAGCACGCGTCCACCACCTCCTGCCAGTACGAACTCTGCAACGGACCGGC     720
 Y  S  K  H  A  S  T  T  S  C  C  Q  Y  E  L  C  N
              ↑
CTTGCCACC   729
```

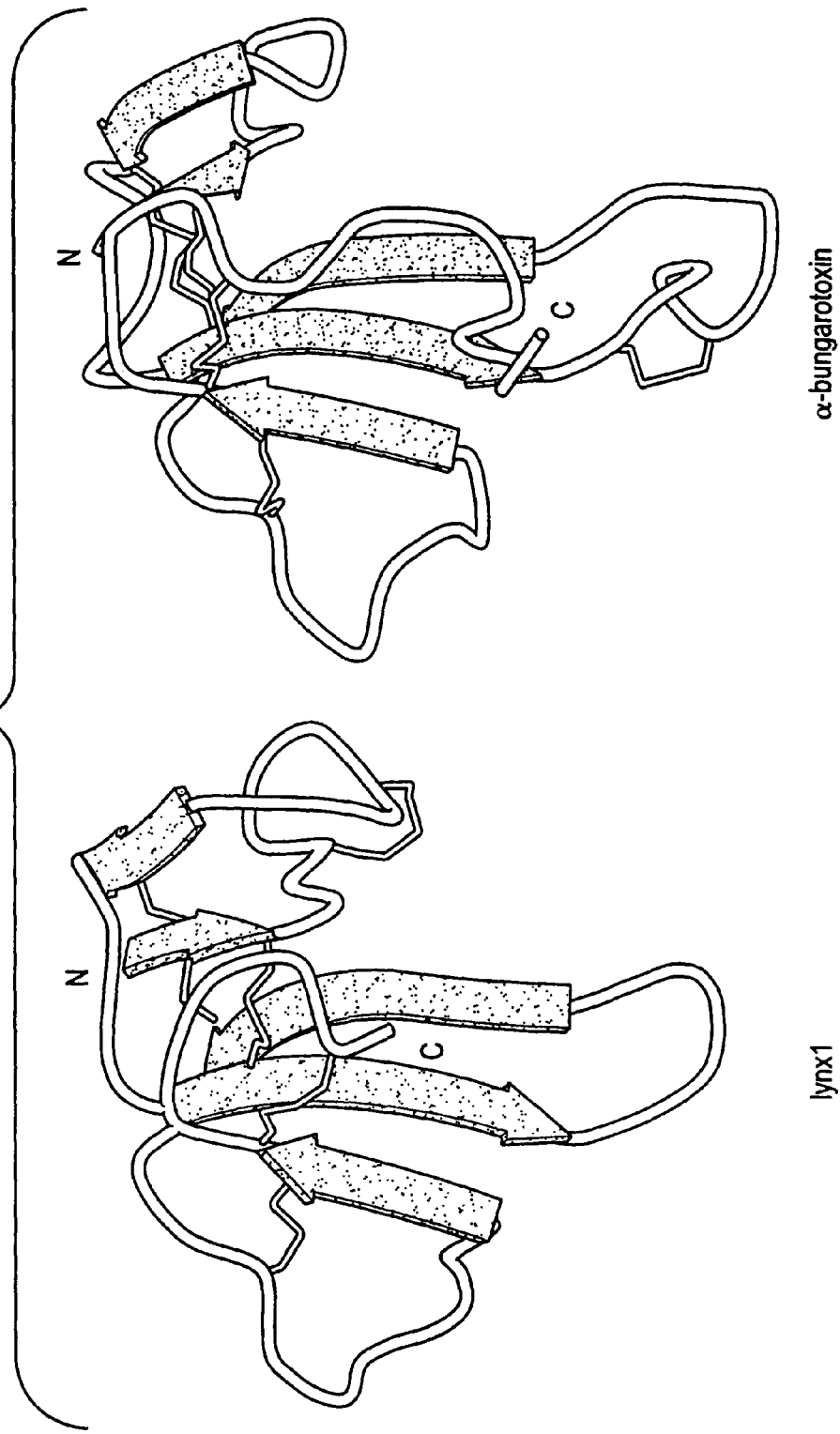

LYNX POLYPEPTIDES

RELATED APPLICATIONS

The present application is a continuation of Ser. No. 09/320,864 filed May 27, 1999, now abandoned, which is a continuation-in-part of Ser. No. 09/156,926 filed Sep. 18, 1998, now abandoned, each of which the instant application claims the benefit of the filing date pursuant to 35 U.S.C. §120, and which are incorporated herein by reference.

FIELD OF THE INVENTION

The present invention relates generally to novel family of polypeptides which are ligand-gated channel receptor accessory molecules or ligands, denoted Lynx, and to nucleic acids encoding such polypeptides. The invention also relates to diagnostic, therapeutic and pharmaceutical compositions and uses of such polypeptides, analogs and fragments thereof, and nucleic acids encoding such polypeptides, analogs and fragments thereof, and to antibodies of such polypeptide and the use of such antibodies.

BACKGROUND OF THE INVENTION

Ligand-gated ion channels represent a large, evolutionarily related group of intrinsic membrane proteins that form multisubunit complexes and transduce the binding of small agonists into transient openings of ion channels. Neurotransmitters bind to these channels externally, causing a change in their conformation, allowing ions to cross the membrane and thereby alter the membrane potential. The receptors which comprise these channels have an enzyme-like specificity for particular ligands (the neurotransmitters) and are characterized by their ion selectivities, including permeability to Na+, K+, Cl-, etc. Recognized neurotransmitters include acetylcholine, dopamine, serotonin, epinephrine, gamma-aminobutyrate (GABA), glutamate and glycine, each recognized by distinct receptors. The super-family of ligand-gated channels includes the nicotinic acetylcholine receptor (nAChR), the serotonin receptor the GABA receptor, and glutamate receptors.

Neurotransmitters are synthesized in brain neurons and stored in vesicles. Upon a nerve impulse, a neurotransmitter is released into the synaptic cleft, where it interacts with various postsynaptic receptors. The actions of neurotransmitters, such as acetylcholine and serotonin, are terminated by three major mechanisms: diffusion; metabolism; and uptake back into the synaptic cleft through the actions of membrane transporter systems. Thus, the actions of any such neurotransmitter can be theoretically modulated by: agents that stimulate or inhibit its biosynthesis; agents that block its storage; agents that stimulate or inhibit its release; agents that mimic or inhibit its actions at its various postsynaptic receptors; agents that inhibit its uptake back into the nerve terminal; and agents that affect its metabolism.

The acetylcholine receptor (AChR) is divided into two main types, muscarinic and nicotinic, based on the fact that the two poisons nicotine (from tobacco), and muscarine (from mushrooms) mimic the effect of acetylcholine on different types of receptors. The muscarinic AChR is found on smooth muscle, cardiac muscle, endocrine glands and the central nervous system (CNS). The nicotinic AChR (nAChR) is located on skeletal muscle, ganglia and the CNS, mediating synaptic transmission at the neuromuscular junction, in peripheral autonomic ganglia, and in the CNS.

Nicotinic acetylcholine receptors are glycosylated multisubunit pentamers. Six different types of subunit have been identified—alpha, beta, gamma, sigma, delta and epsilon—each of molecular weight 40-60 kDa. The pentamer is made up of different combinations of the subunits. The five subunits form a ring which spans the plasmamembrane of the postsynaptic cell, creating a channel. Within each subunit type, distinct subtypes have been identified, including multiple alpha subunits ($\alpha1$-$\alpha9$) and beta subunits ($\beta2$-$\beta4$) with related but unique sequences (Role and Berg (1996) *Neuron* 16, 1077-1085). The binding of acetylcholine or nicotine to the alpha subunit of the receptor induces a conformational change which allows the influx of sodium and calcium into the cell. The synaptic action of acetylcholine on the receptor is terminated by enzymatic cleavage by acetylcholinesterase.

Antagonists with relative specificity for the nAChR include tubocurarine and the snake venom-derived neurotoxins such as bungarotoxin (aBTX) and cobratoxin (Schlyer, B. D. et al (1992) *FEBS Lett.* 297, 87-90). The snake venom alpha-neurotoxins such as alpha-bungarotoxin (aBTX) competitively block or occlude the binding of agonists to the muscle-type acetylcholine receptor. Alpha conotoxins, isolated from conus venom, and designated alpha because they have the same action as the alpha neurotoxins from snake venoms (eg. aBTX) at the nicotinic receptor. Like aBTX, alpha conotoxins cause postsynaptic inhibition at the neuromuscular junction resulting in paralysis and death. The symptoms resemble those of curare poisoning with eventual respiratory failure. The mechanism by which paralysis is brought about by these and similar such toxins (e.g. curare, Botulinum toxin) is through binding to the alpha subunit of the nicotinic ligand-gated ion channel and blocking the binding of acetylcholine and of agonists such as nicotine. By preventing the agonist-induced conformational change in the receptor ion channel required for the influx of sodium that is essential for membrane depolarisation, theses toxins inhibit neurotransmitter secretion and induce paralysis.

CNS therapeutic applications for the acetylcholine receptors include cholinometic approaches in the treatment of Alzheimer's disease and anticholinergic drugs in the treatment of Parkinson's disease. Nicotinic cholinoceptive dysfunction associated with cognitive impairment is a leading neurochemical feature of the senile dementia of the Alzheimer type. For this reason, nicotinic acetylcholine receptors have attracted considerable interest as potential therapeutic targets in Alzheimer's disease. Nicotinic acetylcholine receptors have also been implicated as potential therapeutic targets in other memory, learning and cognitive disorders and deficits, including Lewy Body dementia and attention deficit disorder. In addition, the alpha subunit of nAChR has been recognized as playing an important role in the etiology of congenital myasthenia syndromes and stimulates T cells in patients with auto-immune mediated myasthenia gravis (Croxen, R. et al., (1997) *Hum Mol Genet.* 6, 767-774; Sine, S. M. et al., (1995) *Neuron* 15, 229-239, Katz-Levy, Y. et al., (1998) *J. Neuroimmunol* 85, 78-86).

Located primarily in peripheral and central neurons, serotonin (5-hydroxytryptamine, 5-HT) receptors appear to be involved in the depolarization of peripheral neurons, pain, and the emesis reflex. Potential use of agents acting at this site include migraine, anxiety, substance abuse, and cognitive and psychotic disorders. There are at least four populations of receptors for serotonin: 5-HT1, 5-HT2, 5-HT3, and 5-HT4. Recent cloning studies suggest the existence of 5-HT5, 5-HT6, and 5-HT7 subtypes as well. In addition at least five distinct subtypes of the 5-HT2 and three subtypes of the 5-HT3 receptors exist. Largely due to the complexity of these multiple subtypes, the physiological function of each receptor subtype has not been fully established. With the exception of the 5-HT3 receptor, which is a ligand-gated ion channel related to NMDA, GABA and nicotinic receptors, all of the 5-HT receptor subtypes belong to the group of G-protein linked receptors.

Serotonin is implicated in the etiology or treatment of various disorders, including anxiety, depression, obsessive-compulsive disorder, schizophrenia, stroke, obesity, pain, hypertension, vascular disorders, migraine, and nausea. 5-HT is synthesized in situ from tryptophan through the actions of the enzymes tryptophan hydroxylase and aromatic L-amino acid decarboxylase. Both dietary and endogenous 5-HT are rapidly metabolized and inactivated by monoamine oxidase and aldehyde dehydrogenase to the major metabolite, 5-hydroxyindoleacetic acid (5-HIAA). The major mechanism by which the action of serotonin is terminated is by uptake through presynaptic membranes. After 5-HT acts on its various postsynaptic receptors, it is removed from the synaptic cleft back into the nerve terminal through an uptake mechanism involving a specific membrane transporter in a manner similar to that of other biogenic amines. Agents that selectively inhibit this uptake increase the concentration of 5-HT at the postsynaptic receptors and have been found to be quite useful in treating various psychiatric disorders, particularly depression. Selective 5-HT reuptake inhibitors (SSRIs) have been investigated as potential antidepressants with the anticipation that these agents would possess fewer side effects, such as anticholinergic actions and cardiotoxicity, and would be less likely to cause sedation and weight gain. Three selective 5-HT uptake inhibitors, have more recently been introduced on the U.S. market, Fluoxetine (Prozac), sertraline (Zoloft), and paroxetine (Paxil) and have gained immediate acceptance, each listed among the top 200 prescription drugs. In addition to treating depression, several other potential therapeutic applications for SSRIs have been investigated. They include treatment of Alzheimer's disease; modulation of aggressive behavior; treatment of premenstrual syndrome, diabetic neuropathy, and chronic pain; and suppression of alcohol intake. Also significant is the observation that 5-HT reduces food consumption by increasing meal-induced satiety and reducing hunger, thus, there is interest in the possible use of SSRIs in the treatment of obesity.

5-HT3 receptors have been proposed to play a major role in the physiology of emesis. These receptors are found in high concentrations peripherally in the gut and centrally in the cortical and limbic regions and in or near the chemoreceptor trigger zone, and have been implicated in the vomiting reflex induced by serotonin as a result of chemotherapy. Two 5-HT3 receptor antagonists, ondansetron (zofran) and granisetron (Kytril), have been marketed to treat nausea associated with radiation and chemotherapy in cancer patients.

The Ly-6 proteins were first discovered serologically as specific antigens expressed on the surface of developing lymphocytes. Monoclonal antibodies to these proteins activate T-lymphocytes, which suggest a role for these proteins in signal transduction and cellular activation (Malek et al. (1986) *J. Exp. Med.* 164, 709-722; Rock et al (1986) *J. Exp. Med.* 163,). This points to the role of the Ly-6 proteins as accessory molecules to T cell receptor (TCR) function. Accessory molecules on T cells specifically bind other molecules (ligands) present on the surface of other cells such as antigen presenting cells (APCs). Accessory molecules increase the strength of adhesion between a T cell and an APC or target cell. The importance of accessory molecules in T cell activation is suggested by the fact that antibodies against these molecules can block T cell responses to antigens. When TCR binds an activating ligand, a signal is generated that leads to a marked increase in the avidity with which the T cell accessory molecules bind to their ligands on the APCs. Thus, Ly-6 proteins are implicated as mediating, if not being essential to, the action and activity of the T cell receptor.

The Ly-6 family is represented by a wide variety of genes from numerous species, all with structural and evolutionary homology. They are classified together based on a common cysteine rich motif Members of this superfamily include: the Ly-6 genes, of which up to 20 have been identified and eight cloned; CD59, a complement inhibitory molecule which has been cloned from almost a dozen species; Thymocyte B cell antigen (ThB); Thymic shared antigen, (TSA-1); urokinase plasminogen activator receptor (uPAR); retinoic acid induced gene (RIG-E) from human; alpha-bungarotoxin (aBTX) from elapid snakes; and squid glycoprotein-2 from squid. The EGF receptor is a distant family member of this family.

The Ly-6 family is defined by the existence of a cysteine-rich motif spanning the length of the mature encoded proteins which participates in a pattern of disulfide bonding responsible for its overall topology and a conserved similar three dimensional structure. Two crystal structures of the Ly-6 family members have been solved, aBTX and CD59 (Love and Stroud (1986) *Protein Engineering* 1, 37-46; Fletcher et al (1994) *Structure* 2, 185-199). The folding topology of CD59 is similar to snake toxins, with three loops extending from a rigid central core. The structure of alpha bungarotoxin is very similar to other snake toxins whose structure has been solved and is termed the three fingered toxin fold (Rees et al (1987) *Proc. Natl. Acad. Sci.* 84, 3132-3136). The Ly-6 family of genes encode small cell surface proteins, which are bound to the external face of the plasma membrane by a glycosylphosphatidylinositol (GPI)-linkage. These proteins are probably evolutionarily related because they are usually four exon genes, with a remarkable degree of conservation in the gene structure. In addition, most of the Ly-6 gene family members are genetically linked in the mouse genome, and the human homologs map to an evolutionarily related, syntenic, region in the human genome.

The snake toxin alpha-bungarotoxin (aBTX) has long been known to bind in the brain with high affinity (Clarke et al (1985) *J. of Neuroscience* 5, 1307-1315). It was long thought that aBTX bound primarily to acetycholine receptors, but careful analysis reveals non cholinergic binding sites, which have yet to be accounted for aBTX, as well as other snake toxins, block nicotinic cholinergic neurotransmission at the neuromuscular junction and bind to rat membranes at high affinity (Speth et al (1977) *Brain Res.* 131, 350-355; Nordberg and Larsson (1980) *Acta Physiologica Scandinavia Suppl.* 479, 19-23). Binding of [125I]-aBTX is saturable and reversible and is displaced preferentially by nicotine agents, hence the displacement potency of nicotine in vitro suggests that nicotine could act as a aBTX site in vivo (Harfstrand et al (1988) *Acta Physiologica Scandinavia* 132, 1-14). More recently however, the use of aBTX as a general probe for the nicotinic-cholinergic receptor in the mammalian CNS has been widely questioned. For example, Marks and Collins (Marks and Collins (1982) *Molecular Pharmacol.* 22, 554-556), found a lack of correlation between the regional distributions of nicotine and aBTX binding in the mouse brain (Del Toro et al (1994) *JCN* 349, 325-342). Schwartz et al compared nicotinic Ach binding and aBTX binding in rat brain and reached the same conclusion (Schwartz et al (1982) *Molecular Pharmacol.* 22, 55-62). In addition, in the CNS, aBTX can bind extrasynapically (Ninkovic and Hunt (1983) *Brain Research* 272, 57-69). aBTX fails to block nicotinic cholinergic transmission at Renshaw cells (Duggen et al (1976) *Brain Research* 107, 166-170). In the hippocampus, aBTX binds to certain areas which lack cholnergic innervation (Hunt and Schmidt (1979) *Neuroscience* 4, 585-592). In the rat, the superior colliculus is densely labeled by aBTX but a chlotinergic input from the retina does not exist. Single unit recordings in the interpedunclular nucleus is a structure with a high density of nicotine binding but low level of aBTX binding; excitation was great with Ach or carbachol and ineffective with aBTX (Brown et al (1983) *J. of Physiol.* (London) 341, 655-670). A quantitative displacement study confirms that nicotine and Ach displace aBTX binding only at micromolar concentration (3-30 uM), different than the nanomolar ranges used for the agonist binding experiments (1 nM), and aBTX displacement experiments (Clarke et al (1985) *J. of Neuroscience* 5, 1307-1315)). In other studies, it is seen that high levels of aBTX is required to displace the high affinity binding of nicotine or Ach to brain tissue (Romano and Goldstein (1980) *Science* 210, 647-650); Marks and Collins (1982) *Molecular Pharmacol.* 22, 554-556); Schwartz et al (1982) *Molecular Pharmacol.* 22, 55-62; Hayashi et al (1984) *J. of Neurochem.* 42, 203-209); Schoepfer et al (1990) *Neuron* 5, 35-48). Alpha-bungarotoxin has been shown to bind to and inhibit certain of the alpha subunits of the nAChR, specifically alpha 1, alpha 7, alpha 8 and alpha 9 (Changeux et al (1998) *Brain Res Rev* 26, 198-216).

The physiological relevance of toxin action rests on the idea that these molecules have evolved from endogenous genes operating in normal cellular pathways (Ohno et al., (1998) *Prog Nucl Acid Res* 59, 307-364). Functional homologues to important mammalian signaling molecules, including NGF (Inoue et al. (1991) *Febs Lett* 279, 38-40), acetylcholinesterase (Cousin et al., (1998) *J. Biol Chem* 273, 9812-9830), and phospholipases (John et al., (1994) *Gene* 139, 229-234) have been identified as components of snake venom. In some cases, evidence for a direct evolutionary relationship between a mammalian gene and a specific toxin gene family has been obtained. For example, a functional relationship between hemolytic snake venom toxins and cellular phospholipases has been recognized from the earliest studies of these molecules (Strydom, D. J. (1995) *Ann Rev of Biochem* 64, 563-591), and has been strongly supported by more recent protein sequence comparisons and evidence of gene duplication of this large gene family (Davidson, F. F. and Dennis, E. A. (1990) *J Mol Evol* 31, 228-238; Kini, R. M. and Chan, Y. M. (1999) *J Mol Evol* 48, 125-132). An evolutionary and functional relationship between snake venom sarafotoxins and vertebrate endothelins has also been proposed (Kochva et al., (1993) *Toxicon* 31, 544-568). These examples suggest the existence of endogenous counterparts in cases where functional homologues for toxin genes have not been identified.

One class that lacks functional homologues is the elapid snake venom neurotoxins that bind to muscle and brain acetylcholine receptors. Examples include, alpha-bungarotoxin (αBtx) which binds to and inhibits nicotinic acetyleholine receptors (Chen, D. and Patrick, J. W. (1997) *J Biol Chem* 272, 24024-24029), and the muscarinic acetylcholine receptor toxin MT3 (Jolkkonen et al., (1994) *Febs Lett.* 352, 91-94). An evolutionary relationship has been proposed between this class of neurotoxin and the mammalian Ly-6 genes based on sequence similarity (Fleming et al., (1993) *J Immunol* 150, 5379-5390, conservation of a signature motif, similar tertiary conformation, and common gene structure (Grumley et al., (1995a) *Cell Biol* 73, 277-296). Despite the evolutionary and structural similarities, no functional similarity between the elapid snake toxins and the Ly-6 genes has been established (Grumley et al., (1995a) *Cell Biol* 73, 277-296), due in part to their disparate sites of action.

Despite significant efforts into the study of ligand-gated channels such as nAChR and 5HT receptors, and the apparent commercial success of certain drugs broadly targeting these receptors and their neurotransmitters, there remains a need in the art for a more specific understanding of the molecular mechanisms of action of these receptors and the identification of native physiological molecules which might be involved in the mediation of the action of these receptors and their neurotransmitters. There remains a need in the art for more specific and selective receptor mediators both for the study of these receptors and for the advancement of therapeutic approaches aimed at these receptors and the treatment and amelioration of various disorders, including those of the CNS.

The citation of references herein shall not be construed as an admission that such is prior art to the present invention.

SUMMARY OF THE INVENTION

In its broadest aspect, the present invention extends to a novel family of polypeptides, termed Lynx, having the capability of binding to or otherwise associating with particular, specific or selective receptors or receptor molecules. In particular, this novel family of Lynx polypeptides has characteristics comprising or selected from the following: (a) such polypeptides contain multiple conserved cysteines; (b) such polypeptides demonstrate homology to members of the Ly-6 superfamily of polypeptides; (c) such polypeptides demonstrate homology to the Lynx polypeptides disclosed herein, including but not limited to Lynx 1 and Lynx 2; (d) the homology demonstrated by such polypeptides to the Lynx polypeptides disclosed herein is greater than the homology demonstrated by such polypeptides to other members of the Ly-6 superfamily of polypeptides, i.e., preferably a mature Lynx polypeptide has less than 60% homology with the amino acid sequences of SEQ ID NO's: 19-24, more preferably less than 50% homology and even more preferably less than 40% homology; (e) such polypeptides contain a C-terminal conserved GPI-attachment sequence. More particularly, the novel family of Lynx polypeptides has characteristics further comprising or selected from the following: (a) the mature proteins of such polypeptides contain less than about 120 amino acids; (b) such polypeptides are expressed in neurons; and (c) such polypeptides bind to or otherwise associate with receptors or receptor molecules, wherein such receptors or receptor molecules are selected from the following: ligand-gated channel receptors, nicotinic acetylcholine receptors, and serotonin receptors. Still more particularly, the novel family of Lynx polypeptides has characteristics wherein, on binding to or associating with a receptor or receptor molecule, the activity or function of such receptor or receptor molecule is mediated or otherwise enhanced.

In a particular embodiment, the present invention relates to all members of the herein disclosed family of Lynx polypeptides, wherein such polypeptides have characteristics comprising or selected from those detailed above. In a preferred embodiment the Lynx polypeptide has at least 70% homology in its amino acid sequence with SEQ ID NO: 2, and/or SEQ ID NO: 4 and/or SEQ ID NO: 15. In a more preferred embodiment the Lynx polypeptide has at least 80% homology in its amino acid sequence with SEQ ID NO: 2, and/or SEQ ID NO: 4 and/or SEQ ID NO: 15. In an even more preferred embodiment, the Lynx polypeptide has at least 85% homology in its amino acid sequence with SEQ ID NO: 2, and/or SEQ ID NO: 4, and/or SEQ ID NO: 15.

The present invention provides an isolated polypeptide, termed Lynx, comprising an amino acid sequence of a receptor accessory protein or ligand. In a more particular embodiment, the polypeptide comprises the amino acid sequence as set forth in SEQ ID NO:2 including fragments, mutants, variants, analogs, derivatives, or homologs thereof. In an additional embodiment, the polypeptide comprises the amino acid sequence of a mature Lynx polypeptide as set forth in SEQ ID NO:4 including fragments, mutants, variants, analogs, derivatives, or homologs thereof. In a further embodiment, the polypeptide comprises the amino acid sequence as set forth in SEQ ID NO:15 including fragments, mutants, variants, analogs, derivatives, or homologs thereof.

The isolated polypeptide is suitable for use in mediating or enhancing the activity of a receptor, particularly a ligand-gated channel receptor, more particularly a nicotinic acetylcholine receptor, a serotonin receptor, a GABA receptor or a glycine receptor.

The present invention also relates to isolated nucleic acids, such as recombinant DNA molecules or cloned genes, or degenerate variants thereof, mutants, analogs, or fragments thereof, which encode the isolated polypeptide or which competitively inhibit the activity of the polypeptide. Preferably, the isolated nucleic acid, which includes degenerates, variants, mutants, analogs, or fragments thereof, has a sequence as set forth in SEQ ID NO:1 or SEQ ID NO:14. In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present invention, and more particularly, the DNA sequences or fragments thereof determined from the sequences set forth above.

According to other preferred features of certain preferred embodiments of the present invention, a recombinant expression system is provided to produce biologically active animal, mouse or human Lynx polypeptide.

The present invention naturally contemplates several means for preparation of the Lynx polypeptide, including as illustrated herein known recombinant techniques, and the invention is accordingly intended to cover such synthetic preparations within its scope. The isolation of the cDNA and amino acid sequences disclosed herein facilitates the reproduction of the Lynx polypeptide by such recombinant techniques, and accordingly, the invention extends to expression vectors prepared from the disclosed DNA sequences for expression in host systems by recombinant DNA techniques, and to the resulting transformed hosts.

In a particular embodiment, the nucleic acid has the sequence comprising SEQ ID NO:1; a sequence complementary to SEQ ID NO:1; or a homologous sequence which is substantially similar to SEQ ID NO:1. In a further embodiment, the nucleic acid has the sequence consisting of SEQ ID NO:1.

In a particular embodiment, the nucleic acid has the sequence comprising SEQ ID NO: 14; a sequence complementary to SEQ ID NO:14; or a homologous sequence which is substantially similar to SEQ ID NO:14. In a further embodiment, the nucleic acid has the sequence consisting of SEQ ID NO:14.

The human and murine DNA sequences of the Lynx polypeptides of the present invention or portions thereof, may be prepared as probes to screen for homologous or complementary sequences and genomic clones in the same or alternate species. Most particularly, such homologous or complementary sequences shall encode polypeptides which are members of the Lynx family of polypeptides, wherein such polypeptides have characteristics comprising or selected from those detailed above. The present invention extends to probes so prepared that may be provided for screening cDNA and genomic libraries for DNA sequences encoding Lynx polypeptides. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences set forth in FIG. 1, 7 or 8 (SEQ ID NO:1, SEQ ID NO:14). Correspondingly, the preparation of antisense RNA and ribozymes are included herein.

In a still further aspect, the present invention extends to an immunogenic Lynx polypeptide or a fragment thereof. Still further, this invention provides an immunogenic polypeptide comprising the second "toxin finger" of a Lynx polypeptide. Still more particularly, the present invention provides an immunogenic Lynx polypeptide consisting of TTRTYFT-PYRMKVRKS (SEQ ID NO:3).

The present invention likewise extends to the development and use of antibodies against the Lynx polypeptide, including naturally raised and recombinantly prepared antibodies. Antibodies against the isolated polypeptide include naturally raised and recombinantly prepared antibodies. These may include both polyclonal and monoclonal antibodies prepared by known genetic techniques, as well as bi-specific (chimeric) antibodies, and antibodies including other functionalities suiting them for diagnostic use or therapeutic use. Such antibodies can be used in immunoassays to determine expression of Lynx polypeptides and expression of Lynx polypeptide receptors. In addition, the antibodies could be used to screen expression libraries to obtain additional or homologous genes that encode Lynx polypeptides, more particularly members of the family of Lynx polypeptides. These antibodies may also be suitable for modulating Lynx polypeptide receptor activity or function including but not limited to acting as competitive agents.

Thus, the Lynx polypeptides, their analogs, and any antagonists or antibodies that may be raised thereto, are capable of use in connection with various diagnostic techniques, including immunoassays, such as a radioimmunoassay or immunofluorescence, using for example, an antibody to a Lynx polypeptide that has been labeled by either radioactive addition, or radioiodination. In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

In the instance where a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The concept of the family of Lynx polypeptides contemplates that specific Lynx polypeptides exist for correspondingly specific Lynx polypeptide receptors or receptor molecules, such as ligand-gated channels and the like, most particularly nicotinic acetylcholine receptors, serotonin receptors, GABA receptors and glycine receptors. Accordingly, the exact structure of each Lynx polypeptide contemplated by the present invention, will understandably vary so as to achieve receptor and activity specificity. It is this postulated specificity and the direct involvement of the Lynx polypeptides in mediating or enhancing the activity of Lynx polypeptide receptors or receptor molecules, such as ligand-gated channels, most particularly nicotinic acetylcholine receptors, serotonin receptors, GABA receptors and glycine receptors, that offers the promise of a broad spectrum of diagnostic and therapeutic utilities.

The present invention includes an assay system which may be prepared in the form of a test kit for the quantitative analysis of the extent of the presence of the Lynx polypeptide or to identify drugs, compounds, or other agents that may mimic or block their activity. The system or test kit may comprise a labeled component prepared by one of the radioactive and/or enzymatic techniques discussed herein, coupling a label to the Lynx polypeptide, their agonists and/or antagonists, and one or more additional immunochemical reagents, at least one of which is a free or immobilized ligand, capable either of binding with the labeled component, its binding partner, one of the components to be determined or their binding partner(s). In one instance, the test compound, or an extract containing the compound, could be administered to a cellular sample expressing the Lynx polypeptide to determine the compound's effect upon the activity of the Lynx polypeptide by comparison with a control. In a further instance the test compound, or an extract containing the compound, could be administered to a cellular sample expressing the Lynx polypeptide, to determine the compound's effect upon the activity of the Lynx polypeptide, and thereby on Lynx polypeptide receptor activity, by comparison with a control. More particularly, the test compound, or an extract containing the compound, could be administered to a cellular sample expressing the Lynx1 or Lynx2 polypeptide, to determine the compound's effect upon the activity of the Lynx1 or Lynx2 polypeptide, and thereby on receptor activity, most particularly nAChR, by comparison with a control.

The invention includes an assay system for screening of potential drugs effective to modulate Lynx polypeptide receptor activity, particularly ligand-gated channel activity, most particularly nAChR activity, of target mammalian cells, particularly neurons by mimicking, agonising, antagonising, interrupting or potentiating the Lynx polypeptide.

The assay system could more importantly be adapted to identify drugs or other entities that are capable of binding to the Lynx polypeptide and/or Lynx polypeptide receptor, thereby inhibiting or potentiating Lynx polypeptide receptor activity. Such assay would be useful in the development of drugs that would be specific against particular receptors, or that would potentiate such activity, in time or in level of activity. For example, such drugs might be used to activate or inhibit ligand-gated ion channels, particularly nAChR, serotonin receptors, GABA receptors or glycine receptors, or to treat CNS pathologies, as for example, cognitive disorders, memory or learning deficits, Parkinson's disease, and Alzheimer's disease.

The present invention further relates to methods for identifying additional members of the herein disclosed family of Lynx polypeptides, most particularly wherein such members have characteristics comprising or selected from those detailed above and herein. Any such methods employ the knowledge and skills of those in the art. Such methods include the isolation of such family members by virtue of their homology to the Lynx polypeptides specifically disclosed herein. Additional methods include isolation of family members by virtue of their characteristic capability of binding to or otherwise associating with particular or selective receptors or receptor molecules or fragments thereof.

The invention includes animals, particularly transgenic animals, wherein the expression or amount of Lynx protein or the Lynx gene is altered or enhanced. In particular, transgenic animals with genetic alterations in the dosage of a Lynx gene are contemplated. Still more particularly, the invention relates to transgenic animals expressing a soluble version of the Lynx protein. In a particular embodiment, the soluble version of Lynx protein lacks a C-terminal GPI attachment sequence, but contains a signal sequence. Transgenic animals wherein the gene or genes encoding Lynx protein are knocked-out or mutated are also contemplated.

In a further embodiment, the present invention relates to certain therapeutic methods which would be based upon the activity of the Lynx polypeptide, or active fragments thereof, or upon agents or other drugs determined to possess the same activity. More specifically, the therapeutic method generally referred to herein could include the method for the treatment of various pathologies or other cellular dysfunctions and derangements by the administration of pharmaceutical compositions that may comprise effective inhibitors or enhancers of activation of Lynx polypeptides, or other equally effective drugs developed for instance by a drug screening assay prepared and used in accordance with a further aspect of the present invention.

In particular, the Lynx polypeptides of the present invention whose sequences are presented in SEQ ID NO: 1 and SEQ ID NO:14 herein, their antibodies, agonists, antagonists, or active fragments thereof, could be prepared in pharmaceutical formulations for administration in instances wherein mediation or enhancement of the activity of Lynx polypeptide receptors, most particularly nAChR or serotonin receptors, is appropriate or desired, such as in treatment of cognitive, learning or memory deficits or disorders. The specificity of the Lynx polypeptides hereof would make it possible to better manage the shortcomings and nonspecific side effects of many current CNS therapies.

It is a still further object of the present invention to provide a method for the treatment of mammals to control the amount or activity of the Lynx polypeptides or Lynx polypeptide receptors or receptor molecules, so as to alter the adverse consequences of such presence or activity, or where beneficial, to enhance such activity.

It is a still further object of the present invention to provide pharmaceutical compositions for use in therapeutic methods which comprise or are based upon the Lynx polypeptides, its subunits, their binding partner(s), including particularly Lynx polypeptide receptors or receptor molecules, or upon agents or drugs that control the production, or that mimic or antagonize the activities of the Lynx polypeptides. Such pharmaceutical compositions may further comprise acetylcholine, acetylcholine-like compounds or analogs, or other agents which enhance or otherwise increase the amount or concentration of acetylcholine at or near acetylcholine receptors, for instance acetyl-cholinesterase inhibitors. The invention further provides pharmaceutical compositions comprising the Lynx polypeptides or antibodies thereto, and diagnostic and therapeutic methods of use thereof.

It is still a further object of the present invention to provide a method for the treatment of mammals to control or mediate the activity of a Lynx polypeptide receptor, so as to treat or avert the adverse consequences of invasive, spontaneous, or idiopathic pathological states. More particularly, it is a further object of the present invention to provide a method for controlling, mediating or enhancing the activity of a Lynx polypeptide receptor using Lynx polypeptides, or analogs, fragments or derivatives thereof. Still more particularly, it is an object of the present invention to provide a method for controlling, mediating or enhancing the activity of the nicotinic acetylcholine receptor using Lynx polypeptides, or analogs, fragments or derivatives thereof. This invention provides pharmaceutical compositions for use in therapeutic methods which comprise or are based upon the isolated Lynx polypeptides, their subunits or their binding partners, including particularly Lynx polypeptide receptors or receptor molecules.

Other objects and advantages will become apparent to those skilled in the art from a review of the following description which proceeds with reference to the following illustrative drawings.

BRIEF DESCRIPTION OF THE DRAWINGS

FIG. 1 depicts the nucleic acid sequence and predicted amino acid sequence of the GC26 (Lynx1) cDNA.

FIG. 2A depicts the predicted amino acid sequence of the Lynx1 open reading frame (ORF). The boxed N-terminus demarcates the putative signal sequence. The C-terminal transmembrane domain that is cleaved during the processing of the GPI anchor, is boxed. The consensus recognition sequence for the attachment of the GPI moiety is indicated in brackets [Undenfriend et al., Ann Rev. of Biochem. 64:563-591 (1995)]. Non-polar residues are shaded. Arrowheads designate the position of the intron breaks in the gene.

FIG. 2B depicts the amino acid sequence homology between Lynx1 and members of the Ly-6/α-bungarotoxin gene superfamily. Family members comprise two groups: (i) the lymphocyte cell surface antigens E48 antigen, Ly-6 A/E, CD59, and (ii) the elapid snake venom toxin peptides, α-cobratoxin (α-Ctx), α-bungarotoxin (α-Btx), and m3 toxin (M3tx). The putative mature amino acid sequence only was used for these alignments. The Ly-6 consensus motif is shown above. Residues corresponding to this consensus are shaded in black. Residues matching the lynx1 polypeptide are shaded in grey. Numbers at the right indicate the percentage similarity/identity to the Lynx1 mature polypeptide.

FIGS. 3A and B depict the expression of the Lynx1 gene in neurons. FIG. 3A depicts a Northern blot analysis of Lynx1 gene expression. PolyA+RNA from adult murine tissues (as indicated) was probed with the Lynx1 cDNA (upper panel) and with a GAPDH loading control (lower panel). Lynx1 is highly expressed in the brain, with lower levels of expression in the kidney. The Lynx1 cDNA hybridizes to a band of approximately 4.1 kb. FIG. 3B depicts in situ hybridization analysis that demonstrates Lynx1 expression in integrative output neurons across multiple circuits in the brain. FIGS. 3B-1 and 3B-2 depict bright and darkfield photomicrographs, respectively, of the same field of the mouse cerebellum reacted with the lynx1 antisense $^{35}$S-labeled riboprobe. FIGS. 3B-2 depicts that Lynx1 is detected in the Purkinje cell body layer (PC), and the deep cerebellar nuclei, (DCN). FIGS. 3B-3 depicts that no signal is observed with the sense control probe. FIGS. 3B-4 depicts that Lynx1 expression is high in the deep layers of the cerebral cortex (V/VI). FIGS. 3B-5 depicts CA3 pyramidal neurons of the hippocampal formation (CA3), FIGS. 3B-6 depicts mitral cells of the olfactory bulb (MC).

FIG. 6A-6C depicts the results of rotarod testing of transgenic animals expressing soluble Lynx1 versus wild type animals. A presents a tabulation of the data. B provides a graph of the average number of seconds transgenic and wild-type animals run upright of the rotarod for days 1-5. C is a graph of the increase in seconds observed for transgenic animals versus wildtype animals.

FIG. 7 depicts the nucleic acid sequence of mouse and human ESTs identified by database search using Lynx1 polypeptide and Lynx1 nucleic acid sequences. Mouse ESTs are AA139375, AA92910, AA268004, AA711715, and AA619349. Human ESTs are H46196, H19490, H19572 and H46195.

FIG. 8 depicts the obtained nucleic acid sequence and predicted amino acid sequence of human Lynx2 as identified from a human cDNA library.

FIG. 9 presents a comparison of the Lynx1 model and the α-bungarotoxin experimental structure. Left panel, three-dimensional model of Lynx. Strands are shown as green arrows and disulfide bridges are colored yellow. Right panel, experimental NMR structure of α-bungarotoxin (PDB code 1abt). The orientation and coloring is the same as for Lynx1. N and C terminal ends of the molecules are labeled.

DETAILED DESCRIPTION

Figure 4A:
FIGS. 4A-4F display photomicrographs depicting Lynx1 protein expression in Purkinje cells of cerebellar cortex. Figures A and C depict low and higher power photomicrographs of mouse cerebellum immunostained with Lynx1 peptide antisera. Lynx1 expression is confined to proximal dendrites and soma of Purkinje cells in the cerebellar cortex. Figure B depicts no staining is observed with pre-immune control sera. Figures C and D depict adjacent serial sections reacted with Lynx1 and calbindin antisera, respectively, contrasts the limited distribution of Lynx1 as compared to calbindin. Figure E depicts calbindin antisera (green) labels the complete dendritic arbor of Purkinje cells including the finely articulated spiny branchlets, whereas Lynx1 antisera (red) labels only the proximal dendritic branches of these neurons. Figure F depicts the profile of inhibitory synapses onto Purkinje cells, as revealed by GAD immunoreactivity (green), shows inhibitory synaptic termini closely apposed to Lynx1 positive postsynaptic domains (red). This is in contrast to the profile of all synapses, which is densely packed and evenly distributed across the molecular layer of the cerebellum and not confined to a dendritic subfield (data not shown).
Figure 4B:
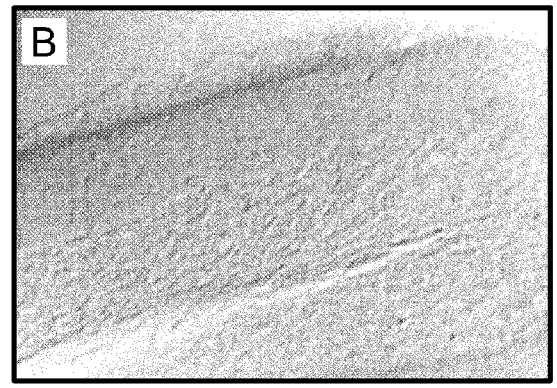
Figure 4C:
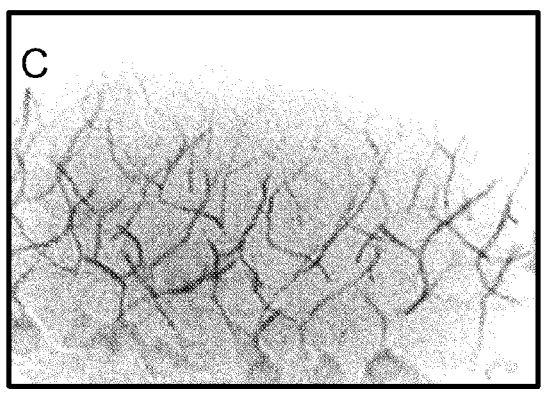
Figure 4D:
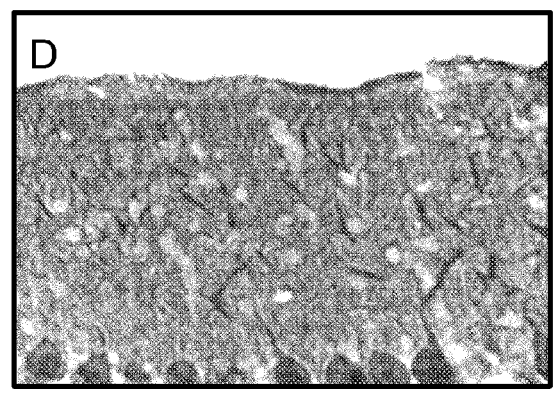
Figure 4E:
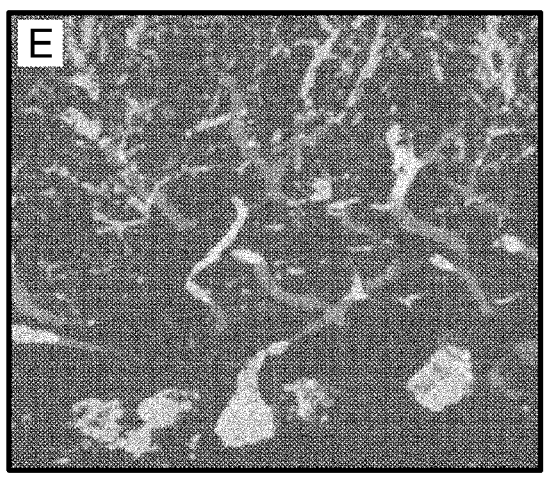
Figure 4F:
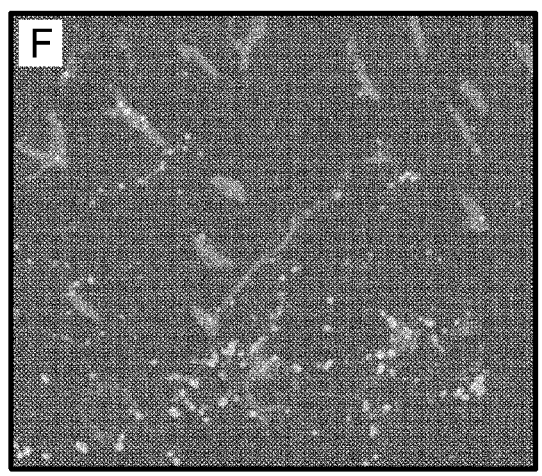

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual". (1989); "Current Protocols in Molecular Biology" Volumes I-III [Ausubel, R. M., ed. (1994)]; "Cell Biology: A Laboratory Handbook" Volumes I-III [J. E. Cells, ed. (1994))]; "Current Protocols in Immunology" Volumes I-III [Coligan, J. E., ed. (1994)]; "Oligonucleotide Synthesis" (M. Gait ed. 1984); "Nucleic Acid Hybridization" [B. D. Hames & S. J. Higgins e's. (1985)]; "Transcription And Translation" [B. D. Hams & S. J. Higgins, e's. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "Lynx polypeptide", "Lynx", "Lynx family member", and any variants not specifically listed, may be used herein interchangeably, and as used throughout the present application and claims refer to proteinaceous material including single or multiple proteins, and extends to those proteins having the amino acid sequence described herein and presented in FIG. 2A (SEQ ID NO:2), and the profile of activities and characteristics set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "Lynx polypeptide", "Lynx", "Lynx family member", are intended to include within their scope proteins specifically recited herein as well as all substantially homologous analogs, allelic variations, and fragments thereof, and additional family members contemplated herein. Lynx1 and Lynx2 are particular members of the Lynx family.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" is included at the beginning of the coding sequence of a protein to be expressed on the surface of a cell. This sequence encodes a signal peptide, N-terminal to the polypeptide, that directs the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

A "GPI attachment sequence" is a consensus amino acid sequence recognized as a signal for glycosyl-phosphatidylinositol (GPI) anchor biosynthesis and attachment, which is cleaved during the GPI attachment process. Proteins or polypeptides containing a GPI attachment sequence are membrane associated by virtue of the attachment of GPI.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A nucleic acid molecule is "hybridizable" to another acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$. High stringency hybridization conditions correspond to the highest $T_m$, e.g. 65° C., 1×SSC, 0.1% SDS. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 15 nucleotides;

more preferably at least about 20 cleotides; most preferably the length is at least about 30 nucleotides.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

As used herein, the term "homology" when used in reference to a comparison of amino acid sequences of two or more polypeptides is indicative of a percent likeness of the amino acid sequences as determined by a standard computer analysis which is comparable or preferably the same as that determined by an Advanced Blast search at www.ncbi.nlm.nih.gov under default filter conditions. (See also Example 1). Preferably the percent homology determined for the amino acid sequences of two or more polypeptides corresponds to a comparison of analogous forms of the polypeptides, i.e. the percent homology of mature polypeptides; or the percent homology of the translation products of the entire open reading frames; etc.

Two DNA sequences are "substantially homologous" when at least about 70% (preferably at least about 80%, and most preferably at least about 85 or 90%) of the nucleotides match over the defined length of the DNA sequences. Sequences that are substantially homologous can be identified by comparing the sequences using standard software available in sequence databases, particularly using Advanced Blast Search under default filter conditions at www.ncbi.n/m.nih.gov, or in Southern hybridization experiments under, for example, moderate stringency hybridization or stringent hybridization conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding Lynx polypeptides which code for a Lynx polypeptide having the same amino acid sequence as SEQ ID NO:2, but which are degenerate to SEQ ID NO:1. The same is applicable and appropriate with respect to any Lynx family member, including but not limited to those DNA sequences specified in SEQ ID NOs: By "degenerate to" is meant that a different three-letter codon is used to specify a particular amino acid. It is well known in the art that the following codons can be used interchangeably to code for each specific amino acid:

```
Phenylalanine (Phe or F)   UUU or UUC

Leucine (Leu or L)         UUA or UUG or CUU or CUC
                           or CUA or CUG Isoleucine (Ile or I)      AUU or AUC or AUA Methionine (Met or M)      AUG Valine (Val or V)          GUU or GUC of GUA or GUG
```

```
Serine (Ser or S)          UCU or UCC or UCA or UCG
                           or AGU or AGC Proline (Pro or P)         CCU or CCC or CCA or CCG Threonine (Thr or T)       ACU or ACC or ACA or ACG Alanine (Ala or A)         GCU or GCG or GCA or GCG Tyrosine (Tyr or Y)        UAU or UAC Histidine (His or H)       CAU or CAC Glutamine (Gln or Q)       CAA or CAG Asparagine (Asn or N)      AAU or AAC Lysine (Lys or K)          AAA or AAG Aspartic Acid (Asp or D)   GAU or GAC Glutamic Acid (Glu or E)   GAA or GAG Cysteine (Cys or C)        UGU or UGC Arginine (Arg or R)        CGU or CGC or CGA or CGG
                           or AGA or AGG Glycine (Gly or G)         GGU or GGC or GGA or GGG Tryptophan (Trp or W)      UGG Termination codon          UAA (ochre) or UAG (amber)
                           or UGA (opal)
```

It should be understood that the codons specified above are for RNA sequences. The corresponding codons for DNA have a T substituted for U.

Mutations can be made in a nucleic acid encoding a Lynx polypeptide, including but not limited to in particular, in SEQ ID NO:1, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino Acids with Nonpolar R Groups
Alanine
Valine
Leucine
Isoleucine
Proline
Phenylalanine
Tryptophan Methionine
Amino Acids with Uncharged Polar R Groups
Glycine
Serine
Threonine
Cysteine
Tyrosine
Asparagine
Glutamine
Amino Acids with Charged Polar R Groups (Negatively Charged at pH 6.0)
Aspartic acid
Glutamic acid
Basic Amino Acids (Positively Charged at pH 6.0)
Lysine
Arginine
Histidine (at pH 6.0)
Another Grouping May be Those Amino Acids with Phenyl Groups:
Phenylalanine
Tryptophan
Tyrosine
Another Grouping May be According to Molecular Weight (i.e., Size of R Groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred conservative amino acid substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. Such antibodies include but are not limited to polyclonal, monoclonal, chimeric, single chain, Fab fragments, and an Fab expression library.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by, at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

In its primary aspect, the present invention concerns the identification of a novel family of receptor accessory molecules or ligands, termed Lynx. In a particular embodiment, the present invention relates to all members of the herein disclosed family of Lynx polypeptides and to nucleic acids encoding polypeptides which are members of the Lynx family. Such Lynx polypeptides have the capability of binding to or otherwise associating with particular, specific or selective receptors or receptor molecules. In particular, this novel family of Lynx polypeptides has characteristics comprising or selected from the following: (a) such polypeptides contain multiple conserved cysteines; (b) such polypeptides demonstrate homology to members of the Ly-6 superfamily of polypeptides; (c) such polypeptides demonstrate homology to the Lynx polypeptides disclosed herein, including but not limited to Lynx 1 and/or Lynx 2; (d) the homology demonstrated by such polypeptides to the Lynx polypeptides disclosed herein is greater than the homology demonstrated by such polypeptides to other members of the Ly-6 superfamily of polypeptides; (e) such polypeptides contain a C-terminal conserved GPI-attachment sequence. More particularly, the novel family of Lynx polypeptides has characteristics further comprising or selected from the following: (a) the mature proteins of such polypeptides contain less than about 120 amino acids; (b) such polypeptides are expressed in neurons; and (c) such polypeptides bind to or otherwise associate with receptors or receptor molecules, wherein such receptors or receptor molecules are selected from the following: ligand-gated channel receptors, nicotinic acetylcholine receptors, and serotonin receptors. Still more particularly, the novel family of Lynx polypeptides has characteristics wherein, on binding to or associating with a receptor or receptor molecule, the activity or function of such receptor or receptor molecule is mediated or otherwise enhanced.

The present invention more particularly relates to specific Lynx polypeptides set forth in SEQ ID NO:2, SEQ ID NO: 4 and SEQ ID NO: 15. The Lynx polypeptide of SEQ ID NO:2 and SEQ ID NO: 4, termed herein Lynx1, is capable of binding to or associating with the nicotinic acetylcholine receptor, specifically the alpha subunit of such receptor. Lynx1 polypeptide is further capable of enhancing the activity of the nAChR, as demonstrated further in the Examples provided herein.

As stated above, the present invention also relates to a recombinant DNA molecule or cloned gene, or a degenerate variant thereof, which encodes a Lynx polypeptide, or a fragment thereof, that possesses an amino acid sequence set forth in FIG. 2A (SEQ ID NO:2), SEQ ID NO:4, or FIG. 8 (SEQ ID NO: 15); preferably a nucleic acid molecule, in particular a recombinant DNA molecule or cloned gene, encoding the Lynx polypeptide has a nucleotide sequence or is complementary to a DNA sequence shown in FIG. 1 (SEQ ID NO:1) or FIG. 8 (SEQ ID NO: 14).

Further this invention also provides a vector which comprises the above-described nucleic acid molecule. The promoter may be, or is identical to, a bacterial, yeast, insect or mammalian promoter. Further, the vector may be a plasmid, cosmid, yeast artificial chromosome (YAC), bacteriophage or eukaryotic viral DNA. Other numerous vector backbones known in the art as useful for expressing protein may be employed. Such vectors include, but are not limited to: adenovirus, simian virus 40 (SV40), cytomegalovirus (CMV), mouse mammary tumor virus (MMTV), Moloney murine leukemia virus, DNA delivery systems, i.e. liposomes, and expression plasmid delivery systems. Further, one class of vectors comprises DNA elements derived from viruses such as bovine papilloma virus, polyoma virus, baculovirus, retroviruses or Semliki Forest virus. Such vectors may be obtained commercially or assembled from the sequences described by methods well-known in the art.

This invention also provides a host vector system for the production of a polypeptide which comprises the vector of a suitable host cell. Suitable host cells include, but are not limited to, prokaryotic or eukaryotic cells, e.g. bacterial cells (including gram positive cells), yeast cells, fungal cells, insect cells, and animals cells. Numerous mammalian cells may be used as hosts, including, but not limited to, the mouse fibroblast cell NIT-3T3, CHO cells, HeLa cells, Ltk⁻ cells, Cos cells, etc.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2µ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the JAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

This invention further provides a method of producing a polypeptide which comprises growing the above-described host vector system under suitable conditions permitting the production of the polypeptide and recovering the polypeptide so produced.

This invention further provides an antibody capable of specifically recognizing or binding to the isolated polypeptide. The antibody may be a monoclonal or polyclonal antibody. Further, the antibody may be labeled with a detectable marker that is either a radioactive, calorimetric, fluorescent, or a luminescent marker. The labeled antibody may be a polyclonal or monoclonal antibody. In one embodiment, the labeled antibody is a purified labeled antibody. Methods of labeling antibodies are well known in the art.

For preparation of monoclonal antibodies, or fragment, analog, or derivative thereof, any technique that provides for the production of antibody molecules by continuous cell lines in culture may be used (see, e.g., *Antibodies—A Laboratory Manual*, Harlow and Lane, eds., Cold Spring Harbor Laboratory Press: Cold Spring Harbor, N.Y., 1988). These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in *Monoclonal Antibodies and Cancer Therapy*, Alan R. Liss, pp. 77-96). In fact, according to the invention, techniques developed for the production of "chimeric antibodies" (Morrison et al., 1984, *J. Bacteriol.* 159-870; Neuberger et al., 1984, *Nature* 312:604-608; Takeda et al., 1985, *Nature* 314: 452-454) by splicing the genes from a mouse antibody molecule specific for a polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves. An additional embodiment of the invention utilizes the techniques described for the construction of Fab expression libraries (Huse et al., 1989, *Science* 246:1275-1281) to allow rapid and easy identification of monoclonal Fab fragments with the desired specificity for the polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodine); magnetic resonance shift reagents (such as gadolinium and manganese); or radio-opaque reagents.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The polypeptide can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

The possibilities both diagnostic and therapeutic that are raised by the now recognized existence of the Lynx polypeptide, derive from the fact such polypeptides represent a novel family of receptor accessory molecules or ligands. In particular the Lynx polypeptides are capable of binding to or associating with a receptor or receptor molecule, whereby the activity or function of such receptor or receptor molecule is mediated or otherwise enhanced. As suggested earlier and elaborated further on herein, the present invention contemplates pharmaceutical intervention in the cascade of reactions in which a Lynx polypeptide and its receptor are implicated. More particularly, as provided by the Examples herein, Lynx 1 polypeptide, as characterized herein and set forth in SEQ ID NO:2 has been demonstrated to bind to or associate with nicotinic acetylcholine receptors, specifically through the alpha subunit of such receptors. In addition, Lynx1 is capable of mediating and enhancing the activity of its receptor, nAChR, as further provided herein. Thus, Lynx1 and its family of related Lynx polypeptides provide a means to new diagnostic and therapeutic approaches for monitoring and manipulating the cholinergic system.

Lynx Polypeptide Family Members

As disclosed herein, the present invention contemplates a novel family of receptor accessory molecules or ligands, termed Lynx, and relates to all members of the herein disclosed family of Lynx polypeptides and to nucleic acids encoding polypeptides which are members of the Lynx family. Such Lynx polypeptides have the capability of binding to or otherwise associating with particular, specific or selective receptors or receptor molecules. In particular, this novel family of Lynx polypeptides has characteristics comprising or selected from the following: (a) such polypeptides contain multiple conserved cysteines; (b) such polypeptides demonstrate homology to members of the Ly-6 superfamily of polypeptides; (c) such polypeptides demonstrate homology to the Lynx polypeptides disclosed herein, including but not limited to Lynx 1 and/or Lynx 2: (d) the homology demonstrated by such polypeptides to the Lynx polypeptides disclosed herein is greater than the homology demonstrated by such polypeptides to other members of the Ly-6 superfamily of polypeptides; (e) such polypeptides contain a C-terminal conserved GPI-attachment sequence. More particularly, the novel family of Lynx polypeptides has characteristics further comprising or selected from the following: (a) the mature proteins of such polypeptides contain less than about 120 amino acids; (b) such polypeptides are expressed in neurons; and (c) such polypeptides bind to or otherwise associate with receptors or receptor molecules, wherein such receptors or receptor molecules are selected from the following: ligand-gated channel receptors, nicotinic acetylcholine receptors, and serotonin receptors. Still more particularly, the novel family of Lynx polypeptides has characteristics wherein, on binding to or associating with a receptor or receptor molecule, the activity or function of such receptor or receptor molecule is mediated or otherwise enhanced.

The above stated characteristics of Lynx polypeptides can be utilized in methods to identify and characterize additional members of the Lynx polypeptide family. For instance, Lynx1 encoding nucleic acid sequence can be utilized in identification of homologous Lynx genes encoding putative additional Lynx polypeptides by methods as exemplified herein and using further methods of the skilled artisan. Functional characteristics of the Lynx polypeptides may also be employed in methods to isolate Lynx polypeptide family members. The recognized ability of Lynx polypeptides to bind to or associate with receptors or receptor molecules, as exemplified herein in Lynx1 binding to nAChR alpha subunit, can be used to identify Lynx polypeptides using receptor molecules or fragments thereof. For instance, the receptor subunits can be utilized in methods to identify Lynx polypeptides that interact with such subunits. Exemplary methods contemplated by the present invention are those which utilize the N-terminus of nAChR subunit alpha or 5HT receptors to screen cDNA libraries based on binding. One means to detect binding is using a yeast two-hybrid technique (Fields S. and Song, O.-K. (1989) *Nature* 340, 245-246). Methods of this nature are within the art and have already been described, for example, with respect to intracellular receptor associated molecules for glutamate and AMPA receptors (Dong, H. et al (1997) *Nature* 386, 279-284; Brakeman, P. R. et al (1997) *Nature* 386, 284-288).

Methods of Identifying Members of the Lynx Polypeptide Family

The present invention contemplates isolation of genes encoding members of the Lynx family of polypeptides of the present invention, including a full length, or naturally occurring forms of Lynx 1 and Lynx 2, from any animal, particularly mammalian, and more particularly human, source. Such nucleic acids may be used for designing primers for RT-PCR, and for making probes that are useful for determining the expression of Lynx messenger RNA in tissues. Similarly such nucleic acids can be used to determine the expression of Lynx messenger RNA in tissues by Northern Blot analysis, RNA protection assays and the like. A gene encoding a Lynx polypeptide, whether genomic DNA or cDNA, can be isolated from any source, particularly from a human cDNA or genomic library. In view and in conjunction with the present teachings, methods well known in the art, as described above can be used for obtaining Lynx genes from any source (see, e.g., Sambrook et al., 1989, supra).

Accordingly, any animal cell or transformed animal cell line potentially can serve as the nucleic acid source for the identification and/or molecular cloning of a Lynx gene. The DNA may be obtained by standard procedures known in the art from cloned DNA (e.g., a DNA "library"), and preferably is obtained from a cDNA library prepared from tissues with high level expression of the protein, by chemical synthesis, by cDNA cloning, or by the cloning of genomic DNA, or fragments thereof, purified from the desired cell (See, for example, Sambrook et al, 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene. Yet another aspect of the present invention comprises methods of identifying the nucleotide and amino acid sequences of a Lynx gene. Once the coding region of the nucleotide sequence is identified, the corresponding amino acid sequence can be readily determined using the genetic code, preferably with the aid of a computer. Preferably the full-length nucleotide sequence of the coding region of a Lynx gene is identified. It is also preferable that the Lynx gene is a mammalian gene, more preferably a human gene. Recombinant DNA molecules and the recombinant Lynx proteins obtained by these methods are also part of the present invention.

One method of identifying a nucleotide sequence of the coding region of a Lynx gene comprises comparing SEQ ID NO:2, and/or SEQ ID NO:4 and/or SEQ ID NO:15 with the amino acid sequences encoded by nucleic acids that are obtained from a library of nucleic acids containing partial nucleotide sequences of the coding regions of genes. Preferably this determination is aided by computer analysis. A nucleic acid containing a partial nucleotide sequence of a coding region from a gene that is at least 70%, preferably 80% and more preferably 85% homologous to a comparable portion of SEQ ID NO:2, and/or SEQ ID NO:4 and/or SEQ ID NO:15 can then be selected. Methods of ascertaining which nucleic acid and amino acid sequences are homologous are described herein.

The full-length sequence of the coding region of the Lynx gene is preferably determined. The sequence is identified as being that of a Lynx gene when it is at least 70%, preferably 80% and more preferably 85% homologous to SEQ ID NO:2, and/or SEQ ID NO:4 and/or SEQ ID NO:15. In a preferred embodiment this method further comprises determining whether the nucleotide sequence that contains a coding region for the selected amino acid sequence is also expressed in neurons. When the nucleotide sequence is expressed in a neuron, it is identified as the nucleotide sequence of the coding region of a Lynx gene. One means of determining whether the nucleotide sequence is expressed in a neuron is through the use of a labeled nucleotide probe for the nucleotide sequence that contains the coding region for the amino acid sequence. The labeled nucleotide probe can then be hybridized under stringent conditions with a sample containing nucleic acids that are expressed in the neuron. If hybridization is detected, the sequence is identified as being that of a Lynx gene. Similarly, a PCR primer can be used to aid in the confirmation of the identification of a nucleotide sequence of the coding region of the Lynx gene In a particular embodiment of the method; determining the full-length sequence of the coding region is performed by sequencing the insert of a plasmid which contains a nucleic acid encoding an amino acid sequence that is at least 70%, preferably 80% and more preferably 85% homologous to SEQ ID NO:2, and/or SEQ ID NO:4 and/or SEQ ID NO:15. In this case, the insert comprises the nucleic acid. In another embodiment, the full-length sequence is determined by PCR.

A related embodiment includes a method of identifying the full-length nucleotide sequence of the coding region of a Lynx gene that comprises determining the percent homology of SEQ ID NO:2, and/or SEQ ID NO:15 to amino acid sequences encoded by nucleotide sequences from a library of nucleotide sequences and then selecting a nucleotide sequence that contains a coding region for an amino acid sequence that is at least 70%, preferably 80% and more preferably 85% homologous to SEQ ID NO:2, and/or SEQ ID NO:15. The full-length nucleotide sequence of the coding region for the amino acid sequence is determined and the full-length nucleotide sequence of the coding region of the Lynx gene is identified. This method can also comprise determining whether the nucleotide sequence is expressed in the neurons. When the nucleotide sequence is expressed in neurons it is identified as the nucleotide sequence of the coding region of the Lynx gene.

In another embodiment, the method can further comprise constructing a recombinant DNA that contains the coding region. In one such embodiment a recombinant Lynx protein is made by expressing the recombinant DNA. In a preferred embodiment of this type an activity of the recombinant Lynx is assayed. In one such embodiment, the activity assayed for is the ability of the recombinant protein to associate with or preferably bind to a receptor and thereby mediate or enhance the activity or the function of the receptor. Preferably the receptor is a ligand-gated channel receptor, a nicotinic acetylcholine receptor, a serotonin receptor, a GABA receptor, or a glycine receptor. More preferably it binds specifically to one of these receptors and even more preferably it binds to an .alpha.-subunit (e.g., α7) of a nicotinic acetylcholine receptor.

In an alternative embodiment the initial identification of a nucleic acid encoding a Lynx polypeptide is performed by hybridization. In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography. Alternatively a cDNA library can be screened.

Once DNA fragments are generated, identification of the specific DNA fragment containing the desired Lynx gene may be accomplished in a number of ways. For example, the generated DNA fragments may be screened by nucleic acid hybridization to a labeled probe of the present invention (Benton and Davis, 1977, Science 196:180; Grunstein and Hogness, 1975, Proc. Natl. Acad. Sci. U.S.A. 72:3961). For example, a set of oligonucleotides corresponding to the sequence information provided by the present invention can be prepared and used as probes for DNA encoding a Lynx polypeptide (e.g., in combination with a poly-T primer for RT-PCR). Preferably, a probe is selected that is highly unique to Lynx 1 or Lynx 2 of the invention. Those DNA fragments with substantial homology to the probe will hybridize. As noted above, the greater the degree of homology, the more stringent hybridization conditions can be used.

Once a suitable DNA fragment or cDNA clone is identified the sequence of the coding region from the fragment or cDNA can be determined. If the sequence is at least 70%, preferably 80% and more preferably 85% homologous to a comparable portion of SEQ ID NO:2, and/or SEQ ID NO:4 and/or SEQ ID NO:15 it is then selected. The DNA fragment or cDNA can then be used as a probe to get a full-length DNA or cDNA. Once this nucleotide sequence is determined, the corresponding nucleic acid can be expressed and the recombinant polypeptide can be further tested for its activity as described above.

As indicated above, the nucleotide sequence of the Lynx 1 and Lynx 2, or more preferably their corresponding amino acid sequences, can be used to search for other Lynx family members using computer data bases containing partial nucleic acid sequences. Human ESTs, for example, can be searched. These amino acid sequences, for example, can be compared with computer translated human EST sequences, e.g., in GenBank, using GCG software and the blast search program for example. Matches with highly homologous EST sequences can then be obtained.

The matched EST can then be fully sequenced. One such example is outlined here, though many equivalent systems and variations are known and practiced in the art. DNA sequencing reactions can be assembled on a Beckman Biomek robotic system using standard dye-terminator chemistry, Taq polymerase and thermal cycling conditions described by the vendor (Perking Elmer/Applied Biosystems Division (PE/AB)). Preferably sequencing is performed multiple times to insure accuracy. Reaction products can be resolved on PE/ABD model 373 and 377 automated DNA sequencers. Contig assembly can be performed using any number of programs (e.g., Gap4) and a consensus sequence can be further analyzed using the GCG suite of applications. The resulting sequence can then be used in place of, and/or in conjunction with SEQ ID NO:1 for example to identify other ESTs which contain coding regions of Lynx proteins.

Plasmids containing the matched ESTs can be digested with restriction enzymes in order to release the cDNA inserts. If the plasmid does not contain a full length Lynx polypeptide the digests can be purified, e.g., run on an agarose gel and the bands corresponding to the inserts can be cut from the gel and purified (Quiagen Gel Extraction kit). Such purified inserts are likely to contain overlapping regions which can be combined as templates of a PCR reaction using primers which are preferably located outside of the Lynx open reading frame. The PCR reaction can be performed using ELONGASE (and its standard amplification system) supplied by Gibco-BRL, Gaithersburg, Md., under the following standard conditions: 5 minutes at 94° C.; followed by 25 cycles of: 30 seconds at 94° C., 30 seconds at 50° C., and 3.5 minutes at 72° C.; followed by 10 minutes at 72° C., for example. Amplification should yield the expected product which can be ligated into a vector and used to transform an *E. coli* derivative via TA cloning (Invitrogen) for example. The resulting full-length Lynx nucleic acid can be placed into an expression vector and the expressed recombinant Lynx can then be assayed for the characteristic properties of Lynx family proteins as described above.

Alternatively, plasmids containing matched EST homologue fragments can be used to transform competent bacteria (e.g. from Gibco BRL, Gaithersburg Md.). Bacteria can be streaked, then grown up overnight. Plasmid preps can be performed (e.g., Quiagen Corp, Santa Clarita Calif.) and the plasmids can be digested by simultaneous restriction digest. Products of the digest can be separated by size on an agarose gel, for example, and purified. The corresponding bands cut from these gels can be ligated to form a full length Lynx cDNA and used to transform competent bacteria and the resulting plasmid can be purified.

In still another embodiment the ability of a Lynx polypeptide to associate or bind a receptor can be used to identify nucleic acids that encode portions or all of a Lynx polypeptide. In one such embodiment, an expression library is screened for the ability of the polypeptide products to bind a ligand-gated channel receptor, a nicotinic acetylcholine receptor, a serotonin receptor, a GABA receptor, or a glycine receptor. In one particular embodiment the recombinant polypeptide is contacted with a receptor and the binding or association of the receptor and the poly peptide is detected. The detection of binding or associating identifies the polypeptide as a candidate Lynx.

The sequence of the nucleic acid encoding the candidate Lynx polypeptide can then be obtained. A nucleic acid having a nucleotide sequence of a coding region that is at least 70%, preferably 80% and more preferably 85% homologous to a comparable portion of SEQ ID NO:2, and/or SEQ ID NO:4 and/or SEQ ID NO:15 can then be selected. In a preferred embodiment, the activity of the polypeptide is assayed for its ability to associate with or preferably bind to a receptor and thereby mediate or enhance the activity or the function of the receptor. Preferably it binds specifically to only one type of receptor and even more preferably it binds to an α-subunit (e.g., α7) of a nicotinic acetylcholine receptor. In another particular embodiment, the binding or associating of the recombinant polypeptide and the receptor is performed by the yeast two-hybrid method.

Diagnostic Applications

In a further embodiment of this invention, commercial test kits suitable for use by a medical specialist may be prepared to determine the presence or absence of Lynx polypeptide or to identify Lynx polypeptide. In accordance with the testing techniques discussed above, one class of such kits will contain at least the labeled polypeptide or its binding partner, for instance an antibody specific thereto or a receptor or receptor molecule specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined bacterial binding activity, comprising:

(a) a predetermined amount of at least one labeled immunochemically reactive component obtained by the direct or indirect attachment of the present the polypeptide or a specific binding partner thereto, to a detectable label;

(b) other reagents; and (c) directions for use of said kit.

As suggested earlier, the diagnostic method of the present invention comprises examining a cellular sample or medium by means of an assay including an effective amount of an antagonist to a Lynx polypeptide, such as an anti-Lynx1 antibody, preferably an affinity-purified polyclonal antibody, and more preferably a mAb. In addition, it is preferable for the anti-Lynx antibody molecules used herein be in the form of Fab, Fab', F(ab')$_2$ or F(v) portions or whole antibody molecules. As previously discussed, patients capable of benefiting from this method include those suffering from cognitive, memory or learning deficits, Parkinson's disease and Alzheimer's disease. Methods for isolating the Lynx polypeptide and inducing anti-Lynx antibodies and for determining and optimizing the ability of anti-Lynx antibodies to assist in the examination of the target cells are all well-known in the art.

More specifically, the diagnostic test kit may comprise:

(a) a known amount of the Lynx polypeptide as described above (or a binding partner or receptor) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the Lynx polypeptide to a detectable label;

(b) one or more additional immunochemical reagents of which at least one reagent is a ligand or an immobilized ligand, which ligand is selected from the group consisting of:

(i) a ligand capable of binding with the labeled component (a);
(ii) a ligand capable of binding with a binding partner of the labeled component (a);
(iii) a ligand capable of binding with at least one of the component(s) to be determined; and
(iv) a ligand capable of binding with at least one of the binding partners of at least one of the component(s) to be determined; and
(c) directions for the performance of a protocol for the detection and/or determination of one or more components of an immunochemical reaction between the Lynx polypeptide and a specific binding partner thereto.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the Lynx polypeptide may be radiolabeled and combined, for example, with antibodies or other inhibitors thereto, after which binding studies would be carried out. Solutions would then be prepared that contain various quantities of labeled and unlabeled uncombined lynx polypeptide, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex, most particularly a receptor/Lynx polypeptide complex. Thus, for example, if it is desired to evaluate a compound as a ligand for a particular receptor, or as a Lynx polypeptide or analog thereof, one of the plasmids would be a construct that results in expression of or activation of the receptor in the chosen cell line, while the second plasmid would possess a response element, promoter or gene linked to the luciferase gene. If the compound under test is an agonist for the receptor, the ligand will complex with the receptor, and the resulting complex will activate the response element promoter or gene and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

Therapeutic Applications

The therapeutic possibilities that are raised by the existence of the Lynx polypeptide, derive from the fact such polypeptides represent a novel family of receptor accessory molecules or ligands. In particular the Lynx polypeptides are capable of binding to or associating with a receptor or receptor molecule, whereby the activity or function of such receptor or receptor molecule is mediated or otherwise enhanced. More particularly, as provided by the Examples herein, Lynx 1 polypeptide, as characterized herein and set forth in SEQ ID NO:2 has been demonstrated to bind to or associate with nicotinic acetylcholine receptors, specifically through the alpha subunit of such receptors. In addition, Lynx1 is capable of mediating and enhancing the activity of its receptor, nAChR, as further provided herein. Thus, Lynx1 and its family of related Lynx polypeptides provide a means to new diagnostic and therapeutic approaches for monitoring and manipulating CNS system through its specific receptor, including but not limited to the cholinergic system.

Modulators of Lynx Polypeptides

In instances where it is desired to reduce or inhibit the effects resulting from the Lynx polypeptides of the present invention, an appropriate modulator, an inhibitor or activator, of the Lynx polypeptide could be introduced to block or enhance the activity of the Lynx polypeptide receptor. Thus, activators of Lynx1 polypeptides would be anticipated to activate or enhance nAChR function. These activators might be expected to mimic and/or enhance the activity of known nAChR modulators, for instance acetylcholinesterase inhibitors, now used as therapies for Alzheimer's disease. Also contemplated are analogs, agents or compound which mimic the activity of Lynx polypeptides and are capable of similarly mediating or enhancing the activity of Lynx polypeptide receptors.

The present invention contemplates screens for a modulator of a Lynx polypeptide. In one such embodiment, an expression vector containing the Lynx polypeptide of the present invention, or a derivative or analog thereof, is placed into a cell in the presence of at least one agent suspected of exhibiting Lynx polypeptide modulator activity. The cell is preferably a mammalian cell, most preferably a neural cell and most particularly a Purkinje cell. The amount of Lynx polypeptide modulator activity is determined and any such agent is identified as a modulator when the amount of Lynx polypeptide activity, or Lynx polypeptide receptor activity, in the presence of such agent is different than in its absence. The vectors may be introduced by any of the methods described above.

When the amount of Lynx polypeptide activity, or Lynx polypeptide receptor activity in the presence of the modulator is greater than in its absence, the modulator is identified as an agonist or activator of the Lynx polypeptide, whereas when the amount of activity in the presence of the modulator is less than in its absence, the modulator is identified as an antagonist or inhibitor of the Lynx polypeptide. As any person having skill in the art would recognize, such determinations as these and those below could require some form of statistical analysis, which is well within the skill in the art.

In accordance with the above, an assay system for screening potential drugs effective to modulate the activity of the Lynx polypeptide may be prepared. The Lynx polypeptide may be introduced into a test system, and the prospective drug may also be introduced into the resulting cell culture; and the culture thereafter examined to observe any changes in the Lynx polypeptide activity of the cells, due either to the addition of the prospective drug alone, or due to the effect of added quantities of the known Lynx polypeptide.

Natural effectors found in cells expressing Lynx polypeptide can be fractionated and tested using standard effector assays as exemplified herein, for example. Thus an agent that is identified can be a naturally occurring polypeptide modulator. Alternatively, natural products libraries can be screened using the assays of the present invention for screening such agents. Another approach uses recombinant bacteriophage to produce large libraries. Using the "phage method" [Scott and Smith, 1990, *Science* 249:386-390 (1990)]; Cwirla, et al., *Proc. Natl. Acad. Sci.*, 87:6378-6382 (1990): Devlin et al., *Science*, 249:404-406 (1990), very large libraries can be constructed (10'-10 chemical entities). Yet another approach uses primarily chemical methods, of which the Geysen method [Geysen et al., *Molecular Immunology* 23:709-715 (1986); Geysen et al. *J. Immunologic Method* 102:259-274 (1987)] and the method of Fodor et al. [*Science* 251:767-773 (1991)] are examples. Furka et al. [*14th International Congress of Biochemistry. Volume* 5, Abstract FR:013 (1988); Furka, *Int. J. Peptide Protein Res.* 37:487-493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested.

In another aspect, synthetic libraries [Needels et al., *Proc. Natl. Acad. Sci. USA* 90:10700-4 (1993); Ohlmeyer et al., *Proc. Natl. Acad. Sci. USA* 90:10922-10926 (1993); Lam et al., International Patent Publication No. WO 92/00252; Kocis et al., International Patent Publication No. WO 9428028, each of which is incorporated herein by reference in its entirety], and the like can be used to screen for such an agent.

This invention provides antagonist or blocking agents which include but are not limited to: peptide fragments, mimetic, a nucleic acid molecule, a ribozyme, a polypeptide, a small molecule, a carbohydrate molecule, a monosaccharide, an oligosaccharide or an antibody. Also, agents which competitively block or inhibit Lynx polypeptide are contemplated by this invention. This invention provides an agent which comprises an inorganic compound, a nucleic acid molecule, an oligonucleotide, an organic compound, a peptide, a peptidomimetic compound, or a protein which inhibits the polypeptide.

Pharmaceutical Compositions

The present invention further contemplates therapeutic compositions useful in practicing the therapeutic methods of this invention. A subject therapeutic composition includes, in admixture, a pharmaceutically acceptable excipient (carrier) and one or more of a Lynx polypeptide, an analog or fragment thereof, as described herein as an active ingredient. In a preferred embodiment, the composition comprises Lynx1 polypeptide as set forth in SEQ ID NO:2. In a more preferred embodiment, the composition comprises mature Lynx1 polypeptide, as set forth in SEQ ID NO: 4 lacking the signal sequence, and most preferably having GPI attached. Pharmaceutical compositions contemplated by the present invention further comprise soluble Lynx1 polypeptide, lacking the GPI attachment sequence. In a further embodiment, the composition comprises Lynx2 polypeptide as set forth in SEQ ID NO: 15.

This invention provides a pharmaceutical composition comprising an amount of the polypeptide as described and a pharmaceutically acceptable carrier or diluent. The invention further provides a pharmaceutical composition comprising an amount of the polypeptide of SEQ ID NO:2, including fragments, mutants, variants, analogs or derivatives thereof, and a pharmaceutically acceptable carrier or diluent.

The invention provides pharmaceutical compositions comprising an amount of the polypeptide of the present invention and an amount of acetylcholine, an acetylcholine-like compound, or another agent that enhances or otherwise increases the amount or concentration of acetylcholine at or near acetylcholine receptors, for instance an acetylcholinesterase inhibitor.

As an example, pharmaceutical compositions provided by the present invention include compositions for mediating nAChR activity which may include Lynx polypeptide, analogs or fragments thereof, or antibody to Lynx polypeptide.

The pharmaceutical compositions of the present invention may be administered alone or in combination with other CNS therapeutic compositions, such as, for example, acetylcholinesterase inhibitors or SSRIs.

This invention provides a method for treating or ameliorating cognitive, learning or memory disorders or deficits in a subject comprising administering to the subject an amount of the pharmaceutical composition effective to modulate activity of the Lynx polypeptide, thereby activating or inhibiting the Lynx polypeptide receptor.

This invention provides a method for treating or ameliorating cognitive, learning or memory disorders or deficits in a subject comprising administering to the subject an amount of a pharmaceutical composition comprising an anti-Lynx antibody and a pharmaceutically acceptable carrier or diluent.

This invention provides a method of treating or ameliorating cognitive, learning or memory disorders or deficits in a subject comprising administering to the subject an amount of the pharmaceutical composition comprising a polypeptide selected from the following: a Lynx polypeptide, the Lynx 1 polypeptide consisting of the amino acid sequence as set forth in SEQ ID NO:2, a mature Lynx polypeptide, a soluble Lynx polypeptide, or analogs or fragments thereof.

As used herein, "pharmaceutical composition" could mean therapeutically effective amounts of polypeptide products of the invention together with suitable diluents, preservatives, solubilizers, emulsifiers, adjuvant and/or carriers useful in therapy against bacterial infection or in inducing an immune response. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of the Lynx polypeptides and agents of the present invention. The choice of compositions will depend on the physical and chemical properties of the polypeptide. Controlled or sustained release compositions include formulation in lipophilic depots (e.g., fatty acids, waxes, oils). Also comprehended by the invention are particulate compositions coated with polymers (e.g., poloxamers or poloxamines) and the polypeptides of the present invention coupled to antibodies directed against tissue-specific receptors, ligands or antigens or coupled to ligands of tissue-specific receptors. Other embodiments of the compositions of the invention incorporate particulate forms, protective coatings, protease inhibitors or permeation enhancers for various routes of administration, including parenteral, pulmonary, nasal and oral. Further, as used herein "pharmaceutically acceptable carrier" are well known to those skilled in the art and include, but are not limited to, 0.01-0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from mucosal surfaces or the circulation and may therefore elicit relatively short-lived pharmacological activity. Consequently, frequent administrations of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Dosages. The sufficient amount may include but is not limited to from about 1 µg/kg to about 1000 mg/kg. The amount may be 10 mg/kg. The pharmaceutically acceptable form of the composition includes a pharmaceutically acceptable carrier.

As noted above, the present invention provides therapeutic compositions comprising pharmaceutical compositions comprising vectors, vaccines, polypeptides, nucleic acids and antibodies, anti-antibodies, and agents, to compete with the pneumococcus bacterium for pathogenic activities, such as adherence to host cells.

The preparation of therapeutic compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An active component can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. In the context of the present invention, a deficit in the response of the host is evidenced by continuing or spreading bacterial infection. An improvement in a clinically significant condition in the host includes a decrease in bacterial load, clearance of bacteria from colonized host cells, reduction in fever or inflammation associated with infection, or a reduction in any symptom associated with the bacterial infection.

According to the invention, the component or components of a therapeutic composition of the invention may be introduced parenterally, transmucosaily, e.g., orally, nasally, pulmonarailly, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Oral or pulmonary delivery may be preferred to activate mucosal immunity; since pneumococci generally colonize the nasopharyngeal and pulmonary mucosa, mucosal immunity may be a particularly effective preventive treatment. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

In another embodiment, the active compound can be delivered in a vesicle, in particular a liposome (see Langer, *Science* 249:1527-1533 (1990); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid).

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.* 23:61 (1983); see also Levy et al., *Science* 228: 190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in *Medical Applications of Controlled Release*, supra, vol. 2, pp. 115-138 (1984)). Preferably, a controlled release device is introduced into a subject in proximity of the site of inappropriate immune activation or a tumor. Other controlled release systems are discussed in the review by Langer (*Science* 249: 1527-1533. (1990)).

A subject in whom administration of an active component as set forth above is an effective therapeutic regimen for a bacterial infection is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

In the therapeutic methods and compositions of the invention, a therapeutically effective dosage of the active component is provided. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Administration with other compounds. For treatment of a CNS disorder or disease, one may administer the present active component in conjunction with one or more pharmaceutical compositions used, for instance, for treating cognitive or memory disorders, including but not limited to acetylcholinesterase inhibitors and serotonin reuptake inhibitors (SSRIs). Administration may be simultaneous (for example, administration of a mixture of the present active component and an SSRI), or may be in seriatim.

The preparation of therapeutic compositions which contain Lynx polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A Lynx polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of mediation desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the Lynx polypeptide, antagonist or analog thereof, and one or more of the following active ingredients: an antibiotic, a steroid. Exemplary formulations are given below:

Formulations

Intravenous Formulation I

| Ingredient | mg/ml |
| --- | --- |
| cefotaxime | 250.0 |
| Lynx polypeptide | 10.0 |
| dextrose USP | 45.0 |
| sodium bisulfite USP | 3.2 |
| edetate disodium USP | 0.1 |
| water for injection q.s.a.d. | 1.0 ml |

Intravenous Formulation II

| Ingredient | mg/ml |
| --- | --- |
| ampicillin | 250.0 |
| Lynx polypeptide | 10.0 |
| sodium bisulfite USP | 3.2 |
| disodium edetate USP | 0.1 |
| water for injection q.s.a.d. | 1.0 ml |

Intravenous Formulation III

| Ingredient | mg/ml |
| --- | --- |
| gentamicin (charged as sulfate) | 40.0 |
| Lynx polypeptide | 10.0 |
| sodium bisulfite USP | 3.2 |
| disodium edetate USP | 0.1 |
| water for injection q.s.a.d. | 1.0 ml |

Intravenous Formulation IV

| Ingredient | mg/ml |
| --- | --- |
| Lynx polypeptide | 10.0 |
| dextrose USP | 45.0 |
| sodium bisulfite USP | 3.2 |
| edetate disodium USP | 0.1 |
| water for injection q.s.a.d. | 1.0 ml |

Intravenous Formulation V

| Ingredient | mg/ml |
| --- | --- |
| Lynx polypeptide antagonist | 5.0 |
| sodium bisulfite USP | 3.2 |
| disodium edetate USP | 0.1 |
| water for injection q.s.a.d. | 1.0 ml |

As used herein, "pg" means picogram, "ng" means nanogram, "ug" or "µg" mean microgram, "mg" means milligram, "ul" or "µl" mean microliter, "ml" means milliliter, "l" means liter.

It is further intended that Lynx polypeptide analogs may be prepared from nucleotide sequences of the protein complex/subunit derived within the scope of the present invention. Analogs, such as fragments, may be produced, for example, by pepsin digestion of Lynx polypeptide material. Other analogs, such as muteins, can be produced by standard site-directed mutagenesis of Lynx polypeptide coding sequences. Analogs exhibiting "Lynx polypeptide activity" such as small molecules, whether functioning as promoters or inhibitors, may be identified by known in vivo and/or in vitro assays.

As mentioned above, a DNA sequence encoding Lynx polypeptide can be prepared synthetically rather than cloned. The DNA sequence can be designed with the appropriate codons for the lynx polypeptide amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature,* 292:756 (1981); Nambair et al., *Science,* 223:1299 (1984); Jay et al., *J. Biol. Chem.,* 259:6311 (1984).

Synthetic DNA sequences allow convenient construction of genes which will express Lynx polypeptide analogs or "muteins". Alternatively, DNA encoding muteins can be made by site-directed mutagenesis of native Lynx genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science,* 244:182-188 (April 1989). This method may be used to create analogs with unnatural amino acids.

The present invention extends to the preparation of antisense oligonucleotides and ribozymes that may be used to interfere with the expression of the Lynx polypeptide at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990: Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into Lynx polypeptide-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahymena-type and "hammerhead"-type. (Hasselbhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for Lynx polypeptide and their receptors.

The present invention further extends to animals, particularly transgenic animals, wherein the expression of Lynx protein or the Lynx gene is altered or enhanced. In particular, transgenic animals with genetic alterations in the dosage of a Lynx gene are contemplated. Still more particularly the invention extends to transgenic animals expressing a soluble version of the Lynx protein. In a particular embodiment, the soluble version of Lynx protein lacks a C-terminal GPI attachment sequence, but contains a signal sequence. Transgenic animals wherein the gene or genes encoding Lynx protein are knocked-out (knock-out mice) or mutated are also contemplated.

The animals, particularly transgenic animals, of the present invention may be utilized in a variety of studies and applications, including but not limited to the assessment of the role and function of Lynx polypeptides or Lynx analogs, the screening or assessment of Lynx modulators, activators, or inhibitors, the screening or assessment of nicotinic acetylcholine receptor modulator compounds, the screening or assessment of acetylcholine or acetylcholinesterase modulators, or the evaluating therapeutics for the treatment of CNS diseases, including modulators of memory or Alzheimer's disease.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Cloning and Characterization of Lynx1

The correct circuitry of the mature brain requires precise synaptic connections between afferent cells and their target neurons. This is established during the final phase of neuronal development by pruning of supernumerary, immature synaptic contacts and segregation of afferent inputs to distinct target cell subdomains (Katz, L. C. & Shatz, C. J. (1996) Science 274, 1133-1138). The molecular mechanisms participating in this final phase of synaptic maturation are largely unknown. This Example details the identification of a novel ligand/receptor pair localized to synaptic partners late in neuronal development. The ligand, Lynx1, is a new member of the Ly-6/α-bungarotoxin gene superfamily whose members contain a structural receptor binding motif characteristic of the neuroactive snake venom toxins, termed the three-fingered or toxin fold. Lynx1 is neuronal cell surface protein, specifically a GPI-anchored protein, and is expressed in the deep nuclei of the cerebellum, localized to discrete subfields of large projection neurons in several brain structures, including the soma and proximal dendrites of Purkinje neurons. Binding of a Lynx1 fusion protein to sections from mouse cerebellum demonstrates that Lynx1 binds or associates to a molecule, its putative receptor, expressed in inhibitory neurons that are synaptic partners of Purkinje cells. The localization of the putative Lynx1 receptor to cells providing afferent input to Lynx1-expressing cells indicates that the Lynx1/Lynx1 receptor system may play an important role in the maturation of specific synapses in the mammalian brain.

The development of mature CNS connectivity is a complex process that unfolds in a series of steps which require a variety of molecular cues to guide an axon to its appropriate field and to initiate the signaling pathways responsible for interaction of the pre- and postsynaptic neuron (Tessier-Lavigne, M. & Goodman, C. S. (1996) Science 274, 1123-1133; Sanes, J. R. (1998) in Mechanistic Relationships Between Development and Learning, Carey, T. J. et al., eds, John Wiley and Sons, New York). While many molecules that play critical roles in these processes have been identified (Dresher, U. et al (1995) Cell 82, 359-370; Serafini, T. et al (1994) Cell 78, 409-424; Kolodkin, A. K. et al (1993) Cell 75, 1389-1399; Luo, Y. et al (1993) Cell 75, 217-227; Cheng, H. & Flanagan. J. G. (1994) Cell 79, 157-168) proteins that participate in the selectivity of synapse formation after initial target selection, or in the pruning and consolidation of immature synapses during the final phase of circuit maturation, are largely unknown (Cowan, W. M. (1998) Neuron 20, 413-426). To begin a molecular investigation of these phenomena, the identification of a CNS-specific gene regulated late in neuronal differentiation was needed. One such clone, GC26, was isolated in a screen for novel, developmentally regulated cDNAs expressed in the mouse cerebellum (Kuhar, S. G. et al (1993) Development 117, 97-104). GC26 mRNA expression is low at birth, is strongly induced in the second and third postnatal weeks, and reaches its adult level of expression within the first postnatal month. To begin to assess its function, the full-length cDNA of 4.1 kb was isolated (SEQ ID NO: 1) and a short (300 bp) open-reading frame (ORF) was identified (FIG. 1). The predicted amino acid sequence from this ORF encodes a protein of 11 kD, containing an N-terminal signal sequence and a hydrophobic domain at the C-terminus and critical residues matching the consensus for addition of a GPI anchor. (FIG. 2A, SEQ ID NO.: 2) (Udenfriend, S. et al (1995) Ann. Rev. of Biochem. 64, 563-591). The identification of the ORF was confirmed by in vitro translation, which yielded an approximately 11 kD. polypeptide.

Database searches (using Advanced Blast Search at www.ncbi.nlm.nih.gov) (Altschul, S. F. et al (1990) J. Mol. Biol. 215, 403-410) revealed a low level of amino acid homology (20-50% similarity) with a family of small cysteine-rich proteins comprising the Ly-6 GPI-linked cell surface accessory molecules of the immune system (Fleming, T. J. et al (1993) J. Immunol. 150, 5379-5390; Gumleyu, T. P., et al (1995) Immunol. Cell Biol. 73, 277-296) and the secreted elapid snake venom neurotoxins (Strydom, D. J. (1979) in Handbook of Experimental Pharmacology, Lee, C.-Y ed, Springer Varlag, New York). Alignment of GC26 with the Ly-6 proteins and the snake neurotoxins (FIG. 2B) demonstrated that GC26 contains the conserved cysteine motif that characterizes this gene family, prompting us to rename the GC26 polypeptide Lynx1 (Ly-6/neurotoxin). This motif consists of multiple cysteine residues involved in crucial internal disulfide bonding. The conserved motif spans the length of the mature protein, with a LeuXCysXXCys (LXCXXC) motif at the N-terminus, a charged residue (Met/Glu/Gln/Arg) at position 2 of the mature protein, and an aromatic residue (Phe/Tyr/His) at position 4. In addition, a highly conserved sequence of Cys CysXXXLeuCysAsn (CCXXX-LCN) is located at the C-terminal portion of the mature protein.

Further evidence of an evolutionary relationship between Lynx1 and members of this superfamily is provided by similarities in gene structure, specifically, similarity in the exon boundaries (Gumley, T. P. et al (1995) *Immunogen.* 42, 221-224). The translation start is coded in the first exon, which contains most of the signal sequence. The next exon contains the last amino acids of the signal sequence and the amino-terminal portion of the mature protein. The last exon contains the rest of the mature protein, a translation termination signal and a signal for GPI anchor biosynthesis which is cleaved during the GPI attachment process. While the length of the introns vary widely among the Ly-6 family members, there is a high degree of similarity in the exon boundaries, as is seen in Lynx1.

In addition, we have demonstrated tight linkage of the Lynx1 mouse locus to the Ly-6 gene cluster (Gumley, T. P. et al (1995) *Immunol. Cell Biol.* 73, 277-296; Hart, C. P. et al (1992) *J. Exp. Zool.* 263, 83-95). The Ly-6 family of genes are genetically linked to the 15E region of the mouse chromosome, with 18 independent genes and/or pseudogenes with strong Ly-6 homology clustered in an approximately 600 Kb region (Kamiura et al (1992) *Genomics* 12, 889-105). The murine chromosomal location of Lynx1 was localized to the middle region of mouse chromosome 15, tightly linked to the Ly-6 gene cluster.

Members of the Ly-6/α-bungarotoxin gene superfamily function through interactions with specific receptors (Strydom, D. C. (1979) in *Handbook of Experimental Pharmacology*, Lee, C.-Y ed, Springer Varlag, New York; Stiles, B. G. (1993) *Toxicon* 31, 825-834). Ly-6 proteins act through cell surface receptors to participate in lymphocyte homing (Hanninen, A. et al (1997) *Proc. Natl. Acad. Sci. USA* 94, 6898-6903) suggesting that these proteins are important for specific cellular recognition functions. Elapid snake venom neurotoxins exert their toxic effects through high affinity interactions with receptors in the mammalian nervous system. For example, α-bungarotoxin (α-Btx) has been shown to inhibit nicotinic acetylcholine receptors by binding to the α7 subunits (Chen, D. & Patrick, J. W. *J. Biol. Chem.* 272, 24024-24029), whereas the M3 toxin inhibits muscarinic receptors (Jolkkonen, M. et al (1994) *FEBS LETT.* 352, 91-94). Structural data for CD59, α-Btx, and cobratoxin demonstrate a strikingly similar tertiary structure, adopting a three-looped beta sheet structure referred to as the three-fingered or "toxin fold" (Fletcher, C. H. et al (1994) *Structure* 2, 185-199; Basus, V. J. et al (1993) *Biochem.* 32, 12290-12298; LeGoas et al (1992) *Biochem.* 31, 4867-4875). The topology of these molecules is dictated by the formation of disulfide bonds between the critical cysteine residues that constitute the Ly-6/α-Btx consensus motif (Gumley, T. P. et al (1995) *Immunol. Cell Biol.* 73, 277-296; Harrison, P. M. & Sternberg, J. E. (1996) *J. Mol. Biol.* 264, 603-623). The conservation of these critical cysteine residues in Lynx1 (FIG. 2A), and the prediction of the presence of the "toxin fold" in Lynx1 by energy minimization molecular modeling studies (data not shown), suggest that Lynx1 might function through interactions with a receptor.

To gain insight into the possible significance of Lynx1 in the CNS, its expression pattern was examined. Northern blot analysis demonstrated that Lynx1 mRNA is enriched in the brain, and is not present in the immune system (FIG. 3A). Northern blot analysis at various stages of cerebellar development demonstrate that Lynx1 is expressed at very low levels at birth, and undergoes a marked up regulation, between post-natal days 10 and 20 (Kuhar, S. G. et al. (1993) *Development* 117, 97-104). In situ hybridization to adult brain sections revealed that Lynx1 is highly expressed in subsets of neurons in multiple brain structures (FIG. 3B), including Purkinje cells and deep nuclei neurons of the cerebellum (panels a,b), deep layer pyramidal neurons in the cerebral cortex (panel d). CA3 pyramidal neurons of the hippocampus (panel e), and mitral cells of the olfactory bulb (panel f). Although these neurons are otherwise unrelated, they share the characteristic that they participate as highly integrative output neurons in their respective brain structures, often segregating multiple afferent synapses into distinct subcellular domains. The late onset of expression of the Lynx1 gene, occurring during the final stages of development of the cerebellum, precludes participation of Lynx1 in events such as neural induction or neuronal migration, suggesting a role in later events such as synaptogenesis or synapse maturation.

To determine the subcellular localization of the Lynx1 protein, polyclonal antiserum raised against a Lynx1 peptide was used to perform immunocytochemical analysis on sections of adult mouse brain. A Lynx1 peptide, corresponding to amino acids TTRTYFTPYRIMKVRKS (SEQ ID NO.: 3), representing the second loop or "toxinfinger" and a recognized antigenic region in Ly-6 superfamily members, was used to immunize rabbits and generate polyclonal antibody to Lynx1, as described in Methods below. Immunocytochemical analysis with anti-Lynx1 polyclonal antiserium confirmed the restricted pattern of expression first observed by in situ hybridization, and further revealed that Lynx1 is localized to subdomains within individual neurons (FIG. 4). This is most clearly illustrated by analysis of the cerebellar Purkinje cell, which has an elaborate dendritic tree that is compartmentalized into discrete subdomains defined by segregated afferent types (Larramendi, L. M. H. & Viktor, T. (1967) *Brain. Res.* 5, 15-30). One such subdomain, the fine, spine-bearing branchlets emanating from distal dendrites, is preferentially contacted by excitatory parallel fiber terminals. A second subdomain, the proximal dendrite and soma, is the target of inhibitory afferents of the local interneurons, the stellate and basket neurons. Immunostaining with the anti-Lynx1 antisera reveals that Lynx1 is present in the soma and proximal dendrites in Purkinje neurons (FIG. 4, panels A,C), in contrast to that of anti-calbindin antisera, which labels the entire dendritic arbor (FIG. 4, panel D). Double label immunofluorescence with these antisera illustrates this differential localization within single neurons (FIG. 4, panel E). Colocalization of inhibitory, afferent synapses and Lynx1 reveals the distribution of inhibitory synaptic termini closely apposed to Lynx1 positive post-synaptic domains (FIG. 4, panel F). Thus Lynx1 expression appears to be restricted to a subdomain of target neurons that correlates with the distribution of a defined subset of afferent inputs.

Figure 5C:
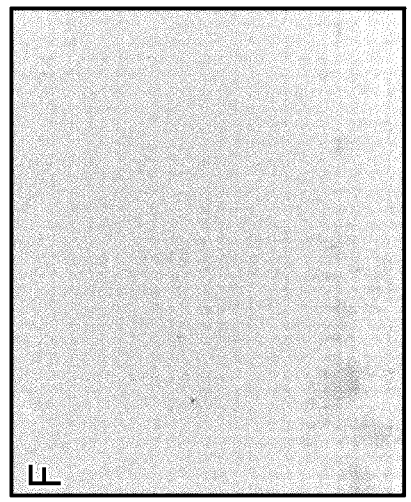
FIG. 5B-5F, Affinity binding assays localize the Lynx1 receptor to inhibitory interneurons of the cerebellar cortex. B, Binding of Lynx/Fe fusion protein is detected in Purkinje cells and in stellate neurons (indicated by arrows) which are presynaptic to the Purkinje cell. C, Binding with Lynx/AP shows a similar result. D-F, Preincubation with recombinant Lynx1 demonstrates the specificity of this binding interaction. D, The unfused Fe control, shows no specific labeling. E, In the presence of BSA, Lynx/Fe shows binding to Purkinje cell dendrites and stellate neurons in the cerebellar cortex. F, Preincubation with recombinant Lynx1 specifically inhibits the binding of the Lynx1/Fc fusion protein.
Figure 5F:
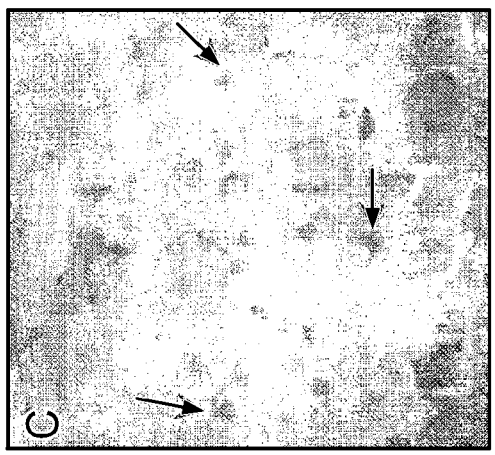
Figure 5B:
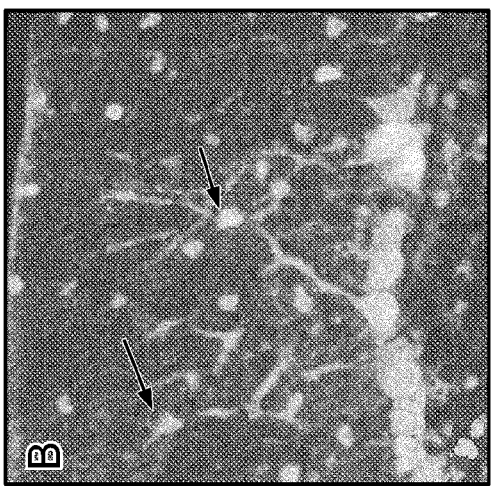
Figure 5E:
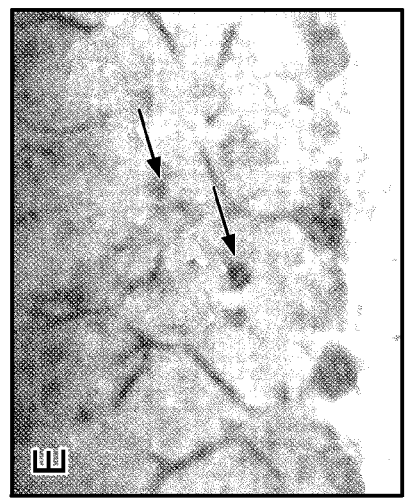
Figure 5A:
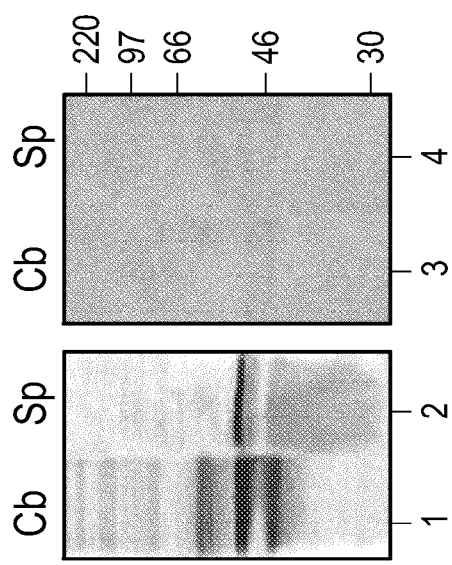
FIG. 5A is a Far Western blot showing that Lynx/AP fusion protein recognizes a specific band in cerebellar extracts. Binding of Lynx/AP on a Far Western blot of extracts from cerebellum (lanes 1,3) and spleen (lanes 2,4). Lanes 1,2 were reacted with Lynx/AP. Lanes 3,4 were reacted with unfused AP control.
Figure 5D:
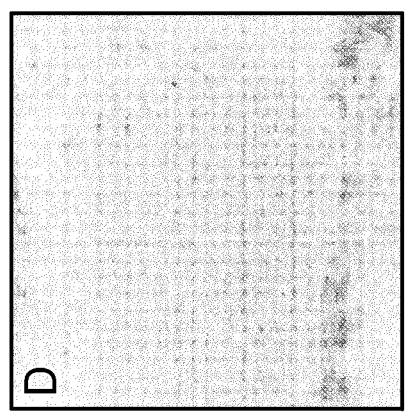

The known receptor binding properties of the Ly-6/α-bungarotoxin family of proteins led to the investigation of Lynx1 function as a possible CNS ligand. To assess whether Lynx1 functions through interactions with a specific receptor, ligand affinity probes were generated by cloning Lynx1 in frame with both the Fc fragment of human IgG (Lynx/Fc) and alkaline phosphatase (Lynx/AP). These fusion proteins specifically recognized a single band of approximately 50 kD in cerebellar extracts by Far Western analysis (FIG. 5A). To localize Lynx1 receptor sites, these fusion proteins were used to perform affinity binding assays on sections of adult cerebellar tissue (FIG. 5B-5F). Binding of Lynx1 was detected in the Purkinje cell soma, as well as in basket and stellate neurons resident in the molecular layer of the cerebellar cortex, the inhibitory afferents to Purkinje cells. In competition experiments, preincubation of cerebellar sections with an excess of recombinant Lynx1 protein blocked the specific binding of the Lynx/Fc fusion protein (FIG. 5E), whereas preincubation in the presence of excess bovine serum albumin had no effect (FIG. 5D), demonstrating the specificity of this interaction. These data indicate that Lynx1 functions through interactions with a specific 50 KD molecule, putatively a CNS receptor, present in neurons presynaptic to Lynx1-expressing cells. The evidence presented in this study identifies a novel ligand/receptor pair that is expressed in synaptic partners in the mature CNS. Several initial observations suggest that Lynx1 could contribute to the specificity of synaptic connections in the brain. First, the late up-regulation of Lynx1 and its maintenance in adulthood is consistent with its involvement in the latest developmental events, such as the consolidation of mature circuitry. Second, the fact that snake venom neurotoxins form a three-fingered fold which binds with very high avidity to specific receptors in the nervous system (Stilels, B. G. (1993) *Toxicon* 31, 825-834), and that Lynx1 contains the critical residues dictating formation of a three-fingered fold, support the idea that Lynx1 function is achieved through specific receptor interactions. Further analyses demonstrate localization of Lynx1 to a subdomain of Purkinje cells and other neurons that correlates with the distribution of a defined subset of afferent inputs. Finally, the identification of a putative Lynx1 receptor, and its localization to inhibitory neurons that provide afferents to cells expressing Lynx1, suggests that the Lynx1/Lynx1 receptor system acts to identify synaptically linked neurons. Lynx1 expression appears to identify a specific subdomain in target neurons that is utilized by Lynx1 receptor bearing afferents. Binding of Lynx1 to its receptor is therefore likely to be an important step in the establishment or maintenance of specific synaptic interactions.

Methods:

cDNA library screening. Library screening was conducted on an oligo-dT primed lambda zap cDNA library synthesized from adult murine cerebellar RNA, using an 1.5 kb Sfi1-Not1 fragment from the GC26 cDNA depicted in FIG. 1. The predicted amino acid of mature Lynx1 protein (lacking the signal sequence and after GPI attachment and cleavage), as shown in the first line as "lynx1" in FIG. 2B (SEQ ID NO.: 4) was used in Genbank searches under tblastn, and blastp search algorithms, using PAM250 and default parameters. Amino acid sequence alignments were performed using the ClustalW algorithm (MacVector). FIG. 2B provides a tabulation of the search results and alignment.

Northern Blot. Tissue was dissected and frozen in liquid nitrogen, RNA was extracted in guanidinium-thiocyanate according to standard methods. PolyA+ RNA was purified oligo-dT chromatography. 5 µg of RNA were electrophoretically separated, blotted onto Genescreen nylon membrane, and probed overnight at 42° C., washed at a stringency of 0.5×SSC, 0.1% SDS at 65° C. The probe was made by random primed labeling of a 500 bp EcoRI fragment corresponding to the open reading frame of the Lynx1 cDNA.

In situ hybridization. Radioactive in situ hybridization analyses were conducted on 10 µm fresh frozen sections of adult mouse brain. An 1.5 kb. Sfi1-Not1 fragment of the 3' UTR region was used for these experiments. One million counts of $^{35}$S-labeled riboprobe were applied to each section and washed to a stringency of 0.1×SSPE at 65° C. The slides were exposed and developed under standard conditions, and counterstained with cresyl violet.

Immunocytochemistry. Peptide antibodies were generated from the peptide sequence: TTRTYFTPYRMKVRKS (SEQ ID NO.: 3), corresponding to the second "toxin finger". Adult mouse brains were perfused with 4% paraformaldehydehyde/PBS, sunk in 30% sucrose/PBS, and sectioned at 20 µm on a freezing microtome. The sections were blocked with 10% NGS, 0.05% Triton-X in PBS, incubated in Lynx1 antiserum at 1:8,000 or Calbindin antibodies (Swant) at 1:10,000. Antibody binding was visualized using the ABC Elite kit (Vector) according to manufacturer's instructions.

Immunofluorescence. Sections were prepared as above. The Lynx1 antiserum was used at 1:2000, and detected with goat anti-rabbit secondary antibody conjugated to Cy3 (Jackson Immunochemicals). Double labeling with anti-GAD was perfumed at 1:1000 (Boerhinger Mannheim), and detected with goat anti-mouse Cy5 at 1:800 (Jackson Immunochemicals). Labeling was imaged on a scanning laser confocal microscope (Zeiss)

Far Western Analysis. A fragment of the Lynx1 cDNA corresponding to the mature polypeptide was cloned in frame to the C-terminus of the coding sequence for the secreted human placental alkaline phosphatase (referred to as Lynx/AP). The APtag-4 vector was provided by Dr. John Flanagan (Cheng, H.-J. et al (1995) *Cell* 82, 371-381). Constructs were transfected into 293T cells using calcium phosphate precipitation. Conditioned media was collected and treated as described (Cheng, H.-J. et al (1995) *Cell* 82, 371-381): 20 µg of crude extract was electrophoretically separated and transferred to PVDF membrane (Immobilon P, Millipore). Filters were renatured as specified (Rodriguez, P. L. & Carrasco, L. (1994) *Biotech.* 17, 702-707), incubated overnight with equal amounts of cultured supernatants containing lynx/AP or unfused AP, washed, and treated with NBT/BCIP substrate according to manufacturer's directions (Pharmacia). To determine the relative activity of Lynx/AP protein compared to unfused AP, a dilution series of cultured supernatants was blotted onto nitrocellulose paper with a slot blot apparatus and reacted for AP activity. The unfused AP control demonstrated at least a 10-fold excess of protein and activity levels over the Lynx/AP fusion protein, as determined by slot blot analysis.

Affinity Binding Assay. The Lynx1 cDNA corresponding to the mature lynx1 protein with its native signal sequence was cloned in frame 5' to the Fc portion of human IgG (Lynx/Fc). The control used was a secreted, unfused Fc construct. Constructs were transfected and treated as above, then concentrated 1:20 in an Ultrafree-Biomax spin column (Millipore). The Lynx1 fusion protein was normalized against the control by Western analysis. Binding experiments were performed on vibratome sections of perfused mouse brains (as above). The sections were blocked in 10% NGS in PBS, reacted with Lynx/Fc for 1 hour, and washed. Lynx/Fc binding was detected with biotinylated goat anti-human antibody at 1:1000 and detected with the ABC Elite kit (Vector), or with goat anti-human Cy3 at 1:1000 (Jackson Immunochemicals), and detected by epifluorescence microscopy. Lynx/AP receptor binding assays were: detected with anti-human AP rabbit antibody at 1:50 (Zymed) and detected with the ABC Elite kit (Vector).

Example 2

Genetic Analyses of Lynx1 Function in Motor Performance and Learning

The experimental objective of the following studies was to utilize genetic analyses to determine the function of the Lynx1 gene and its encoded protein in motor performance and learning. The initial cloning and characterization of the Lynx1 gene has indicated an involvement of Lynx1 in receptor interactions at specific synapses. The late up-regulation of this gene occurs during a period of synaptic instability, when circuits are maturing from crude initial circuitry by an experience-dependent mechanism. Structural analysis and binding assays show that Lynx1 interacts with its receptor in neurons presynaptic to Lynx1-expressing cells, in particular inhibitory inputs impinging onto integrative output neurons. These data indicate that Lynx1 has an important role in the weighting of inhibitory inputs in these circuits. Alterations in dosage of Lynx1, then, might have an effect on synaptic transmission, and weighting of inhibitory inputs.

The focus for this analyses was on the cerebellar Purkinje cell for several reasons: the cerebellar Purkinje cell is a highly integrative cell, which segregates its many afferent inputs into discrete subdomains. Protein localization analyses on this cell type has allowed us to determine that the Lynx1 protein is restricted to a dendritic subdomain that is correlated with a defined set of afferent inputs, in particular the inhibitory stellate and basket neurons. In addition, the Lynx1 receptor is localized to the inhibitory stellate and basket neurons of the cerebellar cortex, which make preferential contact near the Purkinje cell soma. This finding has important implications for neuronal signaling in the cerebellar circuit.

The Purkinje cell is the main output neuron in the cerebellar cortex, and sends inhibitory signals to the deep nuclear neurons of the cerebellum. The main function of the cerebellar circuit is to refine the activity of the "primary" cerebellar circuit, from brainstem regions to deep nuclei and out to other body regions. The Purkinje cell assesses signals from two main sources—the climbing fibers emanating from the brainstem onto the proximal dendritic shafts of the Purkinje cell, and the parallel fibers arising from the local interneuron, the cerebellar granule cell, which makes preferential contacts onto spines of the distal dendritic branchlets of the Purkinje cell dendritic arbor. Mechanisms underlying associative learning in the cerebellum, have demonstrated that it is correlated activity from these two main inputs which are responsible for long-lasting changes in the behavior of the Purkinje cell. The inputs from the inhibitory stellate and basket neurons are in a unique position to affect the temporal correlation of these two afferent inputs. Interestingly, synaptic alterations during the pairing of stimuli of these two inputs can be induced only through the removal of inhibition, indicating a strong effect that inhibitory inputs have on this cellular mechanism.

Genetic alterations in the dosage of the Lynx1 gene then allows the determination of the role that this protein has in synaptic transmission, and in synapse consolidation during circuit maturation. In addition, at a higher level of analysis, it should allow the determination of the role of inhibition in the function of the cerebellar cortical circuit, and the determination of the role that this inhibition has in synaptic mechanisms underlying associative learning in this structure.

Experimental Design:

Transgenic animals were made carrying a Lynx1 gene encoding a soluble version of the Lynx1 protein, under the control of the L7 promoter, a promoter driving expression in cerebellar Purkinje cells. The soluble version of Lynx1 contains the signal sequence, but lacks the C-terminal GP1 attachment sequence and comprises amino acids 1-91 of SEQ ID NO.: 2, cloned in frame to the pcp2(L7) Purkinje cell specific promoter in expression vector pCEVII. This promoter has been used successfully by others to drive highly restricted expression in cerebellar Purkinje cells (Hashimoto et al., (1996) *Hum. Gene Ther* 7, 149-158; DeZaenw, C. I. et al., (1998) *Neuron* 20, 495-508). The construct was introduced into Cba/C57 Black hybrid mice by DNA injection into embryos using standard transgenic techniques.

Progeny of the positive transgene carrying founders were tested from 7-12 weeks of age. Testing was conducted on age and sex matched littermate controls. Transgenic animals were tested for performance in a rotarod test (Brandon, E. P. et al., (1998) *J. Neuroscience* 18, 3639-3649). In this test, the parameter analyzed was the number of seconds an animal was able to run upright on the rotarod without falling or wrapping around on the bar. Testing parameter were 8 trials per day over a period of 6 days. An accelerated paradigm was used, with an initial speed of 4 RPM, and accelerations of 1 RPM/second and 0.4 RPM/second.

Statistical analysis was performed on these data by averaging the eight trials for each day for each animal, and comparing these values between transgenic animals and wild type controls.

Figure 6B:
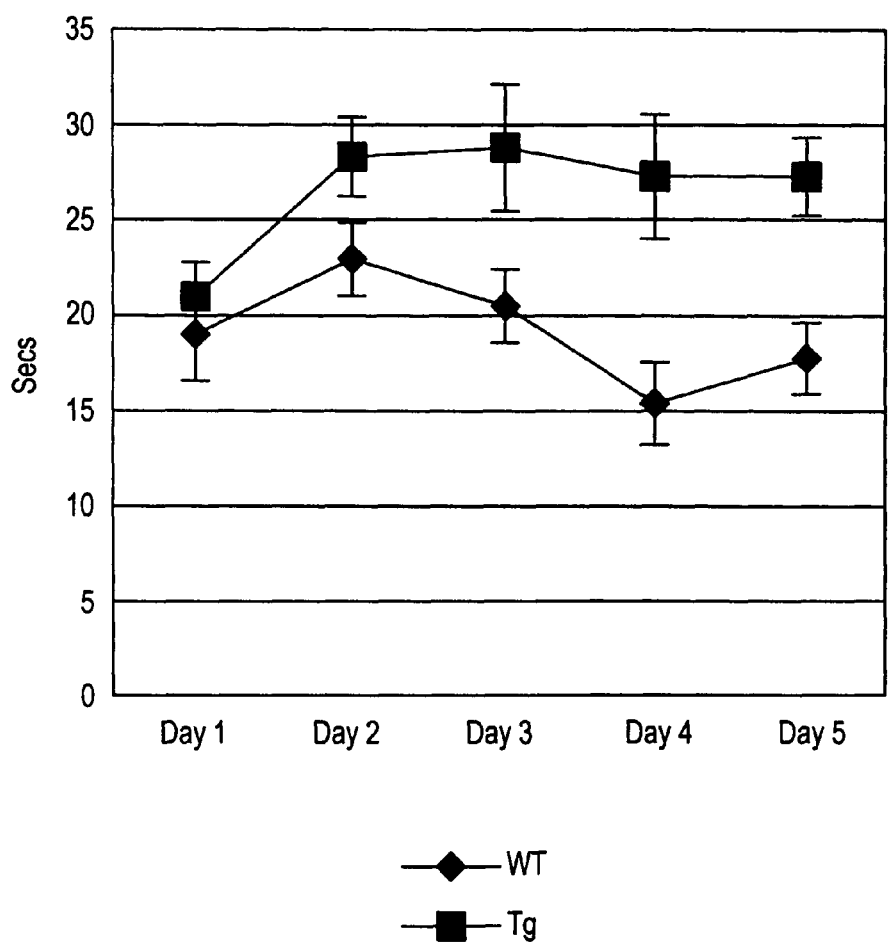
Figure 6C:
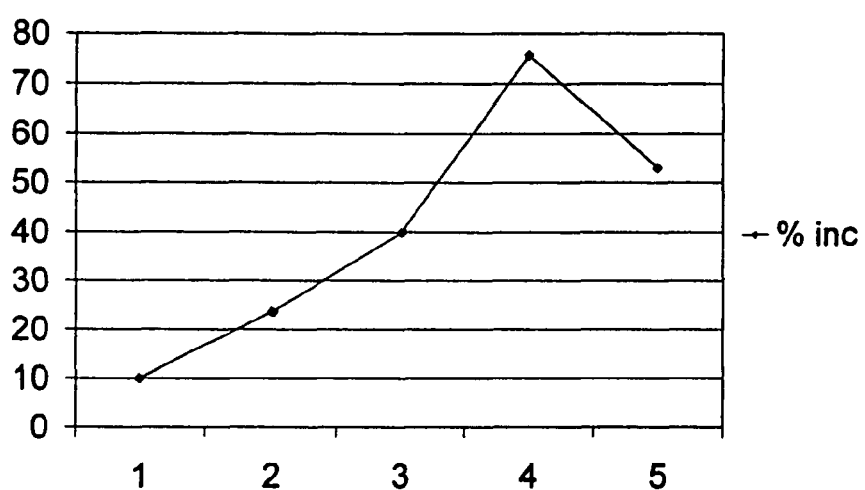

Results:

In animals 7-10 weeks of age, transgenic animals showed an increase in ability over a five day testing period versus wild type animals, whereas no significant differences were observed between transgenic animals and wild type animals on the initial day of testing. The data from these animal tests are shown in FIG. 6A-6C. At the fourth day of testing, the transgenic animals showed a greater than 75% increase in ability over the wildtype controls. On a student T test data this corresponded to showed a p value of 10E-08. (Values lower than 0.05 are considered statistically significant). At six days of testing, transgenic animals decreased to 60% enhancement over wild-type controls.

In animals 12 weeks of age or older, there was a slight increase in ability in rotarod performance on the initial day of testing, and no increase in ability over the training period.

Conclusions:

Transgenic animals overexpressing soluble Lynx1 show an age-dependent increase in the ability of animals to learn to perform the rotarod task. This preliminary data suggests that the Lynx1 transgene is causing a reduction in inhibition impinging on the Purkinje cell. The data are consistent, in that there is evidence in the literature that inhibition from stellate cells are important for learning in the cerebellum, and blockade of inhibition is usually necessary for the expression of synaptic changes in long term depression (LTD), a form of learning in the cerebellum, in vivo. This data is also consistent with an involvement of Lynx1 in cholinergic signaling, mediated by acetylcholine receptors, which occurs throughout the cerebellum, particularly in the stellate and basket cells. Evidence in the literature has demonstrated that cholinergic inputs effect learning in the cerebellum and other brain regions.

It is likely that the Lynx1 gene acts through some receptor mechanism, most plausibly the cholinergic pathway, to alter the general excitability of inhibitory neurons, and as a consequence, excitability of the Purkinje cell. One plausible mechanism is that alteration in Lynx1 dosage potentiates synaptic responding, altering the weighting needed to reach threshold in response to input from other sources, i.e. changes the gain of the Purkinje cell. This change in gain in inhibition, located between the parallel fiber and climbing fiber sources, could have a critical impact on the threshold for correlation during an associative learning task. Therefore, through this genetic modification, the threshold may have lowered for correlation needed to produce a long-lasting change in synaptic strength. This could have strong implications on the amount of training needed to produce learning, the rate, and the amount of learning of this task.

The preliminary evidence described here indicates that Lynx1 functions as a positive modulator of acetylcholine receptor activation. Cholinergic pathways have been implicated in learning mechanisms, and it has been postulated that acetylcholine activation during learning tasks lowers the threshold for coincidence for learning to take place. The animal data is consistent with this model, in that fewer trials are needed in the transgenic animals before learning takes place. If Lynx1 acts as a positive modulator for the acetylcholine receptor, then it could further potentiate acetylcholine currents during training and allow learning to occur at an accelerated rate.

Learning may be due to a general increase in excitability, and may be associative. Animals, particularly older animals, may show a general increase in motor activity that could account for enhancements in learning. In the case of an activity that is natural to the animal in the cage, one might expect training to occur prior to any testing: older animals show an increased ability on the first day of testing on the rotarod, than did younger animals which showed no differences in innate ability to perform the rotarod task. This suggests some overlap in the circuitry necessary for rotarod performance and for running around in the cage. A variety of activity assays can be performed on naïve animals to test for general affects on excitability and hyperactivity, e.g. the open-field test would be appropriate to test this. In order to more fully test learning without the influence of general activity on task performance, it would be necessary to find learning tasks in which the circuits to be trained are least likely to be activated by natural stimuli or previous experience. In addition, as in all learning tasks, the conditioned and unconditioned stimuli and the response must be natural to the animal—in the repertoire of normal behavior for that animal. In an associative paradigm such as eye-blink conditioning, the behavioral response is natural for the animal, but the conditioned stimuli is unlikely to be naturally paired with the conditioned response, and so those circuits involved are less likely to be affected in the initial day of testing.

Additional tests for latency of learning include testing animals 1-2 weeks after the training period has ended, to assess the amount of enhancement in ability. These tests determine whether animals forget this task at the same rate, or whether transgenic mice remember longer.

To test mechanism of action, pharmacological doses of Lynx1 protein can be infused into mice a short time (i.e. 1-2 days) prior to testing. This discriminates between a developmental effect of the protein, in terms of rearranging neural circuitry or amount of synapse elimination, vs. a short term neuromodulatory effect and is also important in further assessment of therapeutic and pharmaceutical applications of Lynx1 in diseases or deficits where memory or learning are altered or affected.

Example 3

Lynx1 Binds to the Alpha Subunit of Nicotinic Acetylcholine Receptors and Enhances Acetylcholine-Mediated Effects As described above, the transgenic animal data of Example 2 is consistent with an involvement of Lynx1 in cholinergic signaling which occurs throughout the cerebellum, particularly in the stellate and basket cells. Evidence in the literature has demonstrated that cholinergic inputs effect learning in the cerebellum and other brain regions. The likelihood that the Lynx1 gene acts through some receptor mechanism to alter the general excitability of inhibitory neurons is further shown above in Example 1. In addition, in Example 1, the far western analysis showed that Lynx/FC and Lynx/AP fusion proteins specifically recognized a single band of approximately 50 kD in cerebellar extracts. Interestingly, this size corresponds to that of the alpha subunit of nicotinic acetylcholine receptors, and as detailed above, aBTx has been shown to bind to the alpha subunit. The 50 kD far western band cornigrates with alpha 7 nAChR subunit, as demonstrated by performing a side-by-side Western with antibody against alpha 7 subunit and the Far Western on brain extract with the Lynx/AP fusion as a probe. In order to more fully determine whether Lynx1 protein was capable of binding to the alpha subunit of the nAChR, the following studies were performed:

A. Lynx1 Protein Binds to nAChR Alpha Subunit Expressed in Mammalian 293 Cells

Mammalian 293T cells, which do not express endogenous nAChR subunits, were transfected with an alpha 7 subunit expression construct (chick alpha 7 construct). The cells were harvested and lysed and cell extract was run out on an SDS-PAGE gel. A Far Western was performed using Lynx/AP as a probe as previously described and identified a band corresponding in size to the alpha 7 subunit in alpha 7 transfected cells but not in control 293T cells transfected with a control green fluorescent protein (GFP) construct.

B. Lynx1 Identifies Alpha Subunit Expression Library Clones

Lynx/AP fusion protein containing supernatant was prepared by transfecting the Lynx/AP fusion construct into 293T cells and incubating for three days. The Lynx/AP supernatant was used as a probe to screen a Lambda phage expression library, with positives identified using NBT/BCIP substrate as described above and according to manufacturer's directions (Pharmacia). Nine positive clones were identified and screened through multiple probing rounds to confirm positives. Confirmed positive plaques were lifted and probed with a nAChR alpha 7 subunit probe. All of the plaques were positive on the screen with the alpha 7 probe, again indicating that Lynx1 binds the alpha subunit of the nAChR.

To more specifically assess the effect of Lynx protein on cholinergic synapses, *Xenopus* oocytes were utilized in vitro to determine acetylcholine receptor channel response in the presence of Lynx protein, as follows:

C. Lynx1 Protein Enhances nAChR Channel Response in *Xenopus Oocytes*

*Xenopus oocytes* were injected with alpha 7 RNA and ACh responsive current studied in the presence of control supernatant and Lynx/AP supernatant. The control utilized was cultured supernatant of 293T cells transfected with green fluorescent protein (GFP). The Lynx/AP supernatant was as described above in B. Increases observed in channel response, as measured by current, correspond significantly to 27% and 50% increases in the presence of Lynx1 versus the baseline response of the oocyte to ACh in the control.

The results in this Example are consistent with Lynx1 binding to alpha subunit of nAChr, more particularly, alpha 7 subtype.

Example 4

Homologs of Mouse Lynx1

The following set of experiments were undertaken to identify homologs of mouse Lynx1 and Lynx1, or related Lynx polypeptide family members and their encoding nucleic acids, these would be expected to include the human equivalent (or "ortholog") of mouse Lynx1 as well as new members of the family.

A genomic Southern of mouse DNA was performed under high stringency (65° C., 1×SSC, 0.1% SDS) and identifies 2 distinct bands hybridizing to Lynx1 coding sequence, one of which corresponds to known Lynx1. The second band indicates the presence of a second mouse gene homologous to Lynx1. This second gene, identified as a unique band on genomic Southerns, cosegregates in a genetic cross with Lynx1, as would be expected given the tight linkage of the Ly-6 superfamily of genes in the mouse (as previously described).

Blastn and tblastn searches of the nr and dbest databases (using Advanced Blast Search with default filter at www.ncbi.nlm.nih.gov) were performed with mature Lynx1 amino acid sequence (absent the signal sequence and after GPI attachment and cleavage) (SEQ ID NO:4) and with the complete coding nucleic acid sequence using software available at the ncbi website. Five mouse expressed sequence tags (ests) were identified that are essentially identical to part of the Lynx1 sequence. Four of these ests (AA13975 (SEQ ID NO:5), AA929210 (SEQ ID NO:6), AA268004 (SEQ ID NO:7) and AA711715 (SEQ ID NO: 8)) are in the 3' non-coding segment of the mRNA. The fifth est (AA619349 (SEQ ID NO:9)) was isolated from a mouse myotube cDNA library and includes part of the Lynx1 open reading frame. The sequences of these ests are shown in FIG. 7. It is important to note that the annotations for these five ests in the searched database identify no similarity or homology to any protein family.

In addition, four human ests were identified which all appear to be from the same cDNA/gene isolated from brain of a 55 year old male (H46196 (SEQ ID NO:10), H19490 (SEQ ID NO:11), H119572 (SEQ ID NO:12) and H46195 (SEQ ID NO: 13)). The sequences of these ests are shown in FIG. 7. These ests show 80% homology at both the nucleotide and amino acid level to Lynx1 in the available coding region, but show low homology outside of the coding region. Thus, these likely identify a second Lynx1-like gene, which we call Lynx2.

In order to identify and clone human homologs of Lynx1, including potential new Lynx family members, a human cDNA library (Stratagene, lambda zap dT primed from RNA of occipital cortex of a 57 year old woman) was screened with mature Lynx1 coding sequence as probe (i.e., probe corresponding to nucleic acid encoding the mature Lynx1 protein of SEQ ID NO:4) under high stringency (65° C., 1×SSC, 0.1% SDS). Several clones were identified. One positive clone was zapped and sequenced. The nucleotide sequence obtained (SEQ ID NO:14), including predicted protein sequence through the GPI attachment sequence (SEQ ID NO:15), is shown in FIG. 8. Initial sequence comparison indicates that this positive human clone corresponds to Lynx2, in that it is substantially homologons (80+%) to mouse Lynx1 in the predicted coding region but shows low homology outside of the coding region. In addition, this positive clone is substantially homogenous (over 80%) to human Lynx2 outside of the coding region.

Example 5

Lynx1 Structure Resembles α-Bungarotoxin

Structural data for members of this superfamily, such as CD59, αBtx, and cobratoxin demonstrate a strikingly similar tertiary structure (Fletcher et al., (1994) *Structure* 2, 185-199; Basus et al., (1993) *Biochem* 32, 12290-12298; LeGoas et al., (1992) *Biochem* 31, 4867-4875), despite their low overall sequence similarity. This is due to the fact that the conserved cysteine residues that constitute the Ly-6/neurotoxin motif are critical determinants in the overall topology of these molecules. The disulfide bonds created by these conserved cysteines create a rigid beta sheet core, out of which three more variable loops emerge. Conservation within Lynx1 of these critical residues suggest that Lynx1 is structurally related to the snake toxins and can adopt its receptor binding fold. To test whether or not Lynx1 adopts the snake toxin fold, comparative models of Lynx1 were built using three different template structures with the snake-toxin fold (FIG. 9). Experimental structures of CD59, α-bungarotoxin and cardiotoxin were used independently and in combination with each other to produce 4 different models. The evaluation of the models indicated that all four of them are reliable with a probability of having the correct fold of 0.84, 0.91, 0.93 and 0.94 for the best models based on CD59, cardiotoxin, α-bungarotoxin and all three templates, respectively. This indicates that the best individual template structure for Lynx1 is α-bungarotoxin, although the model based on all three templates is the best model produced. This is not surprising since the use of more than one related template usually improves the quality of the resulting comparative model (Sanchez, R and Sali, A. (1997) *Proteins* 1, 50-58). The false positive rate of the evaluation procedure for models of this size (70 residues) is only 7% (Sanchez, R. and Sali, A. (1998) *Proteins* 17, 355-362). As a negative control, a model for Lynx1 was built based on Bovine pancreatic trypsin inhibitor (BPT1), a small disulfide rich protein that does not adopt the snake-toxin fold. The probability of having the correct fold for this model was <0.5 (i.e., 0.28), supporting the prediction that Lynx1 can in fact adopt the snake toxin fold.

Methods for Structural Modeling:

Three-dimensional models of Lynx1 were built automatically by the computer program MODELLER-5 (Sali, A. and Blundell, T. (1993) *J Mol Buiol* 234, 779-815). MODELLER-5 implements comparative modeling by satisfaction of spatial restraints (Sali, A. and Blundell, T. (1993) *J Mol Biol* 234, 779-815). The input to MODELLER-5 was a multiple alignment of Lynx1 with members of the snake-toxin fold family of known three-dimensional structure. The alignment was prepared by hand following the pattern of conserved cysteine residues. First, MODELLER-5 derived many distance and dihedral angle restraints on the Lynx1 sequence from the alignment with the template proteins. One additional restraint was added manually to force a disulfide bridge between cysteine 6 and cysteine 11 in Lynx 1. Next, these homology-derived spatial restraints and CHARMM-22 energy terms (Brooks et al., (1983) *J Comp Chem* 4, 187-217) enforcing proper stereochemistry were combined into an objective function. Finally, the variable target function procedure, which employs methods of conjugate gradients and molecular dynamics with simulated annealing, was used to obtain the three-dimensional models by optimizing the objective function. In each case, ten slightly different three-dimensional models were calculated by varying the initial structure.

Since the sequence similarity between Lynx1 and the members of the snake-toxin fold family is not striking, different members of that family were used as templates. Specifically, CD59 (PDB code 1 erg), α-bungarotoxin (1 abt) and cardiotoxin (1 tgx) were used individually and in combination with each other as structural templates. BPT1 (6pti), another small disulfide rich protein that does not adopt the snake-toxin fold, was used as a template to test the ability of the evaluation procedure to detect incorrect folds. The reliability of the resulting models was predicted by a procedure based on statistical potentials of mean force (Sippl 1993) and using the resulting scores to predict the probability that the models have the correct fold by a procedure described by Sanchez and Sali (Sanchez R. and Sali, A. (1998) *Proteins* 17, 355-362).

Example 6

Lynx1 can Modulate Nicotinic Acetylcholine Receptor Function In Vitro

Figure 10A:
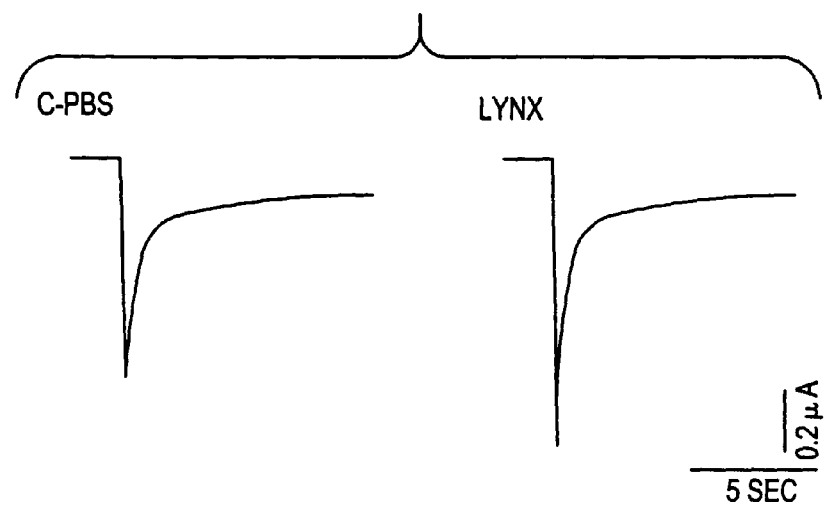
FIGS. 10A and 10B depicts the effect of Lynx on ACh responses in α 4β 2 nicotinic acetylcholine receptor expressing Xenopus oocytes. Lynx increases ACh-gated macroscopic current responses in voltage clamped Xenopus oocytes expressing α4β2 nAchRs. (A) Plot of cumulative results from 8 experiments. Column purified Lynx1 (1%, in oocyte recording media; see Methods) significantly increases the amplitude of macroscopic current responses to ACh (1 mM, 20 sec application, 5 min. inter-trial interval). Each experiment represents 20-60 ACh-evoked responses per condition including pretreatment controls (set to 100%) column-purified Lynx1 and a PBS control (cPBS). The latter control solution is the running buffer for the Lynx purification column, collected following isolation of the active Lynx1 fractions. (B) Representative macroscopic current responses to 1 mM ACh under control conditions (above) and in the 2$^{nd}$ ACh trial, following Lynx1 treatment.
Figure 10B:
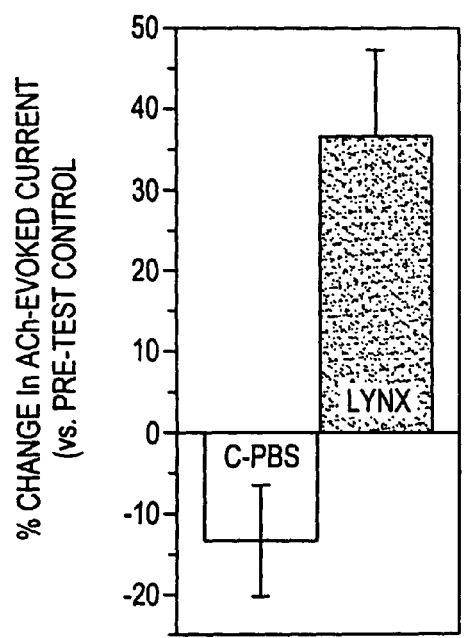

To test whether lynx1 functions through AChRs, we examined ACh-elicited macroscopic current responses in control and lynx1 treated *Xenopus* oocytes expressing recombinant α4β2 nAChR subunit cRNAs (FIG. 10). Injected oocytes were assayed in voltage clamp and inward current responses to ACh were measured for ~30 min before and after treatment with purified Lynx1. Sequential, pre-application responses to ACh (1 mM, 20 sec) differed by less than 2-3% when trials were separated by 5-minute intervals. After a stable baseline was established, a 20 second pulse of Lynx1 solution was applied, after which the first test pulse of ACh was delivered. Application of Lynx1 enhanced the amplitude of the ACh-evoked macroscopic currents by 30-40% compared with non treatment or column-passed PBS controls (n=8 oocytes, mean increase ~35%, p=0.001). Lynx1 application augmented ACh-evoked currents within the first or second post treatment trials and exhibited similar activity with all ACh concentrations tested (10 μM-1 mM). Similar results were obtained on α7 homomers (as described above), and with multiple Lynx1 preparations obtained from different heterologous expression systems, including conditioned media from mammalian cells transfected with Lynx1-HA or Lynx1-alkaline phosphatase (AP) fusion constructs, and bacterially expressed Lynx1 (data not shown). During the 20 second pre-application of Lynx1-PBS, in the absence of ACh, no Lynx1-evoked currents were detected in five of the six Lynx1 preparations tested. As Lynx1 does not reproducibly elicit currents when applied alone, we conclude that Lynx1 is not a ligand or neurotransmitter, but that it has the capacity to modulate receptor function in the presence of its natural ligand, ACh. Taken together, these data demonstrate that Lynx can act as a modulator of acetylcholine receptor function in vitro. Furthermore, the action of lynx1 on these receptors is distinct from that of the neurotoxins, since in the presence of lynx1 we observe an increase rather than a decrease in ACh-evoked macroscopic currents through these receptors.

This assay reveals that lynx can enhance the function of these receptors in the presence of its natural ligand, identifying lynx1 as a novel modulator of nAchRs in vitro. Neuropeptide modulators of receptor function, such as somatostatin and opioids, are released from the presynaptic terminals into the synaptic cleft (Maley et al., (1987) *J Comp Neural* 260, 483-490; Garside, S. and Mazurek, M. F. (1997) *Synapse* 27, 161-167), whereas lynx is normally present at the cell surface as a GPI anchored protein. This raises the possibility, therefore, that lynx1 is operating on nAChRs via a novel mechanism.

The observation that both nAChRs and lynx1 are expressed at extrasynaptic sites on the soma and proximal dendrites of Purkinje cells may be relevant and important to the in vivo function of lynx1. One of the main characteristics of the cholinergic projections from the brainstem are their wide and diffuse distribution throughout the nervous system. The mode of action of ACh in the CNS is unusual in that the majority of both cholinergic terminals from central projections and AChRs on target cells are diffusely distributed and extrasynaptic (Contant et al., (1996) *Neuroscience* 71, 937-947), although direct action of ACh at central synapses has been demonstrated (McGehee et al., (1995) *Science* 269, 1692-1696; Gray et al., (1996) *Nature* 383, 713-716). This has led to the hypothesis that cholinergic terminals modulate cell excitability through release of ambient levels of ACh (Descarries et al., (1997) *Prog in Neurobiology* 53, 603-725). Lynx1 may be important for regulating the response of extrasynaptic receptors to these ambient levels of ACh in select populations of neurons. Since cholinergic inputs have been implicated in many important functions including learning and memory, attention, and sleep-wake cycles (Changeux et al., (1998) *Brain Res Rev* 26, 198-216; Picciotto et al., (1995) *Nature* 374, 65-67; Everitt, B. J. and Robbins, T. W. (1997) *Ann Rev Psychol* 48, 649-684; Coull, J. T. (1998) *Prog. Neurobiol* 55, 343-361; Robbins, T. W. (1997) *Biol Psychol* 45, 57-71), and since the loss of central cholinergic function may be an important factor in the decline of cognitive function with age (Gallagher and Rapp, 1997) and in Alzheimer's disease (Robbins et al., (1997) *Behav Brain Res* 83, 15-23; Geula, C. (1998) *Neurology* 51, S18-529), an involvement of Lynx1 in modulation of cholinergic function in vivo would be very important.

Methods:

Lynx1 Preparation for Oocyte Recording:

The lynx1 cDNA corresponding to the lynx1 mature protein with its native signal sequence and without the GPI consensus sequence was cloned in frame with the hemagglutinin (HA) epitope, downstream of the CMV promoter (referred to as CMV2611). CMV2611 constructs were transfected into 293T cells, cultured for 3 days before supernatants were harvested. 5 mM HEPES pH=7.2 was added to the cultured supernatants, which were then precipitated with 50% ammonium sulfate. The pellet was resuspended in PBS, and fractionated on a Pharmacia Hiload Superdex 16/60 gel filtration column. Lynx1 containing fractions were detected by Western blotting or dot blotting assays using anti-HA antibody (Boehringer-Mannheim).

*Xenopus* Oocytes and cRNA Preparation and Injection:

*Xenopus* ovaries were collected and incubated in 2 mg/ml collagenase (Type 1, Sigma) in ND96 (Specialty Media) for 3-4 hr at room temperature. Oocytes were then washed 4 times with Barth's media, transferred to L-15 media, and were allowed to recover at 18° C. overnight before cRNA injection. Oocytes were maintained in L-15 at 18 C after cRNA injection and experiments performed between 1 and 7 days after injection. cDNAs encoding chicken nAchR subunits α4 and β2 in the PGH19 oocyte expression vector were linearized and used as template for run-off transcription using the T7 promoter. Oocytes were injected with 20 nl of cRNA at a final concentration ~0.05 ng/μl. α4 and β2 cRNAs were injected at a ratio of 1:1.

Electrophysiological recording data acquisition and analysis: Macroscopic currents were recorded with a GeneClamp 500 (Axon Instruments) amplifier using a two-electrode voltage clamp with active ground configuration. Electrode resistance's ranged between 0.5 and 5MΩ and were filled 3M KCl. Membrane potential was clamped to −70 mV; only oocytes with leak currents of less than 100 nA were used.

The extracellular recording solution included (in mM): 82.5 NaCl, 2 KCl, 1 $CaCl_2$, 1 $MgCl_2$, 10 HEPES, pH 7.5 (all reagents from Sigma). Uninjected and mock-injected oocytes did not respond to ACh rendering the inclusion of atropine in the extracellular perfusion solution unnecessary. ACh (RBI) was prepared in extracellular solution at concentrations 10 μM-1 mM. Oocytes were perfused at ~5 mL/min and were exposed to sequential, 20 s duration applications of agonist with 5 minute inter-trial intervals. Stable baseline responses to ACh (i.e. an inter-trial variance of <2.5%) are typically achieved within 2-3 trials under these recording conditions.

Following an initial assessment of 4 sequential pre-treatment responses to ACh, solutions containing either 1% column-passed PBS or column purified lynx1 in PBS were applied to oocytes for 20 s. ACh-evoked macroscopic currents were recorded again, immediately after exposure to the test solution (t=0) and at five minute intervals, thereafter (t=1-5). Oocytes were perfused in control media for 30 minutes before the next test solution was applied. Macroscopic currents were recorded and the rise times, amplitude and time course of the elicited currents analyzed using Pclamp6 (Axon Instruments). Graphical and statistical analyses utilized Origin 5.1 (Microcal Software).

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

SEQUENCE LISTING

```
<160> NUMBER OF SEQ ID NOS: 24

<210> SEQ ID NO 1
<211> LENGTH: 4031
<212> TYPE: DNA
<213> ORGANISM: Mus musculus

<400> SEQUENCE: 1
taccaacacc gcacgaagtg tgtacagatt cccagttaga cagcaggagg gacctgggag      60
cggccagggg gatgttttat ctctaagaga ccaagagctc aggcagggct tctgtgccct     120
gcttcctccc tggcttgagc tggatcctgg accagctgct gacctcctgt tcactctggc     180
actgccctca cgtctccgtc atgacccatc tgctcacagt gttcctggtg gccctgatgg     240
gcctgcctgt ggcccaggct ctggagtgcc acgtgtgtgc ctacaatgga gacaactgct     300
tcaaacccat gcgctgccca gccatggcca cctactgtat gaccacacga acttacttca     360
ccccataccg gatgaaggtg aggaagtcct gtgtcccag ctgctttgaa accgtgtacg      420
atggctattc caagcatgca tctgccacct cctgttgcca gtactacctc tgcaacggtg     480
ctggctttgc tacccggtg accttggccc tggtcccagc actcctagct accttctgga     540
gcttgctgta aagctcggtt ccccaagcca gatccactca aacgcaacac tctcaaaaaa     600
cacagtttcc ctctctctcc caattcactc cacccaacgc tcttccttct gacactcctc     660
aactaccacg aggtcccatg gctacctacg aaagaactga tggcatccag atacctcact     720
ccaaggtcat tttcagaagg ctgacatgtg gacctgtaat gtgcccaccc atgggtgggg     780
caggctgggc ttctcctcta cccaagatca ggggcatctg ggagaatgtt tatggaggag     840
gggtcatcac tcaagtcaag gagcactgat ttgatagaat tagtagccaa actccacctt     900
cagaaccctg cctcagtcta cccagtagag gatgggtctg ctagaggtga ggggaggaga     960
gcggcggaga ataacgagct ggctagaagc agagaaagac tcagcagggc tgtctccgaa    1020
gatcagcgcg gcttgccaga gcaaatgtga tgtggaagca acgagctggc tagaagcaga    1080
gaaagactca gcagggctgt ctccgaagat cagcgcggct tgccagagca aatgtgatgt    1140
ggaagccatg tgaggaagcc ctttgtcatt tccacttatc tgaggaactc tgccagacct    1200
gatgttggga tagccattgg ccaagggttc ctagcaacgg cgtcatttcc ataggccact    1260
gaaatccctc cagccccagc tcagcaggcc ccttgacctc cactacagtc cttcattcac    1320
acaccagctg ctgggccttg aagttggcag ggacttggga gcaggtgacc catgctattt    1380
tttgtctggc ctgttattct gggcatggca agaaagggatc agacgcaggt cagagcaggg    1440
cagtagggcg actgagacag ggaaacagac ttcagccagt ggcttcccag gtcccgtagg    1500
cagctcctac atccttcagt ctcttgttac attcccggga gacaaatata cagggagcca    1560
```

-continued

```
agccgagtgc taggtgatga ctgcctgtga agtctattgt ggccacagac tgctgggtac    1620
caagtctcag gagaacccag cctagattta ggagacacag atctgccttt catgcagtgt    1680
agctgtcctt gggagcctta ccatgctctc taactagttc ctcaactcac atgtcactga    1740
ggaaccccct aacactggcc cagcccaggg gtcgggatgc tggccaatgt ccatggagtg    1800
ggactacccc tggagagtcc ttgggtcatc acatcacaaa tgttttattc caacctccca    1860
gtggtgagag ctcgggacac aaaggtccat cctggggacc ttcttcctgg ttctaggcag    1920
acctgaactc tgtctgctgc tagagctgat gtggttttcc gcctcagttt cctcctccgg    1980
ggataggcca ccggaggatt tgggagggtg ggagggcat cctgctgatg gctcgccga     2040 ggttctcagg aacaggaacg ggcggggctt tagtacacag gtgagttggg tgggaactgg    2100
cccggagctg aggagacact gactgggcag agggaagatg agtctcaagg gagggcagga    2160
aaagggaggg ggagcgcgca tgcacatgtg cactcagtgc aggctacaga gcccaaaagg    2220
cagcactggc tgtggtgtcc cctgaggccc aggcaagatg ctaggaggaa gccaatgctg    2280
cccccacctg agctcacatg gaacatgcac accaccagca gcagcagcaa gcattgagac    2340
tgacctgtgg acgccatagg gcactggcaa ggagggtcag aggcgggtcc ctgactcagt    2400
gggtgaggcc cggaaacat tatcctgtta ccctgcgtgt gcaagatcat tgtccccagc    2460
tagatggcgt cctcaaccaa aactgagagg agcccagtt caggtcctcc ctcctaccac     2520
aagggggtgg tgtggaggag gcttgattgc ccttggagaa gcaccggtac tgcagagctg    2580
ggggccagct tctttcatct gtgtctagac accgaccaga taggccccac agtggcaaca    2640
ctgccacaca gtcctacaag aagccctgtg cctagctagc acagagcccc aaaaggtgct    2700
caattaatac agggccaagc ctgccagtgg ggggatgca gattagggga acagacccag    2760
atggcctgtc ctgaaccctg tctggggtgg tgtgatgagc atctgtctag cccactgcag    2820
gtggctctac acactccaca acagttctgc aaaagtgtat gaggtggtca ttactgcgcc    2880
cctctcacag gtaaaggcac tgaggcacgg aggagtgagg cacttcattt tcctgggcca    2940
ttcaactttc caggaccaac acattcaact atgggtacta ctccaatagc tggggttctt    3000
tgaggctggg cccccctgaag atgatagtgg cttcatcaac cagagaattt cagagtgcag    3060
tgttgtagga gcctatgaac ctgaaatgtc agaactggag gtttgagggg ctgaggggta    3120
ggccaggggt gtctggcccc ttgtgtggag acagagagag agggaacatg ggatggggta    3180
gtagagagaa gtgcaaagga gcgtcagcct ttctcagggc taatgctgtc agggacgagg    3240
gctcaagcct gtgagtgttc tcacactgtg ataaacagtg gccctcaac acagacggtg     3300 tccagagtgg ccggcagtgg ttatctagag ttgcaatctg gaagcctctt ggtagtcact    3360
ggagagaggc cgcttgatgg gacagcacca aatgtgtgtg cttctgtggg atgtgaggaa    3420
gctgggtcag cgcatgaagc caaagcgtcc ttcagagcag aggggtggct ggtctagtcc    3480
accagagaca agctatccag tgagagtcat actctgtcac cgtctctgtg attaccttac    3540
cccaaagcag acggggacgg gatgcagagc acccgtgtct tcatcttctg cggcaagcac    3600
gtgagttcac attctgaaac tctagaaaga tttccaggag tggggtgtgc ctttgctttg    3660
gtgcatggtt acttcctggc aagcaccgtg gcatcccgca gcactgagtg acctgggctc    3720
ctcaagccat ctcattggtg aaatgacagt gccagtaccc ctcagctgg ctcttggagg     3780 cctgtgcatg gggtctgcac agaggaggcc cccaaactat gcatggacgg acacgtgatg    3840
cctagcactt cccttggttg tgtctctgcc aaccccaggc tctcacccag caaggaaatg    3900
aaatccactt ttatgacaca tctccctccc ccagccagct ccattcacct atatgccagg    3960
```

```
gtggtccctt tcaatgtctg tcccccattg gatgaataaa caagcgaagg acaaaaaaaa        4020
aaaaaaaaaa a                                                             4031
```

<210> SEQ ID NO 2
<211> LENGTH: 117
<212> TYPE: PRT
<213> ORGANISM: Mus musculus

<400> SEQUENCE: 2

```
Met Thr His Leu Leu Thr Val Phe Leu Val Ala Leu Met Gly Leu Pro
 1               5                  10                  15

Val Ala Gln Ala Leu Glu Cys His Val Cys Ala Tyr Asn Gly Asp Asn
             20                  25                  30

Cys Phe Lys Pro Met Arg Cys Pro Ala Met Ala Thr Tyr Cys Met Thr
         35                  40                  45

Thr Arg Thr Tyr Phe Thr Pro Tyr Arg Met Lys Val Arg Lys Ser Cys
     50                  55                  60

Val Pro Ser Cys Phe Glu Thr Val Tyr Asp Gly Tyr Ser Lys His Ala
 65                  70                  75                  80

Ser Ala Thr Ser Cys Cys Gln Tyr Tyr Leu Cys Asn Gly Ala Gly Phe
                 85                  90                  95

Ala Thr Pro Val Thr Leu Ala Leu Val Pro Ala Leu Leu Ala Thr Phe
            100                 105                 110

Trp Ser Leu Leu Leu
        115
```

<210> SEQ ID NO 3
<211> LENGTH: 16
<212> TYPE: PRT
<213> ORGANISM: Mus musculus

<400> SEQUENCE: 3

```
Thr Thr Arg Thr Tyr Phe Thr Pro Tyr Arg Met Lys Val Arg Lys Ser
 1               5                  10                  15
```

<210> SEQ ID NO 4
<211> LENGTH: 72
<212> TYPE: PRT
<213> ORGANISM: Mus musculus

<400> SEQUENCE: 4

```
Leu Glu Cys His Val Cys Ala Tyr Asn Gly Asp Asn Cys Phe Lys Pro
 1               5                  10                  15

Met Arg Cys Pro Ala Met Ala Thr Tyr Cys Met Thr Thr Arg Thr Tyr
             20                  25                  30

Phe Thr Pro Tyr Arg Met Lys Val Arg Lys Ser Cys Val Pro Ser Cys
         35                  40                  45

Phe Glu Thr Val Tyr Asp Gly Tyr Ser Lys His Ala Ser Ala Thr Ser
     50                  55                  60

Cys Cys Gln Tyr Tyr Leu Cys Asn
 65                  70
```

<210> SEQ ID NO 5
<211> LENGTH: 473
<212> TYPE: DNA
<213> ORGANISM: Mus musculus

<400> SEQUENCE: 5

```
gtgagcccgg gaaacattat cctgttaccc tgcgtgtgca agatcattgt ccccagctag        60
```

| | |
|---|---|
| atggcgtcct caaccaaaac tgagaggagc cccagttcag gtcctccctc ctaccacaag | 120 |
| ggggtggtgt ggaggaggct tgattgccct tggagaagca ccggtactgc agagctgggg | 180 |
| gccagcttct ttcatctgtg tctagacacc gaccagatag ccccacagt ggcaacactg | 240 |
| ccacacagcc ctacaagaag ccctgtgcct agctagcaca gagccccaaa aggtgctcaa | 300 |
| ttaatacagg gccaagcctg ccagtggggg ggatgcagat taggggaaca gacccagatg | 360 |
| gcctgtcctg aaccctgtct ggggtggtgt gatgagcatc tgtctagccc actgcaggtg | 420 |
| gctctacaca ctccacaaca gttctgcaaa agtgtatgag gtggtcatta ctg | 473 |

<210> SEQ ID NO 6
<211> LENGTH: 413
<212> TYPE: DNA
<213> ORGANISM: Mus musculus

<400> SEQUENCE: 6

| | |
|---|---|
| tgaaatgtca gaactggagg tttgaggggc tgaggggtag gccagggtg tctggcccctt | 60 |
| gtgtggagac agagagagag ggaacatggg atggggtagt agagagaagt gcaaaggagc | 120 |
| gtcagctttc tcagggctaa tgctgtcagg gacgagggct caagctgtga gtgttctcac | 180 |
| actgtgataa acagtggccc ctcaacacag acggtgtcca gagtggccgg cagtggttat | 240 |
| ctagagttgc aatctggaag cctcttggta gtcactggag agaggccgct tgatgggaca | 300 |
| gcaccaaatg tgtgtgcttc tgtgggatgt gaggaagctg ggtcagcgca tgaagccaaa | 360 |
| gcgtccttca gagcagaggg gtggctggtc tagtccacca gagacaagct atc | 413 |

<210> SEQ ID NO 7
<211> LENGTH: 400
<212> TYPE: DNA
<213> ORGANISM: Mus musculus

<400> SEQUENCE: 7

| | |
|---|---|
| gtgggatgtg aggaagctgg gtcagcgcat gaagccaaag cgtccttcag agcagagggg | 60 |
| tggctggtct agtccaccag agacaagcta tccagtgaga gtcatactct gccaccgtct | 120 |
| ctgtgattac cttaccccaa agcagacggg gacgggatgc agacacccgt gtcttcatct | 180 |
| tctgcggcaa cacgtgagtt cacattctga aactctagaa agatttccag gagtggggtg | 240 |
| tgcctttgct ttggtgcatg gttacttcct ggcaagcacc gtggcatccc gcagcactga | 300 |
| gtgacctggg ctcctcaagc catctcattg gtgaaatgac agtgccagta ccctctcagc | 360 |
| tggctcttgg aggcctgtgc atggggtctg cacagaggag | 400 |

<210> SEQ ID NO 8
<211> LENGTH: 160
<212> TYPE: DNA
<213> ORGANISM: Mus musculus

<400> SEQUENCE: 8

| | |
|---|---|
| ttcggatcct tgctgcgccc tctcacaggt aaaggcactg aggcacggag gagtgaggca | 60 |
| cttcattttc ctgggccatt caactttcca ggaccaacac attcaactat gggtactact | 120 |
| ccaatagctg gggttctttg aggctggggc ccctgaagat | 160 |

<210> SEQ ID NO 9
<211> LENGTH: 435
<212> TYPE: DNA
<213> ORGANISM: Mus musculus

<400> SEQUENCE: 9

```
attcggatcc ttgtgcgatg cggtaccaac accgcacgaa gtgtgtacag attcccagtt    60
agacagcagg agggacctgg gagcggccag ggggatgttt tatctctaag agaccaagag   120
ctcaggcagg gcttctgtgc cctgcttcct ccctggcttg agctggatcc tggaccagct   180
gctgacctcc tgttcactct ggcactgcct cacgtctccg tcatgaccca tctgctcaca   240
gtgttcctgg tggccctgat ggctgcctgt ggccaggctc tggagtgcca cgtgtgtgcc   300
tacaatggag acaactgctt caaacccatg cgctgcccag ccatggccac ctactgtatg   360
accacacgaa cttacttcac cccataccgg atgaaggtga ggaagtcctg tgtcccagc    420 tgctttgaaa ccgtg                                                    435
```

<210> SEQ ID NO 10
<211> LENGTH: 381
<212> TYPE: DNA
<213> ORGANISM: Homo sapiens
<220> FEATURE:
<221> NAME/KEY: misc_feature
<222> LOCATION: 72
<223> OTHER INFORMATION: n is A, C, G, or T at position 72

<400> SEQUENCE: 10

```
gtgcttggag tagccatcat acacagtctc gaagcagcgg ggcacgcagg acttactgac    60
cttcatcctg gnggggtgt agtaggtgcg cgtggtcatg cagtaggcaa ccatagccgg    120
gcagcgcatg gggttgaagc agttgtctcc gttgtaggca cacacgtggc agtccaaggc   180
ctgggcagag gtaagcccat gaggaccacc aggatcaggg tgagcagggg cgtcatggct   240
gcaggcagga gggcagcgtg ggagtgggga ggtcaacagc agctagccct gggatccaac   300
tcaggggtgg cgcacagagg atccaacttc agggtggttg cgcagaggac gtggggccg    360 gccctgcctt cccggagctc c                                             381
```

<210> SEQ ID NO 11
<211> LENGTH: 289
<212> TYPE: DNA
<213> ORGANISM: Homo sapiens
<220> FEATURE:
<221> NAME/KEY: misc_feature
<222> LOCATION: 12, 75, 102, 168, 177, 241, 249, 259 285
<223> OTHER INFORMATION: n can be A, C, G, or T at positions 12, 75,
      102, 168, 177, 241, 249, 259, or 285

<400> SEQUENCE: 11

```
gatgggtttt tntaggtgga cgcgtgcttg gagtagccat catacacagt ctcgaagcag    60
cggggcacgc agganttact gaccttcatc ctggtggggg tntagtaggt gcgcgtggtc   120
atgcagtagg caaccatagc cgggcagcgc atggggttga agcagttntc tccgttntag   180
gcacacacgt gggcagtcca aggcctgggg ccagaggtaa gcccatgagg accaccaggg   240
ntcagggtna gcaggggcnt catggctgca ggcaggaggg cagcntggg                289
```

<210> SEQ ID NO 12
<211> LENGTH: 391
<212> TYPE: DNA
<213> ORGANISM: Homo sapiens
<220> FEATURE:
<221> NAME/KEY: misc_feature
<222> LOCATION: 1, 30, 32, 34, 110, 368, 380, 385
<223> OTHER INFORMATION: n can be A, C, G, or T at positions 1, 30, 32,
      34, 110, 368, 380, 385

<400> SEQUENCE: 12

```
nattcggcac gaaggctgcc gcgggacggn anangatagc ctgcgagtgt ccgggcggaa    60
```

```
cacggttgca gcattcccag tagaccagga gctccgggag gcagggccgn ccccacgtcc    120
tctgcgcacc accctgagtt ggatcctctg tgcgccaccc ctgagttgga tccagggcta    180
gctgctgttg acctccccac tcccacgctg ccctcctgcc tgcagccatg acgcccctgc    240
tcaccctgat cctggtggtc ctcatgggct tacctctggc ccaggcttg gactgccacg     300 tgtgtgccta acggagac aactgcttca accccatggc gctgcccggc tatggtttgc     360
tgattggnat ggaccaaggn ggaantgatt a                                    391
```

<210> SEQ ID NO 13
<211> LENGTH: 429
<212> TYPE: DNA
<213> ORGANISM: Homo sapiens
<220> FEATURE:
<221> NAME/KEY: misc_feature
<222> LOCATION: 18, 32, 34, 36, 47, 111, 329, 367, 390, 420
<223> OTHER INFORMATION: n can be A, C, G, or T at positions 18, 32, 34, 36, 47, 111, 329, 367, 390 or 420

<400> SEQUENCE: 13

```
atttcggcac gaaggctngc cgcggggcga anangnatag cctgcgnagt gtccgggcgg    60
aacacggttg cagcactccc agtagaccag gagctccggg aggcagggcg nccccacgtc    120
ctctgcgcac caccctgagt tggatcctct gtgcgccacc cctgagttgg atccagggct    180
agctgctgtt gacctcccca ctcccacgct gccctcctgc ctgcagccat gacgcccctg    240
ctcaccctga tcctgggtgg tcctcatggg cttacctctg gcccagggc ttgggactgc     300 cacgtgtgtg gctaacaac ggagacaant gcttcaaccc catggcgctg cccggctatg     360
gttggcnaat tgcatggacc aaggggcacn tattacaacc cccaccaggg atgaaaggtn    420
agtaaagtt                                                             429
```

<210> SEQ ID NO 14
<211> LENGTH: 729
<212> TYPE: DNA
<213> ORGANISM: Homo sapiens
<220> FEATURE:
<221> NAME/KEY: misc_feature
<222> LOCATION: 1, 14
<223> OTHER INFORMATION: n can be A, C, G, or T at positions 1 and 14

<400> SEQUENCE: 14

```
ngaaaggttt tccngaatgg gaaaggggc aggggggca aaggaattta wtgggtaadg     60
gcwggttttt cccarttcaa ggagttgtaa aakgagggcc aggggattgta ataggartta    120 attrtgaggg agaaattggg tacgggcccc mcttkrdgty ggayggtatc satwaggctc    180
tgatatsgaa ttcccctcc tabtcgtcgc grcgtmgcgt mcgmgggtta ctcccaggcg     240
cggyggtacc tcacggtggt gaaggtcaca gggttgcagc aytcccagta gaccaggagc    300
tccgggaagg cagggccggc cccacgtcct ctgcgcacca ccctgagttg gatcctctgt    360
gcgccacccc tgagttggat ccagggctag ctgctgttga cctccccact cccacgctgc    420 ctcctgcct gcagccatga cgcccctgct caccctgatc ctggtggtcc tcatgggctt     480
acctctggcc caggccttgg actgccacgt gtgtgcctac aacggagaca actgcttcaa    540
ccccatgcgc tgcccggcta tggttgccta ctgcatgacc acgcgcacct aytacacccc    600
caccaggatg aargtcagta agtcctgcgt gccccgctgt tcgagactg tgtatgatgg      660 ctactccaag cacgcgtcca ccacctcctg ctgccagtac gaactctgca acggaccggc    720
cttgccacc                                                             729
```

```
<210> SEQ ID NO 15
<211> LENGTH: 97
<212> TYPE: PRT
<213> ORGANISM: Homo sapiens

<400> SEQUENCE: 15

Met Thr Pro Leu Leu Thr Leu Ile Leu Val Val Leu Met Gly Leu Pro
 1               5                  10                  15

Leu Ala Gln Ala Leu Asp Cys His Val Cys Ala Tyr Asn Gly Asp Asn
            20                  25                  30

Cys Phe Asn Pro Met Arg Cys Pro Ala Met Val Ala Tyr Cys Met Thr
        35                  40                  45

Thr Arg Thr Tyr Tyr Thr Pro Thr Arg Met Lys Val Ser Lys Ser Cys
    50                  55                  60

Val Pro Arg Cys Phe Glu Thr Val Tyr Asp Gly Tyr Ser Lys His Ala
65                  70                  75                  80

Ser Thr Thr Ser Cys Cys Gln Tyr Glu Leu Cys Asn Gly Pro Ala Leu
                85                  90                  95

Pro

<210> SEQ ID NO 16
<211> LENGTH: 104
<212> TYPE: PRT
<213> ORGANISM: Mus musculus

<400> SEQUENCE: 16

Met Gly Leu Pro Val Ala Gln Ala Leu Glu Cys His Val Cys Ala Tyr
 1               5                  10                  15

Asn Gly Asp Asn Cys Phe Lys Pro Met Arg Cys Pro Ala Met Ala Thr
            20                  25                  30

Tyr Cys Met Thr Thr Arg Thr Tyr Phe Thr Pro Tyr Arg Met Lys Val
        35                  40                  45

Arg Lys Ser Cys Val Pro Ser Cys Phe Glu Thr Val Tyr Asp Gly Tyr
    50                  55                  60

Ser Lys His Ala Ser Ala Thr Ser Cys Cys Gln Tyr Tyr Leu Cys Asn
65                  70                  75                  80

Gly Ala Gly Phe Ala Thr Pro Val Thr Leu Ala Leu Val Pro Ala Leu
                85                  90                  95

Leu Ala Thr Phe Trp Ser Leu Leu
            100

<210> SEQ ID NO 17
<211> LENGTH: 6
<212> TYPE: PRT
<213> ORGANISM: Unknown
<220> FEATURE:
<223> OTHER INFORMATION: consensus sequence
<220> FEATURE:
<221> NAME/KEY: VARIANT
<222> LOCATION: 2
<223> OTHER INFORMATION: Xaa is a charged residue (Met, Glu, Gln, or
      Arg).
<220> FEATURE:
<221> NAME/KEY: VARIANT
<222> LOCATION: 4
<223> OTHER INFORMATION: Xaa is an aromatic residue (Phe, Tyr, or His).
<220> FEATURE:
<221> NAME/KEY: VARIANT
<222> LOCATION: 5
<223> OTHER INFORMATION: Xaa means any amino acid residue

<400> SEQUENCE: 17

Leu Xaa Cys Xaa Xaa Cys
```

<210> SEQ ID NO 18
<211> LENGTH: 8
<212> TYPE: PRT
<213> ORGANISM: Unknown
<220> FEATURE:
<223> OTHER INFORMATION: consensus sequence
<220> FEATURE:
<221> NAME/KEY: VARIANT
<222> LOCATION: 3, 4, 5
<223> OTHER INFORMATION: Xaa means any amino acid residue

<400> SEQUENCE: 18

Cys Cys Xaa Xaa Xaa Leu Cys Asn
1               5

<210> SEQ ID NO 19
<211> LENGTH: 73
<212> TYPE: PRT
<213> ORGANISM: Mus musculus

<400> SEQUENCE: 19

Leu Arg Cys His Val Cys Thr Ser Ser Asn Cys Lys His Ser Val
1               5                   10                  15

Val Cys Pro Ala Ser Ser Arg Phe Cys Lys Thr Thr Asn Thr Val Glu
            20                  25                  30

Pro Leu Arg Gly Asn Leu Val Lys Lys Asp Cys Ala Glu Ser Cys Thr
        35                  40                  45

Pro Ser Tyr Thr Leu Gln Gly Gln Val Ser Ser Gly Thr Ser Ser Thr
    50                  55                  60

Gln Cys Cys Gln Glu Asp Leu Cys Asn
65                  70

<210> SEQ ID NO 20
<211> LENGTH: 79
<212> TYPE: PRT
<213> ORGANISM: Mus musculus

<400> SEQUENCE: 20

Leu Glu Cys Tyr Gln Cys Tyr Gly Val Pro Phe Glu Thr Ser Cys Pro
1               5                   10                  15

Ser Ile Thr Cys Pro Tyr Pro Asp Gly Val Cys Val Thr Gln Glu Ala
            20                  25                  30

Ala Val Ile Val Asp Ser Gln Thr Arg Lys Val Lys Asn Asn Leu Cys
        35                  40                  45

Leu Pro Ile Cys Pro Pro Asn Ile Glu Ser Met Glu Ile Leu Gly Thr
    50                  55                  60

Lys Val Asn Val Lys Thr Ser Cys Cys Gln Glu Asp Leu Cys Asn
65                  70                  75

<210> SEQ ID NO 21
<211> LENGTH: 71
<212> TYPE: PRT
<213> ORGANISM: Mus musculus

<400> SEQUENCE: 21

Leu Thr Cys Tyr His Cys Phe Gln Pro Val Val Ser Ser Cys Asn Met
1               5                   10                  15

Asn Ser Thr Cys Ser Pro Asp Gln Asp Ser Cys Leu Tyr Ala Val Ala
            20                  25                  30

Gly Met Gln Val Tyr Gln Arg Cys Trp Lys Gln Ser Asp Cys His Gly

```
                35                  40                  45
Glu Ile Ile Met Asp Gln Leu Glu Glu Thr Lys Leu Lys Phe Arg Cys
             50                  55                  60

Cys Gln Phe Asn Leu Cys Asn
 65                  70

<210> SEQ ID NO 22
<211> LENGTH: 61
<212> TYPE: PRT
<213> ORGANISM: Serpentes

<400> SEQUENCE: 22

Leu Glu Cys His Asn Gln Gln Ser Ser Gln Thr Pro Thr Thr Thr Gly
 1               5                  10                  15

Cys Ser Gly Gly Glu Thr Asn Cys Tyr Lys Lys Arg Trp Arg Asp His
             20                  25                  30

Arg Gly Tyr Arg Thr Glu Arg Gly Cys Gly Cys Pro Ser Val Lys Asn
         35                  40                  45

Gly Ile Glu Ile Asn Cys Cys Thr Thr Asp Arg Cys Asn
     50                  55                  60

<210> SEQ ID NO 23
<211> LENGTH: 66
<212> TYPE: PRT
<213> ORGANISM: Serpentes

<400> SEQUENCE: 23

Ile Val Cys His Thr Thr Ala Thr Ser Pro Ile Ser Ala Val Thr Cys
 1               5                  10                  15

Pro Pro Gly Glu Asn Leu Cys Tyr Arg Lys Met Trp Cys Asp Ala Phe
             20                  25                  30

Cys Ser Ser Arg Gly Lys Val Val Glu Leu Gly Cys Ala Ala Thr Cys
         35                  40                  45

Pro Ser Lys Lys Pro Tyr Glu Glu Val Thr Cys Cys Ser Thr Asp Lys
     50                  55                  60

Cys Asn
 65

<210> SEQ ID NO 24
<211> LENGTH: 64
<212> TYPE: PRT
<213> ORGANISM: Serpentes

<400> SEQUENCE: 24

Leu Thr Cys Val Thr Ser Lys Ser Ile Phe Gly Ile Thr Thr Glu Asn
 1               5                  10                  15

Cys Pro Ala Gly Gln Asn Leu Cys Phe Lys Arg Arg His Tyr Val Ile
             20                  25                  30

Pro Arg Tyr Thr Glu Ile Thr Arg Gly Cys Ala Ala Thr Cys Pro Ile
         35                  40                  45

Pro Glu Asn Tyr Asp Ser Ile His Cys Cys Lys Thr Asp Lys Cys Asn
     50                  55                  60
```

What is claimed is:

1. An isolated Lynx polypeptide having the amino acid sequence of SEQ ID NO:2.

2. The isolated polypeptide of claim 1 which is obtained from mammalian cells.

3. An isolated immunogenic polypeptide comprising an amino acid sequence of SEQ ID NO:2.

4. The polypeptide of claim 3 further comprising the amino acid sequence set forth in SEQ ID NO:3.

5. The polypeptide of claim 1, wherein the polypeptide is radiolabeled.

* * * * *